United States Patent
Wicher et al.

(10) Patent No.: US 12,351,642 B2
(45) Date of Patent: Jul. 8, 2025

(54) TFR-SPECIFIC BINDING MOIETIES AND TRANSCYTOSIS METHOD TO SELECT VNARS THAT CROSS CELLULAR BARRIERS

(71) Applicant: Ossianix, Inc., Philadelphia, PA (US)

(72) Inventors: Krzysztof B. Wicher, Cambridge (GB); Julia Lynn Rutkowski, Bryn Mawr, PA (US); Pawel Stocki, Royston (GB)

(73) Assignee: Ossianix, Inc., Bryn Mawr, PA (US)

(*) Notice: Subject to any disclaimer, the term of this patent is extended or adjusted under 35 U.S.C. 154(b) by 1060 days.

(21) Appl. No.: 17/275,911

(22) PCT Filed: Sep. 13, 2019

(86) PCT No.: PCT/US2019/051114
§ 371 (c)(1),
(2) Date: Mar. 12, 2021

(87) PCT Pub. No.: WO2020/056327
PCT Pub. Date: Mar. 19, 2020

(65) Prior Publication Data
US 2021/0395381 A1    Dec. 23, 2021

Related U.S. Application Data

(60) Provisional application No. 62/731,279, filed on Sep. 14, 2018.

(51) Int. Cl.
| | | |
|---|---|---|
| C07K 16/28 | (2006.01) | |
| A61K 38/00 | (2006.01) | |
| A61K 39/00 | (2006.01) | |
| A61K 47/68 | (2017.01) | |
| C12N 15/10 | (2006.01) | |
| G01N 33/50 | (2006.01) | |
| G01N 33/68 | (2006.01) | |

(52) U.S. Cl.
CPC ...... *C07K 16/2881* (2013.01); *A61K 47/6849* (2017.08); *C12N 15/1037* (2013.01); *G01N 33/5035* (2013.01); *G01N 33/6845* (2013.01); *A61K 38/00* (2013.01); *A61K 2039/505* (2013.01); *C07K 2317/20* (2013.01); *C07K 2317/31* (2013.01); *C07K 2317/565* (2013.01); *C07K 2317/567* (2013.01); *C07K 2317/569* (2013.01); *C07K 2317/622* (2013.01); *C12N 2800/00* (2013.01)

(58) Field of Classification Search
CPC ............ C07K 16/2881; C07K 2317/20; C07K 2317/31; C07K 2317/565; C07K 2317/567; C07K 2317/569; C07K 2317/622; C07K 2317/64; A61K 47/6849; A61K 2039/505; A61K 38/00; C12N 15/1037; C12N 2800/00; G01N 33/5035; G01N 33/6845
See application file for complete search history.

(56) References Cited

U.S. PATENT DOCUMENTS

| | | |
|---|---|---|
| 7,943,129 B2 | 5/2011 | Muruganandam et al. |
| 10,479,990 B2 | 11/2019 | Häsler |
| 10,722,576 B2 | 7/2020 | Häsler et al. |
| 11,097,010 B2 | 8/2021 | Stocki et al. |
| 2016/0333103 A1 | 11/2016 | Häsler |
| 2017/0198281 A1 | 7/2017 | Häsler |
| 2017/0348416 A1 | 12/2017 | Häsler et al. |
| 2019/0175746 A1 | 6/2019 | Stocki |
| 2020/0024354 A1 | 1/2020 | Häsler et al. |
| 2020/0115702 A1 | 4/2020 | Häsler |
| 2020/0316195 A1 | 10/2020 | Häsler et al. |
| 2021/0403591 A1 | 12/2021 | Stocki et al. |

FOREIGN PATENT DOCUMENTS

| | | |
|---|---|---|
| WO | 2002057445 A1 | 7/2002 |
| WO | 2003014161 A2 | 2/2003 |
| WO | 2005118629 A1 | 12/2005 |

(Continued)

OTHER PUBLICATIONS

Barelle C, Porter A. VNARs: An Ancient and Unique Repertoire of Molecules That Deliver Small, Soluble, Stable and High Affinity Binders of Proteins. Antibodies. 2015; 4(3):240-258. https://doi.org/10.3390/antib4030240 (Year: 2015).*

Millán-Gómez D. et al In silico-designed mutations increase variable new-antigen receptor single-domain antibodies for VEGF165 neutralization. Oncotarget. Jun. 15, 2018;9(46):28016-28029. doi: 10.18632/oncotarget.25549. PMID: 29963259; PMCID: PMC6021326. (Year: 2018).*

Ng et al. (2006) "Molecular events contributing to cell death in malignant human hematopoietic cells elicited by an IgG3-avidin fusion protein targeting the transferrin receptor," Blood 108:2745-54.

Niewoehner et al. (2014) "Increased Brain Penetration and Potency of a Therapeutic Antibody Using a Monovalent Molecular Shuttle," Neuron 81:49-60.

(Continued)

*Primary Examiner* — Hong Sang
*Assistant Examiner* — Carol Ann Chase
(74) *Attorney, Agent, or Firm* — Wilson IP Law; M. Lisa Wilson

(57) ABSTRACT

The present invention relates to the fields of molecular medicine and targeted delivery of therapeutic or diagnostic agents to cells outside the vascular system and into the parenchymal tissue of organs within the body. More specifically, the present invention relates to improved TfR-binding moieties capable of crossing the blood brain barrier (BBB) and capable of carrying and releasing cargo specifically targeted to the parenchymal tissue of the brain. The present invention relates to a transcytosis selection method to obtain VNARs against mammalian blood brain barrier (BBB) receptors using phage display libraries as well as against receptors found in other directional cell barrier systems like the gastrointestinal tract and other organs. The VNARs may be used alone or as components in compositions or as conjugates that target the particular receptor transport systems for delivery of therapeutics or diagnostics to the brain (in the case of BBB receptors) or other tissues.

22 Claims, 17 Drawing Sheets

Specification includes a Sequence Listing.

(56) References Cited

FOREIGN PATENT DOCUMENTS

| WO | 2006068867 | A1 | 6/2006 | | |
|---|---|---|---|---|---|
| WO | 2007036021 | A1 | 4/2007 | | |
| WO | 2007140371 | A2 | 12/2007 | | |
| WO | 2010033913 | A1 | 3/2010 | | |
| WO | 2012075037 | A1 | 6/2012 | | |
| WO | 2013177062 | A2 | 11/2013 | | |
| WO | 2014033074 | A1 | 3/2014 | | |
| WO | 2014173959 | A2 | 10/2014 | | |
| WO | 2014189973 | A2 | 11/2014 | | |
| WO | 2015100246 | A1 | 7/2015 | | |
| WO | 2015200883 | A2 | 12/2015 | | |
| WO | 2016070959 | A1 | 5/2016 | | |
| WO | 2016081643 | A1 | 5/2016 | | |
| WO | WO-2016077840 | A2 | * 5/2016 | ........... | A61K 39/395 |
| WO | 2016094566 | A2 | 6/2016 | | |
| WO | 2016097315 | A2 | 6/2016 | | |
| WO | 2016207240 | A1 | 12/2016 | | |
| WO | 2018031424 | A1 | 2/2018 | | |
| WO | 2019089395 | A1 | 5/2019 | | |

OTHER PUBLICATIONS

Nuttall et al. (2001) "Isolation of the new antigen receptor from wobbegong sharks, and use as a scaffold for the display of protein loop libraries," Mol. Immunol. 38:313-26.

Pardridge (2002) "Drug and gene targeting to the brain with molecular Trojan horses," Nat. Rev. Drug Discov. 1:131-9.

Pardridge (2012) "Drug transport across the blood-brain barrier," J. Cereb. Blood Flow Metab. 32:1959-72.

Pardridge (2015) "Blood-brain barrier drug delivery of IgG fusion proteins with a transferrin receptor monoclonal antibody," Expert Opin. Drug Deliv. 12:207-222.

Pardridge et al. (2012) "Reengineering Biopharmaceuticals for Targeted Delivery Across the Blood-Brain Barrier," Methods Enzymol. 503:269-92.

Hasler, J., et al. (2016) "VNAR single-domain antibodies specific for BAFF inhibit B cell development by molecular mimicry." Moll Immunol 75:28-37.

Poul et al. (2000) "Selection of Tumor-Specific Internalizing Human Antibodies from Phage Libraries," J. Mol. Biol. 301:1149-61.

Rahman et al. (2016) "Immortalized endothelial cell lines for in vitro blood-brain barrier models: As systematic review." Brain Res. 1642:532-545.

Ravn et al. (2010) "By-passing in vitro screening—Next generation sequencing technologies applied to antibody display and in silico candidate selection," Nucleic Acids Res. 38:e193, 11 pages.

Regina et al. (2014) "ANG4043, a Novel Brain-Penetrant Peptide-mAb Conjugate, Is Efficacious against HER2-Positive Intracranial Tumors in Mice," Mol. Canc. Ther. 14:129-140.

Sade et al. (2010) "A Human Blood-Brain Barrier Transcytosis Assay Reveals Antibody Transcytosis Influenced by pH-Dependent Receptor Binding," PLoS One 9(4): e96340.

Shao, C-Y, et al., "Rapid isolation of IgNAR variable single-domain antibody fragments from a shark synthetic library", Molecular Immunology 44:656-665 (2007).

Shukla, A., M. Dikshit and R. C. Srimal (1995). "Nitric oxide modulates bloodbrain barrier permeability during infections with an inactivated bacterium." Neuroreport 6(12): 1629-1632.

Silvestri et al. (2014) "The extrahepatic role of TFR2 in iron homeostasis," Front. Pharmacol. 5:93, 6 pages.

Skolnick, J, and J S Fetrow. "From genes to protein structure and function: novel applications of computational approaches in the genomic era." Trends in biotechnology vol. 18,1 (2000): 34-9. doi:10.1016/s0167-7799(99)01398-0.

Srinivasan et al. (2015) "TEER measurement techniques for in vitro barrier model systems" J. Lab. Autom. 20: 107-126.

Stanfield et al. (2004). "Crystal structure of a shark single-domain antibody V region in complex with lysozyme." Science 305:1770-1773.

Stanfield, R. L., H. Dooley, P. Verdino, M. F. Flajnik and I. A. Wilson (2007). "Maturation of shark single domain (IgNAR) antibodies: evidence for induced-fit binding." J Mol Biol 367(2): 358-372.

Stanimirovic, D., et al., "Engineering and Pharmacology of Blood-Brain Barrier Permeable Bispecific Antibodies", Advances in Pharmacology, vol. 71, Chapter Ten pp. 301-335 (2014).

Triguero et al. (1990) "Capillary Depletion Method for Quantification of Blood-Brain Barrier Transport of Circulating Peptides and Plasma Proteins," J. Neurochem. 54:1882-8.

Tuma et al. (2003) "Transcytosis: Crossing Cellular Barriers," Physiol. Rev. 83:871-932.

Vajdos, Felix F et al. "Comprehensive functional maps of the antigen-binding site of an anti-ErbB2 ntibody obtained with shotgun scanning mutagenesis." Journal of molecular biology vol. 320,2 (2002): 415-28. doi:10.1016/S0022-2836(02)00264-4.

Van Rooy, I., et al., "Identification of Peptide Ligands for Targeting to the Blood-Brain Barrier" Pharmaceutical Research 27(4):673-682 (2010).

Weber et al. (2018) "Brain Shuttle Antibody for Alzheimer's Disease with Attenuated Peripheral Effector Function due to an Inverted Binding Mode" , Cell Reports 22, 149-162 Jan. 2, 2018.

Weiner et al. (2012) "Antibody-based immunotherapy of cancer: New insights, new targets," Cell 148:1081-4.

Wesolowski et al. (2009) "Single domain antibodies: promising experimental and therapeutic tools in infection and Immunity," Med. Microbiol. Immunol. 198:157-74.

White et al. (1990) "Combinations of anti-transferrin receptor monoclonal antibodies inhibit human tumor cell growth in vitro and in vivo: evidence for synergistic antiproliferative effects." Cancer Res. 50:6295-301.

White et al. (1992). "Monoclonal antibodies against defined epitopes of the human transferrin receptor cytoplasmic tail." Biochim. Biophys. Acta. 11136(1):28-34.

Williams, S. K., et al., (1980). "Isolation and Characterization of Brain Endothelial Cells: Morphology and Enzyme Activity." Journal of Neurochemistry 35(2): 374-381.

Wu, H et al. "Humanization of a murine monoclonal antibody by simultaneous optimization of framework and CDR residues." Journal of molecular biology vol. 294, 1 (1999): 151-62. doi: 10.1006/jmbi.1999.3141.

Yu et al. (2011) "Boosting Brain Uptake of a Therapeutic Antibody by Reducing Its Affinity for a Transcytosis Target," Sci. Transl. Med. 6:261ra154, 8 pages.

Cheng, Y., et al., (2004) "Structure of the human transferrin receptor-trancferrin complex." Cell 116(4):565-576.

Zielonka et al. (2014) "Structural insights and biomedical potential of IgNAR scaffolds from sharks", mAbs, vol. 7, pp. 15-25.

Pasqualini et al., "1996) Organ targeting in vivo using phage display peptide libraries," Nature 380:264-366.

Lee et al. (2000) "Targeting Rat Anti-Mouse Transferrin Receptor Monoclonal Antibodies through Blood-Brain Barrier n Mouse," J. Pharm. Exp. Ther. 292:1048-1052.

International Search Report and Written Opinion for the International Patent Application No. PCT/US2019/051114, mailed Jan. 28, 2020, 16 pages.

Abbott et al. (2010) Neurobiol. Dis. 37(1):13-25).

Ahmad et al. (2012) "scFv Antibody: Principles and Clinical Application," Clin. Dev. Immunol. 2012: 980250, 15 pages.

Alata et al. (2014) "Brain uptake of a fluorescent vector targeting the transferrin receptor: a novel application of in situ brain perfusion," Mol. Pharm 11: 243-253.

Arap et al. (1998) "Cancer Treatment by Targeted Drug Delivery to Tumor Vasculature in a Mouse Model," Science 279:377-380.

Armour et al. "Recombinant human IgG molecules lacking Fcy receptor I binding and monocyte triggering activities," Eur. J. Immunol. 29:2613-2624.

Bien-Ly et al. (2014) "Transferrin receptor (TfR) trafficking determines brain uptake of TfR antibody affinity variants," J. Exp. Med. 211:233-44.

Boje, K. M. (1996). "Inhibition of nitric oxide synthase attenuates blood-brain barrier disruptionduring experimental meningitis." Brain Res 720(1-2): 75-83.

(56) References Cited

OTHER PUBLICATIONS

Calzolari et al. (2007) "Transferrin receptor 2 is frequently expressed in human cancer cell lines," Blood Cells Mol. Dis. 39:82-91.
Casset, Florence et al. "A peptide mimetic of an anti-CD4 monoclonal antibody by rational design." Biochemical and biophysical research communications vol. 307,1 (2003): 198-205. doi:10.1016/s0006-291x(03)01131-8.
Chen et al (2011) J. Immunol. 186:3215-3225.
Couch et al. (2013) "Addressing Safety Liabilities of TfR Bispecific Antibodies That Cross the Blood-Brain Barrier," Sci. Transl. Med. 5:183ra57, 12 pages.
Crepin et al. (2010) "Development of Human Single-Chain Antibodies to the Transferrin Receptor that Effectively Antagonize the Growth of Leukemias and Lymphomas," Cancer Res. 70:5497-506.
Daniels et al. (2006) "The transferrin receptor part I: Biology and targeting with cytotoxic antibodies for the treatment of cancer." Clin. Immunol. 121:144-58.
De Vries, et al., "Effect of endotoxin on permeability of bovine cerebral endothelial cell layers in vitro," J. Pharmacol. Exp. Ther. (1996), 277(3): 1418-1423.
Demeule et al. (2014) "Conjugation of a brain-penetrant peptide with neurotensin provideds antinociceptive properties," J. Clin. Invest. 124:1199-1213.
Demogines et al. (2013). "Dual host virus arms races shape an essential housekeeping protein." PLoS Biol. 11(5):e1001571.
Diaz et al. (2002) "Structural analysis, selection, and ontogeny of the shark new antigen receptor (IgNAR): Identification of new locus preferentially expressed in early development," Immunogenetics 54:501-512.
NCBI human TfR1 isoform 1 sequence, NP_001121620.
Dooley et al. (2003) "Selection and characterization of naturally occurring single-domain (IgNAR) antibody fragments from immunized sharks by phage display," Mol. Immunol. 40:25-33.
Fennell et al. (2010) "Dissection of the IgNAR V Domain: Molecular Scanning and Orthologue Database Mining Define Novel IgNAR Hallmarks and Affinity Maturation Mechanisms," J. Mol. Biol. 400:155-170.
Forejtnikovà et al. (2010) "Transferrin receptor 2 is a component of the erythropoietin receptor complex and is required for efficient erythropoiesis," Blood 116:5357-67.
Friden et al. (1991) "Anti-transferrin receptor antibody and antibody-drug conjugates cross the blood-brain barrier," Proc. Natl. Acad. Sci. USA 88:4771-5.
Friden et al. (1996) "Characterization, Receptor Mapping and Blood-Brain Barrier Transcytosis of Antibodies to the Human Transferrin Receptorer," J. Pharm. Exp. Therap. 278:1491-98.
Nałęcz et al. (2017) Neurochem Res. 42(3):795-809.
Gerhardt et al. (1991) "The cDNA sequence and primary structure of the chicken transferrin receptor." Gene 102:249-54.
Greenberg et al. (1995). "A new antigen receptor gene family that undergoes rearrangement and extensive somatic diversification in sharks." Nature 374:168-173.
Griffiths et al. (1994) "Isolation of high affinity human antibodies directly from large synthetic repertoires," EMBO J. 13:3245-3260.
Guixer, B., et al., "Chemically synthesized peptide libraries as a new source of BBB shuttles. Use of mass spectrometry for peptide identification", Journal of Peptide Science 22:577-591 (2016).
Helguera, Gustavo et al. "An antibody recognizing the apical domain of human transferrin receptor 1 efficiently inhibits the entry of all new world hemorrhagic Fever arenaviruses." Journal of virology vol. 86,7 (2012): 4024-8. doi: 10.1128/JVI.06397-11.
Hollmann et al. (2017) "Accelerated differentiation of human induced pluripotent stem cells to blood-brain barrier endothelial cells." Fluids Barriers CNS (2017) 14:9, 13 pages.
Iezzi, M.E., et al., "Single-Domain Antibodies and the Promise of Modular Targeting in Cancer Imaging and Treatment", Frontiers in Immunology (273):1-11 (2018).
Jefferies et al. (1985) "Analysis of lymphopoietic stem cells with a monoclonal antibody to the rat transferrin receptor," Immunology 54:333-341.
Jefferies, et al, "Authentic T helper CD4 (W3/25) antigen on rat peritoneal macrophages," J.Exp.Med., vol. 162, Jul. 1985, pp. 117-127.
Jones et al. (2007) "Blood-Brain Barrier Transport of Therapeutics via Receptor-Mediation," Pharm. Res. 24:1759-71.
Jones et al., (2014) "Identifying Blood-Brain Barrier Selective Single-Chain Antibody Fragments," Biotechnopl. J. 9:664-674.
Konning et al. (2017) "Camelid and shark single antibodies: structural features and therapeutic potential." Curr. Opin. Struct. Biol. 45:10-16.
Kovaleva et al. (2014) "Shark variable new antigen receptor biologics—a novel technology platform for therapeutic drug development," Expert Opin. Biol. Ther. 14:1527-1539.
Krah et al. (2016). "Single-domain antibodies for biomedical applications." Immunopharmacol. Immunotoxicol. 38:21-28.
Lawrence CM, Ray S, Babyonyshev M, Galluser R, Borhani DW, et al. Crystal structure of the ectodomain of human transferrin receptor. Science. Oct. 22, 1999;286(5440):779-82.
Liu et al. (2014). "Thermal stability and refolding capability of shark derived single domain antibodies." Mol. Immunol. 59(2):194-199.
MacCallum, R M et al. "Antibody-antigen interactions: contact analysis and binding site topography." Journal of molecular biology vol. 262,5 (1996): 732-45. doi:10.1006/jmbi.1996.0548.
Mayhan, W. G. (1998). "Effect of lipopolysaccharide on the permeability and reactivity of the cerebral microcirculation: role of inducible nitric oxide synthase." Brain Res 792(2): 353-357.
Moos et al. (2001) "Restricted transport of anti-transferrin receptor antibody (OX26) through the blood±brain barrier in the rat," J. Neurochem. 79:119-129.
Francisco Muñoz-Martínez, Cristina Torres, Santiago Castanys, Francisco Gamarro. CDC50A plays a key role in the uptake of the anticancer drug perifosine in human carcinoma cells. Biochemical Pharmacology, Elsevier, 2010, 80 (6), pp. 793.

* cited by examiner

| CDR3 | I | A | Q | L | S | S | I | L | R | G | C | N | Y | R | K | H | D | V |
|---|---|---|---|---|---|---|---|---|---|---|---|---|---|---|---|---|---|---|
| Mutants | X | X | X | L | S | S | I | L | R | G | C | N | Y | R | K | H | D | V |
| | I | A | X | X | X | S | I | L | R | G | C | N | Y | R | K | H | D | V |
| | I | A | Q | L | X | X | X | L | R | G | C | N | Y | R | K | H | D | V |
| | I | A | Q | L | S | S | X | X | X | G | C | N | Y | R | K | H | D | V |
| | I | A | Q | L | S | S | I | L | X | X | C | X | Y | R | K | H | D | V |
| | I | A | Q | L | S | S | I | L | R | G | C | X | X | X | K | H | D | V |
| | I | A | Q | L | S | S | I | L | R | G | C | N | Y | X | X | X | D | V |

FIG. 8

TFR-SPECIFIC BINDING MOIETIES AND TRANSCYTOSIS METHOD TO SELECT VNARS THAT CROSS CELLULAR BARRIERS

This PCT application is a national stage filing under 35 U.S. § 371 of Intl. Appln. No. PCT/US2019/051114, filed Sep. 13, 2019, which claims the benefit of provisional application U.S. Ser. No. 62/731,279; filed Sep. 14, 2018, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Mar. 12, 2021, is named OSX1803-us2_SL.txt and is 152,947 bytes in size.

FIELD OF THE INVENTION

The present invention relates to a transcytosis selection method to obtain VNARs against mammalian blood brain barrier (BBB) receptors using phage display libraries as well as against receptors found in other directional cell barrier systems like the gastrointestinal tract. The VNARs may be used alone or as components in compositions or as conjugates that target the particular receptor transport systems for delivery of therapeutics or diagnostics to the brain (in the case of BBB receptors) or other tissues. In one example, the method yielded nurse shark VNARs that bind with high specificity to and functionally interact with the transferrin receptor ("TfR") as well as having the ability to cross the BBB. The invention includes compounds and compositions comprising a TfR-specific binding moiety, diagnostic and therapeutic methods of use in vitro or in vivo, e.g., to diagnose, treat and/or prevent a pathological condition, disorder or disease in which it is beneficial to deliver a heterologous biomolecule across the blood brain barrier by association with a TfR-specific VNAR binding moiety. Other uses for TfR-specific binding moieties of the invention include, e.g., regulating the interaction of iron-charged transferrin with TfR (receptor cycling or cell surface presentation), such as may be therapeutic in treatment of certain cancer cells and tumors of various tissue types.

BACKGROUND OF THE INVENTION

In addition to canonical antibodies composed of heavy and light chains, the adaptive immune systems of cartilaginous fish comprise heavy-chain only antibodies (IgNARs) devoid of light chains (Greenberg 1995). Antigen-binding is mediated exclusively by a single variable domain (VNAR), which represents the smallest immunoglobulin-based functional binding domain. VNARs combine the advantages of specificity and affinity found in conventional monoclonal antibodies with high thermal stability and solubility (Liu 2014). VNARs also possess a wide variety of loop lengths and loop structures which drastically expands the repertoire of available antigen binding sites (Könning 2017). Due to their small size and unique binding paratope, VNARs can access cryptic epitopes and catalytic clefts of enzymes (Stanfield 2004; Streltsov 2005) and likely have privileged access to novel chemical space on target molecules, which is distinct from monoclonal antibodies.

Due to such inherently favorable attributes, VNARs are being advanced for a variety of biomedical applications (Krah 2016; Könning 2017) and may ultimately represent a new class of therapeutic molecules. However, the commercial development of VNARs has been hampered by the challenges of animal immunization and lags significantly behind that camelid VHH single domains, with eight drug development programs currently in clinical trials (see, e.g., Ablynx, Inc.). To address this limitation, semi-synthetic VNAR phage display libraries (WO2015/200883) have been generated and successfully identified VNARs to a variety of potential drug targets, including the transferrin receptor 1 (TfR-1). Using a variety of in vitro and in vivo selection approaches, certain VNARs to TfR-1 were identified that can shuttle therapeutic molecules across the brain capillary endothelium, which forms an impermeable blood-brain barrier (BBB) (WO2016/077840; WO2018/031424).

VNARs to TfR-1 that function in vivo as effective BBB shuttles have remarkably different pharmacokinetic, potency and side-effect profiles than found with monoclonal antibodies to the same receptor. Multiple VNARs were able to recognize epitopes on the external, apical domain that are conserved across species and do not interfere with endogenous ligand-receptor interactions. By contrast, monoclonal antibodies reactive with the external domain of the TfR-1 are usually highly species-specific (White 1992). This domain is under selective mutational pressure by species-specific pathogens that use the receptor to gain cellular entry (Demogines 2013) and is only 77% identical between the mouse and human receptor (Gerhardt 1991). Moreover, many monoclonal antibodies to the TfR-1 extracellular domain are cytotoxic, either by perturbing transferrin transport or receptor expression (White 1990; Daniels 2006).

In the approaches cited above, cross-reactive clones were found by alternately selecting VNAR libraries on mouse and human receptors presented as recombinant protein on a cell surface or by in vivo selection in mice. For example, one TfR-1 binding VNAR clone (Clone C; also referred to as Clone 10), selected by in vivo methods in mice, crossed the BBB when formatted as an Fc fusion and reached a concentration of 5 nM in murine whole brain tissue. Clone C is the most potent shuttle to TfR-1 identified to date (WO2018/031424). The next most potent clone (Clone H; WO2018/031424; also identified as Sequence 169 in the '424 application), reached a concentration of 0.7 nM.

Both clones cross the BBB at low therapeutic doses (~2 mg/kg), are rapidly taken up into the brain (within 1 hour), continue to accumulate over several days and slowly decline over the next week after a single IV injection. These profiles markedly contrast with other BBB shuttles to TFR-1, which are rapidly cleared by the liver (Boado 2009; Niewoehner 2014) or require very high doses (e.g., 50 mg/kg, Genentech; Yu 2014).

Variants of Clone C and Clone H were prepared by a restricted random mutagenesis strategy of the VNAR CDR3 domain and several were capable of reaching higher concentrations in the brain than its corresponding parent (U.S. Ser. No. 62/580,934, filed Nov. 2, 2017 and U.S Ser. No. 62/624,107, filed Jan. 30, 2018, respectively, and the priority applications of WO2019/089395, published May 9, 2019). Nonetheless, the need remains for additional molecules that selectively deliver compounds such as biomolecules (e.g., therapeutics and diagnostics) across membrane systems in mammalian subject, as found in various organs, tumors or the BBB. Moreover, it would be advantageous to have new selective TfR-specific binding compounds, especially ones having one or more advantageous biological properties with therapeutic and/or diagnostic benefit over current anti-TfR antibodies and other regulators of iron transport systems.

The present invention addresses these needs by employing a different approach to obtain novel membrane-crossing VNARs directly against the species of interest, particularly for human targets, by first biopanning VNAR phage display libraries for binding to a target human receptor and then using that enriched phage library in a step of in vitro transcytosis selection with human capillary endothelial cells to screen for phage transported to the basolateral side of the cells. Such clones may also exhibit species cross reactivity, and as found herein, many clones obtained were capable of binding both the human and mouse receptor and efficiently crossing the BBB in vivo. This selection approach provides a general method to select for VNARs that cross the BBB via functional interaction with BBB apical membrane receptors as well as apical membrane receptors of other tissues and organs.

SUMMARY OF THE INVENTION

The present invention provides new TfR-specific binding moieties which were obtained by a method of in vitro transcytosis, followed in some cases by further mutagenesis to improve the activity of those binding moieties as potential therapeutics for delivering therapeutic or diagnostic cargos to the brain. Additionally, the method of in vitro transcytosis of the invention uses phage display libraries to identify polypeptides capable of traversing mammalian cellular barriers, and is especially useful for finding polypeptides that cross the human blood-brain barrier.

Accordingly, one aspect of the invention provides an isolated TfR-specific binding moiety comprising a VNAR domain capable of specifically binding to human TfR-1 without substantially interfering with transferrin binding to and/or transport by human TfR-1, wherein said VNAR domain has an amino acid sequence of any one of clones 1-31 in Table 1. In certain embodiments, the TfR-specific binding moiety is capable of uptake across the blood brain barrier and has a VNAR domain with an amino acid sequence of Clones 5, 8, 10 or 22 of Table 1. In some embodiments, the VNAR domain has an amino acid sequence of any one of clones 32-85 in Table 1. In some embodiments, the VNAR domain is a Type I isoform. In some embodiments, the VNAR domain is a Type II isoform.

In other embodiments, the isolated TfR-specific binding moiety comprises a VNAR represented by the formula, from N to C terminus,

FW1-CDR1-FW2-HV2-FW2'-HV4-FW3-CDR3-FW4, wherein
(a) FW1 is ARVDQTPQTITKETGESLTINCVLR (SEQ ID NO. 1) or PRVDQTPQTITKETGESLTINCVLR (SEQ ID NO. 2),
(b) CDR1 is DSNCALP (SEQ ID NO. 3),
(c) FW2-HV2-FW2'-HV4-FW3 is STYWYRKKSGST-NEESISKGGRYVETVNSGSKSFSLRINDLTVED-SGTYRCKV (SEQ ID NO. 4),
(d) CDR3 is represented by formula $X_1X_2X_3LX_4X_5X_6LRGCNYRKHDV$ (SEQ ID NO. 5), wherein
$X_1$ is F, I or R,
$X_2$ is A or W,
$X_3$ is P, Q, or R,
$X_4$ is G or S,
$X_5$ is S or W,
and
$X_6$ is I or W; and
(e) FW4 is YGDGTAVTVNA (SEQ ID NO. 6),
wherein the moiety is specific for human TfR-1 and capable of crossing the blood brain barrier.

In some embodiments, the VNAR domain of a TfR-specific binding moiety of the invention comprises the VNAR domain of Clone 8, 8.5, 8.8 or 8.12.

To obtain a TfR-specific binding moiety that crosses the BBB, the moiety can be formatted as an Fc fusion protein such that when injected into one or more mice at 1.875 mg/kg, the fusion exhibits a concentration in murine brain homogenates of at least about 0.4 nM. Hence, these TfR-specific binding moieties of the invention are capable of penetrating the brain when injected into mice at 1.875 mg/kg, as described herein, and accumulating in murine brain homogenates at concentrations ranging from at least about 0.4 nM to about 25 nM, from about 0.5 nM to about 25 nM, or from about 0.7 nM to about 20 nM.

In some embodiments, the TfR-specific binding moiety has a half maximal effective concentration (EC50) for binding human TfR-1 of less than or equal 30 nM.

In accordance with the invention, the TfR-specific binding moieties of the invention can be formulated as conjugates, including but not limited to, conjugates which comprise a heterologous agent which is a diagnostic or therapeutic agent. In some embodiments, the conjugate comprises one or more of the following agents: a small molecule, a DNA, RNA, or hybrid DNA-RNA, a traceable marker such as a fluorescent or phosphorescent molecule, a radionuclide or other radioactive agent, an antibody, single chain variable domain, immunoglobulin fragment, variant or fusion, a small molecule diagnostic or therapeutic.

Further aspects of the invention are directed to nucleic acids encoding the TfR-specific binding moieties or conjugates of the invention, as well as vectors and host cells containing those nucleic acids and vectors.

Some aspects of the invention provide pharmaceutical compositions comprising a TfR-specific binding moiety of the invention or a conjugate thereof.

The instant invention also provides methods of medical treatment, including a method to administer a therapeutically-effective amount of a pharmaceutical composition of the invention to deliver a diagnostic or therapeutic agent to the brain of a mammalian subject in need thereof.

Additional methods of the invention are directed to targeting delivery of a payload to brain parenchymal tissue in a mammal by administering compound or composition comprising the payload in physical association with or operably linked to a TfR-specific binding moiety or conjugate of the invention.

Further aspects of the invention relate to kits for detecting or quantifying TfR-1 in a sample which comprises at least one TfR-specific binding moiety or conjugate of the invention.

Yet other aspects relate to a compound for use as a diagnostic or therapeutic agent in a subject, where the compound comprises a diagnostic or therapeutic agent operably linked to a TfR-specific binding moiety of the invention, and wherein the TfR-specific binding moiety, when formatted as Fc fusion protein and dosed at 1.875 mg/kg IV is capable of achieving at least about 0.5 nM in homogenized mouse brain tissue, and upon binding to human TfR-1 in a cell membrane, is endocytosed to thereby deliver said diagnostic or therapeutic agent across the cell membrane. In some embodiments, the concentration of fusion protein ranges from at least about 0.4 nM to about 25 nM, from about 0.5 nM to about 25 nM, or from about 0.7 nM to about 20 nM. In some embodiments, the operable linkage dissociates after endocytosis to release said diagnostic or therapeutic agent into said cell. In some embodiments, the cell membrane is part of the blood brain barrier or the GI tract.

Another aspect of the invention provides methods of delivering a therapeutic or diagnostic molecule across the blood brain barrier which comprises administering a TfR-specific binding moiety of the invention, wherein said therapeutic molecule is conjugated to said moiety, to a subject for a time and in an amount effective to treat or diagnose a CNS disease or condition.

Another aspect of the invention provides methods of delivering a therapeutic or diagnostic molecule to the gastrointestinal (GI) tract which comprises administering a TfR-specific binding moiety of the invention, wherein said therapeutic molecule is conjugated to said moiety, to a subject for a time and in an amount effective to treat or diagnose a GI disease or condition.

Further methods of the invention are directed to a method of treatment which comprises administering to a subject in need thereof a compound or composition comprising a TfR-specific binding moiety of the invention. In some embodiments, the disease or condition is ameliorated upon transport of a heterologous molecule across a cell membrane of a TfR-positive cell, wherein said heterologous molecule comprises or is associated with (e.g., covalently or noncovalently) a TfR-specific binding moiety of the invention. In some embodiments, the TfR-specific binding moiety is internalized by a TfR in a cell membrane associated with the blood brain barrier or the gastrointestinal (GI) tract. In some embodiments, the disease or condition is a central nervous system disease or condition. In some embodiments, the disease or condition is cancer, particularly cancers wherein the cancerous cells express a higher level of TfR relative to the equivalent or similar non-cancerous cells.

Yet another aspect of the invention relates to methods of identifying, quantifying or localizing a TfR-containing biological sample or cell which comprises contacting a test sample in vitro or in vivo with a TfR-specific binding moiety of the invention, or a conjugate thereof, and directly or indirectly measuring the TfR-specific binding in or to said sample.

Another embodiment of the invention is directed to targeting delivery of a heterologous molecule to a TfR-expressing cell by delivering a TfR-specific conjugate of the invention to the target. Another embodiment of the invention is directed a method of increasing the oral bioavailability of a drug by associating the drug with a TfR-specific-binding moiety of the invention.

The instant invention provides in vitro transcytosis methods using phage display libraries. In one embodiment, the method is directed to identifying polypeptides capable of traversing a mammalian cellular barrier which comprises (a) culturing mammalian polarized cells for a time and under conditions on a permeable support in the upper compartment of a two-compartment cell culture system to obtain a monolayer of cells with a paracellular permeability and transendothelial electrical resistance (TEER) sufficient to indicate the presence of tight junctions; (b) delivering a phage display library encoding the polypeptides into the upper compartment of said system for a time sufficient for transport of one or more phage in the library to the lower compartment of said system; and (c) collecting the media from the lower compartment and recovering those phage which transversed the cellular barrier to produce an enriched phage library. The enrichment step can be repeated from zero to several times to obtain a final enriched phage display library. The final library is then screened to detect one or more of the polypeptides capable of traversing the cellular barrier.

The mammalian cellular barrier for use in this method include blood-brain barriers formed by capillary endothelial cells, gastrointestinal tract barriers formed by gut epithelial cells intestine (including M cells and enterocytes), placental cells, bronchial epithelial cells and other vascular endothelial cell barriers (non-brain). Hence, in one embodiment, the mammalian cellular barrier can be the blood brain barrier of a mammal and preferably a human blood brain barrier.

In some embodiments, the polarized cells are mammalian endothelial cells, and preferably, human endothelial cells. In some embodiments, the polarized cells are primary cells, immortalized cells or induced human pluripotent stem cells (iPSCs) which have been differentiated into brain microvascular endothelial cells. In a preferred embodiment, the polarized cells are hCMEC/D3 cells.

In some embodiments, the phage display library has been enriched by pre-selection one or more times against polypeptides capable of binding to a brain receptor or transporter. Additionally, the phage display library can be treated to reduce endotoxin levels by at least 10-fold relative to a non-treated phage display library. Further, in some embodiments, the phage display library comprises nurse shark VNAR polypeptides capable of binding to a brain receptor or transporter, including but not limited to a brain receptor or transporter selected from the group consisting of TMEM30a, CD98hc, basign, transferrin receptor-1 (TfR-1), insulin receptor, insulin-like growth factor receptor (IGF receptor), low density lipoprotein receptor-related protein 8 (LRP8), low density lipoprotein receptor-related protein 1 (LRPT), glucose transporter 1 (Glut1) and heparin-binding epidermal growth factor-like growth factor (HB-EGF).

BRIEF DESCRIPTION OF THE DRAWINGS

FIG. 8. Mutagenesis Strategy for CDR3 of Clone 8. Seven phage libraries based on Clone 8 CDR3 were designed. In each library, three adjacent residues were randomized with one residue overlap between libraries. The cysteine at position 11 was maintained to retain the VNAR Type 2 isoform structure and the invariable DV di-peptide at the C-terminus was unchanged. "X" denotes any amino acid except for cysteine.

DETAILED DESCRIPTION OF THE INVENTION

Figure 1:
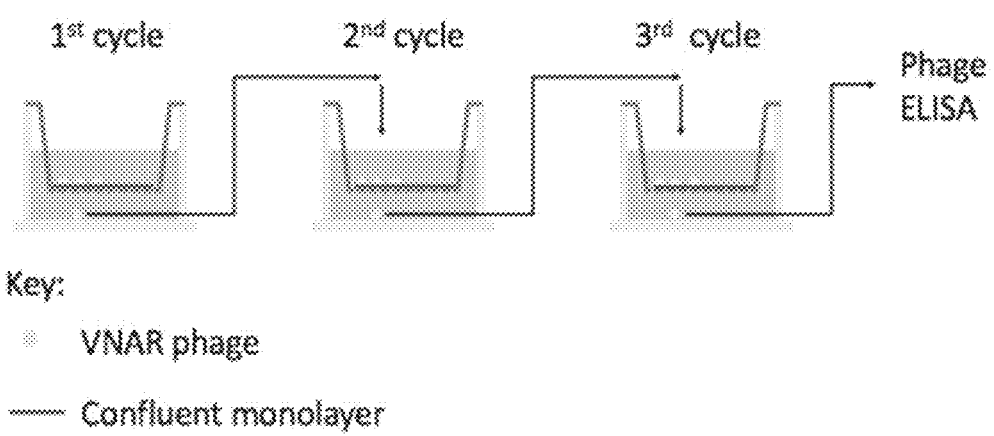
FIG. 1. Transcytosis assay design. This drawing depicts three cycles of the in vitro phenotypic phage selection with monolayers of hCMEC/D3 cells in Transwell® chambers. A VNAR phage display library (enriched by preselection against a target receptor protein) is added to confluent cells in the apical chamber of the Transwell and transported phage are collected from the basolateral chamber. After phage amplification and endotoxin removal, the cycle is repeated two more times. The final phage collection is spread onto agar plates overnight and individual colonies analyzed by phage ELISA against the target receptor.

In order that the present invention may be more readily understood, certain terms are defined below. Additional definitions may be found within the detailed description of the invention.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., cows, pigs), companion animals (e.g., dogs, cats) and rodents (e.g., mice and rats).

The term "non-human mammal" means a mammal which is not a human and includes, but is not limited to, a mouse, rat, rabbit, pig, cow, sheep, goat, dog, primate, or other non-human mammals typically used in research. As used herein, "mammals" includes the foregoing non-human mammals and humans.

As used herein, "treating" or "treatment" and grammatical variants thereof refer to an approach for obtaining beneficial or desired clinical results. The term may refer to slowing the onset or rate of development of a condition, disorder or disease, reducing or alleviating symptoms associated with it, generating a complete or partial regression of the condition, or some combination of any of the above. For the purposes of this invention, beneficial or desired clinical results include, but are not limited to, reduction or alleviation of symptoms, diminishment of extent of disease, stabilization (i.e., not worsening) of state of disease, delay or slowing of disease progression, amelioration or palliation of the disease state, and remission (whether partial or total), whether detectable or undetectable. "Treatment" can also mean prolonging survival relative to expected survival time if not receiving treatment. A subject (e.g., a human) in need of treatment may thus be a subject already afflicted with the disease or disorder in question. The term "treatment" includes inhibition or reduction of an increase in severity of a pathological state or symptoms relative to the absence of treatment, and is not necessarily meant to imply complete cessation of the relevant disease, disorder or condition.

As used herein, the terms "preventing" and grammatical variants thereof refer to an approach for preventing the development of, or altering the pathology of, a condition, disease or disorder. Accordingly, "prevention" may refer to prophylactic or preventive measures. For the purposes of this invention, beneficial or desired clinical results include, but are not limited to, prevention or slowing of symptoms, progression or development of a disease, whether detectable or undetectable. A subject (e.g., a human) in need of prevention may thus be a subject not yet afflicted with the disease or disorder in question. The term "prevention" includes slowing the onset of disease relative to the absence of treatment, and is not necessarily meant to imply permanent prevention of the relevant disease, disorder or condition. Thus "preventing" or "prevention" of a condition may in certain contexts refer to reducing the risk of developing the condition, or preventing or delaying the development of symptoms associated with the condition.

As used herein, an "effective amount," "therapeutically-effective amount" or "effective dose" is an amount of a composition (e.g., a therapeutic composition or agent) that produces at least one desired therapeutic effect in a subject, such as preventing or treating a target condition or beneficially alleviating a symptom associated with the condition.

A physiologically-acceptable solution for use in an amount and for a time sufficient to effectively reduce a circulating concentration of the plurality of polypeptides is also referred to herein as a perfusate. The amount of perfusate and time of perfusion depends on the non-human mammal and can be readily determined by those of skill in the art. For example, with a mouse, using a volume of perfusate approximately 10× the blood volume of the mouse is effective at reducing the circulating concentration of polypeptides. Likewise, any volume of perfusate that reduces the circulating concentration of the plurality of polypeptides by about 10%, 25%, 50% or more (relative to the theoretical concentration of the plurality of polypeptides) being delivered is considered effective at reducing the circulating concentration of that plurality.

As used herein, the term "TfR," "TfR1" or "TfR-1" refers to a mammalian transferrin receptor-1 (in context as a protein or a nucleic acid), unless the context indicates that it refers specifically to human TfR-1 (see, e.g., UniProt P02786 TFR1_Human) or mouse TfR-1.

Phage Display Transcytosis

Transcytosis involves the selective movement of a macromolecular cargo from one side of a cell to the other. This process allows large (and small) molecules to move from one environment to another without altering the compositions of those environments (Tuma 2003). A variety of in vitro transcytosis models are known in the art, but none have used phage display libraries as a source of novel binding molecules to screen for polypeptides that can bind to apical membrane receptors, be transported through the cell across the basolateral membranes and released into the environment on the basolateral side. This invention now provides such a method using VNAR phage display libraries.

Accordingly, this invention provides a method to identify polypeptides capable of traversing mammalian cell barriers. Such barriers include blood-brain barriers formed by capillary endothelial cells, gastrointestinal tract barriers formed by gut epithelial cells intestine (including M cells and enterocytes), placental cells, bronchial epithelial cells and other vascular endothelial cell barriers (non-brain). The cells thus have polarity with respect to the transfer of proteins (or other molecules) from the apical side to the basolateral sides, and are also referred to as polarized cells or bipolar cells. This method is particularly useful with human cell lines as it allows selection of molecules that bind to human receptors and are capable of traversing human cell barriers.

Hence, the method comprises culturing mammalian polarized cells on a permeable support in an upper compartment of a two-compartment cell culture system for a time and under conditions to produce a confluent monolayer of cells with a paracellular permeability and transendothelial electrical resistance (TEER) sufficient to indicate the presence of tight junctions, i.e., the formation of a transport barrier. Once the barrier is formed, a phage display library encoding the potential binding polypeptides is delivered into the upper compartment to interact with and bind to the target receptor on the apical membrane. After time for transcytosis across the cell and into the lower compartment of the system to occur, phage can be recovered by collecting the media from the lower compartment, and amplifying the phage to obtain an enriched phage library. This cycle can, optionally, be repeated to further enrich the library against the target receptor. After the final cycle, individual polypeptide binders are detected in the final enriched phage display library to identify those phage which encode a polypeptide capable of traversing the cellular barrier.

Various methods can be used to determine whether the phage bind the target receptor, particularly when selecting for binders to a specific target. For example, for a predetermined target, the phage library can be enriched for binders to target by one or more rounds of selection on the purified target protein (in, for example, a phage ELISA). Those phage are then used in the transcytosis method of the invention, and after the last transcytosis cycle, the collected phage are plated to obtain individual colonies which can then be tested for binding to the original target.

For conducting the transcytosis method of the invention, those of skill in the art can determine the growing parameters of the cells, such as which media, how long to grow to confluence and the like. For example, the media to be used will depend on the cells being grown and can be readily determined by those of skill in the art.

The substrate on which to grow cells (e.g., filters such as polycarbonate, polyester, PTFE, PET, polystyrene, cellulose and the like) and whether or not to coat the substrate (with, e.g., collagen or other substance for cell adherence), can be readily determined by one of skill in the art based on the selected polarized cells being grown on the substrate.

The pore size of the substrate or filter determines the permeability of the support and should be sufficiently small to prevent cells from migrating through the filter while large enough to allow the phage to pass through to the basolateral chamber. Typically, using pore diameters of less than or equal to 1 μm is sufficient in this regard and can be determined by those of skill in the art.

When seeding the cells on the supports or filters, it is desirable to use a cell seeding density, that can achieve a homogenous, confluent monolayer synchronously across entire filter. Again, the seeding density depends on the cells being used as well as on growth rates, growth conditions and the tendency of the cells to differentiate (or not) under a given set of conditions. Those of skill in the art can readily determine the needed seeding density for particular cell lines.

After seeding, cells are grown until they reach confluence and form a cellular barrier. Various methods are known in the art to assess the integrity of the cellular monolayer that forms the barrier. For example, transepithelial electrical resistance (TEER) can be measured (see, e.g., Srinivasan et al. 2015). When using TEER measurements, cells are grown until the TEER measurement reaches a value indicative of the presence of formation of tight junctions for a given cell line, and such values may vary based on the cell line. Under the conditions described in Example 1, a TEER of 20 Ω·cm2 indicates formation of an endothelial barrier by hCMEC/D3 cells. Another way to assess monolayer integrity is to measure paracellular permeability using large molecules like inulin or FITC-dextran. Methods of conducting such assays are well known in the art and can be determined for any given cell line. Again, as an example, for hCMEC/D3 cells grown as described in Example 1, the cells are confluent when the permeability of 40 kDal FITC-dextran decreases to ~0.2×10$^{-3}$ cm/min.

The cell lines that can be used in the transcytosis method of the present invention depend on the receptor and tissue being targeted and include cell lines that form blood-brain barriers, gastrointestinal tract (including M cells and enterocytes), placental barriers, pulmonary barriers and other vascular endothelial cell barriers (non-brain).

Examples of endothelial cell lines representative of the BBB, include but are not limited to, the cell lines BB19, EA.hy926, ECV304, HBMEC, HBMEC/ciβ, HBMVEC, HCEC, hCMEC/D3, HEK 293, HUVEC, HUVEC-304, iHBMEC, IHEC, NKIM-6, THBMEC, TY08 and TY10 for binders to human receptors; the cell lines bEnd.3, bEnd.5, bEnd.WT, cEND, cerebEND, CRL-2583, MBEC-4, luEnd.PECAM-1.1 and TM-BBB for binders to mouse receptors; the cell lines CEC, CR3, GP8, GPNT, RBCEC4, RBE4, RBEC1 and TR-BBB for binders to rat receptors; the cell line BBEC-117 for binders to bovine receptors; and the cell line PBMEC/C1-2 for binders to porcine receptors (Rahman 2016). Preferred cell lines are the human microvascular endothelial cell line hCMEC/D3, rat endothelial cell line RBE4 and mouse brain microvascular cell line bEnd.3.

Primary cell lines and induced pluripotent stem cells (iPSCs) can also be used in the transcytosis method of the invention. For example, human iPSCs can be cultured under conditions leading to their differentiation into human brain microvascular endothelial cells (BMECs) and seeded onto a permeable support for formation of a confluent monolayer (Hollmann 2017).

Table 4 of Tuma and Hubbard list a number of in vitro cell systems that can be adapted for use in the present invention.

Examples of receptors and receptor-mediated transport systems which can be used according to the methods of the invention include but are not limited to, and identified in the following list by either the ligand or receptor (or both): transferrin, transferrin receptor-1, transferrin receptor-2, melanotransferrin, lactoferrin, apolipoprotein E receptor 2, LDL-receptor-related protein 1 and 2, receptor for advanced glycosylation end-products, immunoglobulin G, insulin, leptin, tumor necrosis factors, epidermal growth factor, heparin-binding epidermal growth factor-like growth factor (diphtheria toxin receptor), and leukemia inhibitory factor (LIF) (see, e.g., Abbott 2010).

Examples of solute carrier systems which can be used according to methods of the invention include but are not limited to: GLUT1, SGLT1, SMITHMIT/GLUT13, CAT1, CAT3, LAT1, LAT2, SNAT2, SNAT3, SNAT 5, ASCT1, ASCT2, EAAT1, EAAT2, EAAT3, GLYT, TAUT, ENT1, ENT2, CNT1, CNT2, CNT3, MCT1, MCT2, MCT8, OAT2, OAT3, OATPB, OATP1A4, OATP1C1. OCT2, OCT3, OCTN2, PMAT, CTL1 (id.) Examples of ABC transporter systems include but are not limited to: ABCA2, ABCB1, ABCC1, ABCC2, ABCC3, ABCC4, ABCC5 and ABCG2. The identification and enrichment methods of the invention may also be applied to numerous examples of transporters for neurotransmitters and their precursors (see e.g., Nałęcz 2017, directed to SLC families involved in blood-brain barrier transport of a variety of sugars, amino acids, neurotransmitters and precursors and organic ions).

Additional membrane receptors that can be targeted include: TMEM30a, also referred to as transmembrane protein 30A, cdc50a, FLJ10856, or C6orf67 (Chen 2011; Munoz-Martinez 2010), insulin receptor, insulin-like growth factor receptor (IGF receptor), low density lipoprotein receptor-related protein 8 (LRP8), low density lipoprotein receptor-related protein 1 (LRPT), glucose transporter 1 (Glut1) and heparin-binding epidermal growth factor-like growth factor (HB-EGF) as well as basigin and CD98 heavy chain (CD989hc) (see, e.g., WO2013/177062; WO2012/075037)

Phage display libraries are known in the art and can be prepared to encode antibodies or other molecules that can bind to target receptors. For example, the semi-synthetic VNAR libraries described in WO15/200883 can be used in the present invention. In a preferred embodiment, endotoxin is significantly reduced (at least a ten-fold reduction) or removed from the phage preparations before applying the phage to the confluent monolayers. Endotoxin can be reduced and/or removed by treatment with Triton X-114 or other methods known in the art.

Polypeptide Sequences and Compounds Comprising a TfR Specific VNAR

The present invention provides human TfR-1-specific binding moieties obtained by an in vitro transcytosis selection on confluent, human monolayers of cells that mimic the human blood-brain barrier (BBB). Using the methods described above, after three cycles of enrichment using the OsX-3 and OsX-4 phage display libraries (WO2015/200883) that had been pre-enriched for binding to recombinant human TfR-1, individual phage were analyzed by sequencing and by phage ELISA for binding to recombinant mouse and human TfR-1. These phage yielded 85 TfR-1 binding VNARs with unique sequences (Table 1). Of these, Clones 1-31 showed significant binding to both mouse and human TfR-1.

Accordingly, one aspect of the present invention is directed to an isolated TfR-specific binding moiety comprising a VNAR domain capable of specifically binding to human TfR-1 without substantially interfering with transferrin binding to and/or transport by human TfR-1, wherein said VNAR domain has an amino acid sequence of any one of clones 1-31 in Table 1. In some embodiments, the TfR-specific binding moiety is further able to bind to mouse TfR-1.

In some embodiments, the TfR-specific binding moiety of the invention is capable of uptake across the BBB. Examples of such VNAR domains are Clones 5, 8, 10 and 22 whose amino acids sequences are provided in Table 1.

The VNAR domain amino acid sequence for Clone 8 is:

(SEQ ID NO. 7)
ARVDQTPQTITKETGESLTINCVLR*DSNCALP*STYWYRKKSGSTNEESISK

GGRYVETVNSGS KSFSLRINDLTVEDSGTYRCKVIAQLSSILRGCNYRKH

DVYGDGTAVTVNA.

The CDR1 domain is bolded, underlined and italicized; the CDR3 domain is bolded and underlined.

To improve BBB shuttling function of Clone 8, its CDR3 region was subjected to a restricted randomization process. Seven new phage libraries were prepared based on the CDR3 with three subsequent residues randomized in each library and with the offset of two residues (FIG. 8). The Clone 8 VNAR domains are referred to herein as "Clone 8 variants" or by specific numbers in the format "Clone 8.xx" (Table 2). The specific Clone 8 variants shown to cross the BBB as well as or better than Clone 8 are Clone 8.5, 8.8 and 8.12, with Clone 8.5, formatted as a VNAR fused to the human Fc domain (CH2 and CH3), being the most potent known TfR-binding moiety found to date. The Clone 8.5 VNAR-Fc fusion achieved receptor saturation in vivo in mice at a dose of <50 nmol/kg (3.75 mg/kg) and sustained brain concentration of >10 nM for more than 6 days after a single intravenous dose of <12.5 nmol/kg (0.9375 mg/kg) in mice.

Hence, in accordance with the invention, certain embodiments of the isolated TfR-specific binding moiety comprise a VNAR domain capable of specifically binding to human TfR-1 without substantially interfering with transferrin binding to and/or transport by human TfR-1 and to crossing the blood brain barrier, wherein said VNAR domain as a sequence of (SEQ ID NO. 8)
ARVDQTPQTITKETGESLTINCVLR*DSNCALP*STYWYRKKSGSTNEESISK

GGRYVETVNSGS KSFSLRINDLTVEDSGTYRCKV-CDR3-YGDGTAVTVN

A
or (SEQ ID NO. 9)
PRVDQTPQTITKETGESLTINCVLR*DSNCALP*STYWYRKKSGSTNEESISK

GGRYVETVNSGS KSFSLRINDLTVEDSGTYRCKV-CDR3-YGDGTAVTVN

A, wherein CDR3 has a peptide sequence of the CDR3 of Clone 8, 8.5, 8.8 or 8.12 (see, Table 2) The amino acid sequences of these CDR3s are IAQLSSILRGCNYRKHDV (Clone 8; SEQ ID NO.10), IAQLGWWLRGCNYRKHDV (Clone 8.5; SEQ ID NO.11), FAPLSSILRGCNYRKHDV (Clone 8.8; SEQ ID NO. 12) and RWRLSSILRGCNYRKHDV (Clone 8.12; SEQ ID NO. 13).

In other embodiments, the isolated TfR-specific binding moiety comprises a VNAR scaffold represented by the formula, from N to C terminus,

FW1-CDR1-FW2-HV2-FW2'-HV4-FW3-CDR3-FW4, wherein
(a) FW1 is ARVDQTPQTITKETGESLTINCVLR (SEQ ID NO. 1) or PRVDQTPQTITKETGESLTINCVLR (SEQ ID NO. 2),
(b) CDR1 is DSNCALP (SEQ ID NO. 3),
(c) FW2-HV2-FW2'-HV4-FW3 is STYWYRKKSGSTNEESISKGGRYVETVNSGSKSFSLRINDLTVEDSGTYRCKV (SEQ ID NO 4),
(d) CDR3 is represented by formula $X_1X_2X_3LX_4X_5X_6$LRGCNYRKHDV (SEQ ID NO. 5), wherein
$X_1$ is F, I or R,
$X_2$ is A or W,
$X_3$ is P, Q, or R,
$X_4$ is G or S,
$X_5$ is S or W, and
$X_6$ is I or W; and
(e) FW4 is YGDGTAVTVNA (SEQ ID NO. 6),
wherein the moiety is specific for human TfR-1 and capable of crossing the blood brain barrier.

Those TfR-specific binding moieties of the invention which cross the BBB as well as or better than Clone 8 are capable of specific binding to human TfR-1 and mouse TfR-1, and when formatted as Fc fusion proteins and injected into mice at 25 nmol/kg (1.875 mg/kg) as described in the Examples below, these TfR-specific binding moieties of the invention accumulate in murine brain homogenates at concentrations ranging from at least 0.4 nM to about 25 nM, from about 0.5 nM to about 25 nM, or from about 0.7 nM to about 20 nM.

As used herein, a "VNAR scaffold" has the general structure, from N to C terminus, given by the formula FW1-CDR1-FW2-HV2-FW2'-HV4-FW3-CDR3-FW4, wherein the FWs are framework regions, CDRs are complementarity determining regions and HVs are hypervariable regions that form the variable domain of a shark IgNAR ("VNAR"). VNAR scaffolds of the invention are the FW1, FW2, FW2', FW3 and FW4 regions have naturally occurring VNAR sequences or altered VNAR sequences with amino acid substitutions, insertions or deletions (typically, from 1, 2, 3, 4, 5, 1-3, 1-5 or 1-10, but not limited to, no more than 10 amino acids a changes) provided that such changes maintain the overall primary and tertiary structure of the VNAR. Those of skill in the art can identify and ascertain the effect of such alterations. In addition, the FW1, FW2, FW2', FW3 and FW4 regions can have any of the sequences for those regions as shown in Table 1.

As used herein a "VNAR domain" means a naturally-occurring VNAR, an altered VNAR (such as those described herein), a variable domain of a camelid antibody (known as a VHH) or the variable domain of any single chain antibody, whether such domains are naturally occurring, selected or engineered.

The VNARs, the VNAR scaffolds and the VNAR domains of the invention can optionally have a His-Tag (or other convenient tag for purification purposes). In some cases, such tags are removable.

In yet another aspect of the invention, any of the TfR-specific binding moieties can form all or part of the variable domain of a single variable domain antibody, a bi- or tri-functional VNAR, a conventional antibody, or any fragment or fusion protein of said antibody as well as variable domains with antibody-like backbones.

Examples of single variable domain antibodies include, but are not limited to, a shark or other cartilaginous fish antibodies, camelid antibodies and nobodies. Examples conventional antibodies include, but are not limited to, immunoglobins having both heavy and light chains, such as IgM's, IgA's, IgG's, IgE's, single chain Fv's, Fab fragments, or any fragment or fusion protein of such antibodies or fragments.

Non-limiting examples of antibody-like backbones that may be used according to the invention include monospecific and bispecific such as multimerizing scFv fragments (diabodies, triabodies, tetrabodies), disulfide stabilized antibody variable (Fv) fragments, disulfide stabilized antigen-binding (Fab) fragments consisting of the $V_L$, $V_H$, $C_L$ and $C_H1$ domains, bivalent F(ab')2 fragments, Fd fragments consisting of the heavy chain and $C_H1$ domains, dimeric $C_H2$ domain fragments ($C_H2D$), Fc antigen binding domains (Fcabs), single chain Fv-$C_H3$ minibodies, bispecific minibodies, isolated complementary determining region 3 (CDR3) fragments, constrained FR3-CDR3-FR4 polypeptides, SMIP domains, and any genetically manipulated counterparts of the foregoing that retain TfR-1 binding function (see e.g., Weiner L, Cell 148: 1081-4 (2012); Ahmad Z et al., Clin Dev Immunol 2012: 980250 (2012) for reviews).

Therefore, in one aspect, the invention provides a TfR-selective compound comprising or consisting essentially of a VNAR derived TfR-specific binding moiety of the invention which binds selectively to a TfR polypeptide, preferably to human TfR (see e.g., UniProt P02786 TFR1_Human) or to a TfR, e.g., human TfR epitope-containing polypeptide.

In certain embodiments, a TfR specific binding moiety of the invention binds to a transferrin receptor (TfR) on the membrane of a mammalian cell and TfR specific binding mediates transport of the TfR specific binding moiety and at least one associated heterologous molecule across the cell membrane. Any TfR-positive cell or cell type (i.e., one with the transferrin receptor localized at the cell membrane) may thus be used to target delivery of heterologous molecules across its membrane by association (e.g., a complex or conjugate) with a TfR specific binding moiety of the invention. As described in more detail below, heterologous molecules may be selected from an enormously wide variety of agents, limited only by the target cell requiring a cell surface TfR which can internalize upon binding.

In certain embodiments of the invention, the cell membrane is part of the blood brain barrier (BBB) and TfR-mediated transport across the BBB of a heterologous molecule may be accomplished. In certain other embodiments of the invention, the cell membrane is part of the GI tract and TfR-mediated transport of a heterologous molecule may be accomplished, enabling oral drug delivery routes, especially advantageous for previously non-orally bioavailable drugs or molecules for therapeutics and/or diagnostics.

Associated heterologous molecules which may be used in conjunction with any one of the above embodiments may comprise, e.g., one or more biologically active molecules and/or imaging agents. Exemplary biologically active molecules which may be transported into a TfR-positive cell in association with a TfR-specific binding moiety of the invention include, e.g., toxins for targeted TfR-positive cell death (useful e.g., in certain hyperproliferative diseases or disorders such as cancers or aberrant proliferative conditions). Other exemplary biologically active molecules which may be transported in association with a TfR specific binding moiety include, e.g., polypeptides, such as an antibody or antibody fragment; a therapeutic peptide such as a hormone, cytokine, growth factor, enzyme, antigen or antigenic peptide, transcription factor, or any functional domain thereof. Other exemplary biologically active molecules which may be transported into a TfR-positive cell in association with a TfR specific binding moiety include, e.g., nucleic acid molecules, such as an oligonucleotide (e.g., single, double or more stranded RNA and/or DNA molecules, and analogs and derivatives thereof); small regulatory RNA such as shRNA, miRNA, siRNA and the like; and a plasmid or fragment thereof.

Exemplary polypeptides which may be therapeutically beneficial when administered as a heterologous molecule for TfR-mediated transport across the BBB or other TfR-containing cell membrane include but are not limited to: a brain derived neurotrophic factor (BDNF), a bone morphogenic protein (e.g., BMP-1 through BMP-7, BMP8a, BMP8b, BMP10 and BMP15), a ciliary neurotrophic factor (CNF), an epidermal growth factor (EGF), erythropoietin, a fibroblast growth factor (FGF), a glial derived neurotrophic factor (GDNF), a hepatocyte growth factor, an interleukin (e.g., IL-1, IL-4, IL-6, IL-10, IL-12, IL-13, IL-15, IL-17), a nerve growth factor (NGF), a neurotrophin (e.g., NT-3 and NT-4/5), a neurturin, a neuregulin, a platelet derived growth factor (PDGF), a transforming growth factor (e.g., TGF-alpha and TGF-beta), apolipoprotein E (ApoE), a vasoactive intestinal peptide, artemin, persephin, netrin, neurotensin, GM-GSF, cardiotrophin-1, stem cell factor, midkine, pleiotrophin, a saposin, a semaporin, leukemia inhibitory factor, and the like.

Exemplary therapeutic antibodies or fragments that may be transported across the BBB or other TfR-containing cell membrane as a heterologous biologically active molecule of the invention include but are not limited to: antibodies for neurodegeneration including anti-Abeta, anti-Tau, anti-alpha-synuclein anti-Trem2, anti-C9orf7 dipeptides, anti-TDP-43, anti-prion protein C, anti-huntingtin, anti-nogo A, anti-TRAIL (tumor necrosis factor-related apoptosis-inducing ligand); antibodies for neuro-oncology including anti-HER2, anti-EGF, anti-PDGF, anti-PD1/PDL1, anti-CTLA-4, anti-IDO, anti-LAG-3, anti-CD20, anti-CD19, anti-CD40, anti-OX40, anti-TIM3, anti-toll-like receptors; antibodies for neuroinflammation including anti-TNF, anti-CD138, anti-IL-21, anti-IL-22; antibodies to viral diseases of the brain including anti-West Nile virus, anti-Zika, anti-HIV, anti-CMVanti-HSV and the like.

Exemplary enzymes that may be transported across the BBB or other TfR-containing cell membrane as a heterologous biologically active molecule of the invention include but are not limited to: alpha-L-iduronidase, iduronate-2-sulfatase, N-acetyl-galactosamine-6-sulfatase, arylsulfatase B, acid alpha-glucosidase, tripeptidyl-peptidase 1, acid sphingomyelinase glucocerebrosidase and heparan sulfamidase.

Also included as exemplary biologically active molecules are small molecules comprising chemical moieties (such as a therapeutic small molecule drugs); carbohydrates; polysaccharides; lipids; glycolipids and the like. Exemplary embodiments of such small molecule therapeutic agents include certain cancer drugs, such as daunorubicin, doxorubicin, and other cytotoxic chemical agents including microtubule inhibitors, topoisomerase inhibitors, platins, alkylating agents, and anti-metabolites all of which may beneficially be administered across the BBB at lower overall systemic doses than by IV administration. Other small molecule therapeutic agents may include corticosteroids, NSAIDs, COX-2 inhibitors, small molecule immunomodulators, non-steroidal immunosuppressants, 5-amino salicylic acid, DMARDs, hydroxychloroquine sulfate, and penicillamine. 1-D-ribofuranosyl-1,2,4-triazole-3 carboxamide, 9-2-hydroxy-ethoxy methylguanine, adamantanamine, 5-iodo-2'-deoxyuridine, trifluorothymidine, interferon, adenine arabinoside, protease inhibitors, thymidine kinase inhibitors, sugar or glycoprotein synthesis inhibitors, structural protein synthesis inhibitors, attachment and adsorption inhibitors, and nucleoside analogues such as acyclovir, penciclovir, valacyclovir, and ganciclovir, among others. Small molecule therapeutic agents which may be used according to the invention also include bevacizumab, cisplatin, irinotecan, methotrexate, temozolomide, taxol and zoledronate. Certain anti-inflammatory agents may be useful biologically active molecules. Fluoxetine, for example, reportedly inhibits MMP-2, MMP-9 and MMP-12 expression associated with blood-brain barrier disruption and inflammatory reactions after spinal cord injury, which may be used according to the invention to protect blood-brain barrier and to inhibit deleterious inflammatory responses in spinal cord injury and central nervous system disease. Other non-limiting examples of therapeutic antibodies which may be beneficially transported across the BBB include anti-CD133, anti-CD137, anti-CD27, anti-VEGF, anti-EGRFvIII, anti-IL-15 and anti-IL13R.

Exemplary embodiments of an imaging agent as an associated heterologous molecule include imaging agents that comprise at least one of a metal such as a paramagnetic metal, a radionuclide such as a radioisotope, a fluorochrome or fluorophor, an energy emitting particle, a detectable dye, and an enzyme substrate.

Further examples of biologically active molecules include small molecules, including therapeutic agents, in particular those with low blood-brain barrier permeability. Some examples of these therapeutic agents include cancer drugs, such as daunorubicin, doxorubicin, and toxic chemicals which, because of the lower dosage that can be administered by this method, can now be more safely administered. For example, a therapeutic agent can include bevacizumab, irinotecan, zoledronate, temozolomide, taxol, methotrexate, and cisplatin.

In another embodiment, the therapeutic agent can include a broad-spectrum antibiotic (e.g., cefotaxime, ceftriaxone, ampicillin and vancomycin); an antiviral agent (e.g., acyclovir); acetazolamide; carbamazepine; clonazepam; clorazepate dipotassium; diazepam; divalproex sodium; ethosuximide; felbamate; fosphenytoin sodium; gabapentin; lamotrigine; levetiracetam; lorazepam; oxcarbazepine; phenobarbital; phenytoin; phenytoin sodium; pregabalin; primidone; tiagabine hydrochloride; topiramate; trimethadione; valproic acid; zonisamide; copaxone; tysabri; novantrone; donezepil HCL; rivastigmine; galantamine; memantine; levodopa; carbidopa; parlodel, permax, requip, mirapex; Symmetrel; artane; cogentin; eldepryl; and deprenyl. Antiviral compounds are also beneficial therapeutic agents that can be delivered using a TfR-specific binding moiety of the invention, especially for cases in which the virus uses TfR transport as its route of entry into infected cells.

Numerous other examples of biologically active molecules may be used in association with a TfR-specific binding moiety of the invention, appropriate selection of which will be apparent to the skilled artisan depending on the condition, disease or disorder to be treated.

Yet other examples of a biologically active molecule which may be used according to the present invention is an antigenic peptide. Antigenic peptides may provide immunological protection when imported by cells involved in an immune response. Other examples include immunosuppressive peptides (e.g., peptides that block autoreactive T cells, such peptides being known in the art).

An imaging agent, as used herein, may be any chemical substance which may be used to provide a signal or contrast in imaging. A signal enhancing domain may be an organic molecule, metal ion, salt or chelate, a particle (e.g., iron particle), or a labeled peptide, protein, glycoprotein, polymer or liposome. For example, an imaging agent may include one or more of a radionuclide, a paramagnetic metal, a fluorochrome, a dye, and an enzyme substrate.

For x-ray imaging, the imaging agent may comprise iodinated organic molecules or chelates of heavy metal ions of atomic numbers 57 to 83. In certain embodiments, the imaging agent is $I^{125}$ labeled IgG (see, e.g., M. Sovak, ed., "Radiocontrast Agents," Springer-Verlag, pp. 23-125 (1984).

For ultrasound imaging, an imaging agent may comprise gas-filled bubbles or particles or metal chelates where the metal ions have atomic numbers 21-29, 42, 44 or 57-83. See e.g., Tyler et al., Ultrasonic Imaging, 3, pp. 323-29 (1981) and D. P. Swanson, "Enhancement Agents for Ultrasound: Fundamentals," Pharmaceuticals in Medical Imaging, pp. 682-87. (1990) for other suitable compounds.

For nuclear radiopharmaceutical imaging or radiotherapy, an imaging agent may comprise a radioactive molecule. In certain embodiments, chelates of Tc, Re, Co, Cu, Au, Ag, Pb, Bi, In and Ga may be used. In certain embodiments, chelates of Tc-99m may be used. See e.g., Rayudu G V S, Radiotracers for Medical Applications, I, pp. 201 and D. P. Swanson et al., ed., Pharmaceuticals in Medical Imaging, pp. 279-644 (1990) for other suitable compounds.

For ultraviolet/visible/infrared light imaging, an imaging agent may comprise any organic or inorganic dye or any metal chelate.

For MRI, an imaging agent may comprise a metal-ligand complex of a paramagnetic form of a metal ion with atomic numbers 21-29, 42, 44, or 57-83. In certain embodiments, the paramagnetic metal is selected from: Cr(III), Cu(II), Dy(III), Er(III) and Eu(III), Fe(III), Gd(III), Ho(III), Mn(II and III), Tb(III). A variety of chelating ligands useful as MRI agents are well known in the art.

In sum, the invention includes TfR-specific conjugates comprising a TfR-specific binding moiety of the invention operably linked to a heterologous molecule which differs in biological activity from said moiety. Such operable linkages can be a covalent or non-covalent linkage and the heterologous molecule can be a growth factor, cytokine, lymphokine, cell surface antigen or an antibody or antibody fragment which binds to any of the foregoing; a chimeric antigen receptor; a cytotoxic small molecule; a biochemical pathway agonist or antagonist; a therapeutic agent or drug; a diagnostic agent such as a fluorescent molecule or other molecular marker; or a nucleic acid molecule with targeting or other regulatory properties (e.g., silencers) or which encodes a regulatory molecule for a cell.

For the avoidance of doubt, a TfR-selective binding compound includes TfR-specific binding moieties alone, as part of antibodies (or fragments thereof as described herein), as part of conjugates or encoded in viral or other vectors.

Monitoring TfR Binding and Cell Internalization

TfR-binding activity (also referred to herein as "TfR bioactivity") may be determined by one or more assays described in the Examples herein, or by any other suitable method in the art, including well-known immunoassays, such as for example the ELISAs or variations thereon described in the Examples. Any other binding assay which directly or indirectly measures the binding of the TfR-specific binding moiety to a cell surface TfR, or alternatively, which measures the ability of a TfR-specific binding moiety, conjugate or compound comprising such a moiety of the invention to compete for binding to TfR in the presence of a different TfR binding compound (such as an anti-TfR antibody) such as by a competitive inhibition assay, may be used. Preferably, a selected assay measures the effect of a TfR-specific binding moiety or compound comprising such a moiety on its ability to transport a heterologous molecule or biomolecule across the membrane of a TfR-positive cell. In certain embodiments, the TfR-positive cell is one which transports a heterologous molecule across the blood brain barrier (BBB). In certain embodiments, the TfR-positive cell is one which transports a heterologous molecule across cells of the gastrointestinal tract. In certain embodiments, binding of the TfR binding moiety to TfR is measured by monitoring internalization of the TfR binding moiety into TfR-positive cells or cell type. In vivo assays of TfR bioactivity include, but are not limited to, those described in the Examples herein.

Other test systems to assess TfR binding and functional activity include, for example: Surface plasmon resonance to determine affinity and off-rates; using radiolabeled or fluorescent tagged molecule or GFP fusion proteins in in vitro or in vivo animal studies including binding and internalization in tumor cell lines, immortalized endothelial cell lines or primary cells expressing TfR; in vitro transcytosis in capillary endothelial cells and cells lines; and permeability assay using Caco-2 and MDCK epithelial cell lines; in situ perfusion models and immunohistochemical or immunofluorescent staining of tissue sections; optical or PET animal imaging; standard PK and tissue distribution assays; and measuring one or more biological effects of a heterologous molecule (drug cargo or payload) in normal animals or disease animal models.

Therapeutic versions of compounds with TfR-specific binding moieties of the invention include other molecular configurations, e.g., a VNAR monomer (i.e., a TfR-binding moiety) fused to stabilizing heterologous peptide regions, e.g., the Fc domain of an IgG or other immunoglobulin molecule, which may be expressed and then further purified as multimers, such as covalent dimers, allowing the activity of certain such therapeutic molecules to have even greater potency, preferably by at least 2-10 fold higher potencies and different binding affinities to TfR-1. Any of the antibody or antibody-like structures contemplated by the invention can be used as therapeutics in the methods of the invention Pharmaceutically acceptable salts or solvates of any of the TfR-specific binding compounds of the invention are likewise within the scope of the present invention. As used herein, the term "pharmaceutically acceptable salt" refers to a salt that is not harmful to a patient or subject to which the salt in question is administered. It may be a salt chosen, e.g., among acid addition salts and basic salts. Examples of acid addition salts include chloride salts, citrate salts and acetate salts. Examples of basic salts include salts wherein the cation is selected from alkali metal cations, such as sodium or potassium ions, alkaline earth metal cations, such as calcium or magnesium ions, as well as substituted ammonium ions, such as ions of the type N(R1)(R2)(R3)(R4)+, wherein R1, R2, R3 and R4 independently will typically designate hydrogen, optionally substituted $C_{1-6}$-alkyl groups or optionally substituted $C_{2-6}$-alkenyl groups. Examples of relevant $C_{1-6}$-alkyl groups include methyl, ethyl, 1-propyl and 2-propyl groups. Examples of $C_{2-6}$-alkenyl groups of possible relevance include ethenyl, 1-propenyl and 2-propenyl. Other examples of pharmaceutically acceptable salts are described in "Remington's Pharmaceutical Sciences", 17th edition, Alfonso R. Gennaro (Ed.), Mark Publishing Company, Easton, PA, USA, 1985 (and more recent editions thereof), in the "Encyclopaedia of Pharmaceutical Technology", 3rd edition, James Swarbrick (Ed.), Informa Healthcare USA (Inc.), NY, USA, 2007, and in J. Pharm. Sci. 66: 2 (1977).

The term "solvate" in the context of the present invention refers to a complex of defined stoichiometry formed between a solute (in casu, a peptide compound or pharmaceutically acceptable salt thereof according to the invention) and a solvent. The solvent in this connection may, for example, be water, ethanol or another pharmaceutically acceptable, typically small-molecular organic species, such as, but not limited to, acetic acid or lactic acid. When the solvent in question is water, such a solvate is normally referred to as a hydrate.

In each of the sequences described above, and in each sequence described herein, a C-terminal "—OH" moiety may be substituted for a C-terminal "—NH$_2$" moiety, and vice-versa.

Each of the specific compounds of the invention (e.g., TfR binding moieties, TfR antagonist peptides and compounds), and pharmaceutically acceptable salts and solvates thereof, constitutes an individual embodiment of the invention.

Conjugates

TfR specific VNAR comprising compounds of the invention may optionally be conjugated (e.g., using linkers such as chemical linkers and/or linker peptides which are not usually associated with the domains being associated) to one or more additional agents which may include therapeutic and/or diagnostic agents. Such agents include but are not limited to chemotherapeutics such as cytostatic drugs, cytotoxins, radioisotopes, chelators, enzymes, nucleases, nucleic acids such as DNA, RNA or mixed nucleic acid oligonucleotides, including siRNAs, shRNAs, microRNAs, aptamers and the like; immunomodulators such as therapeutic antibodies, antibody and antibody-like fragments, inflammatory and anti-inflammatory cytokines, anti-inflammatory agents, radiotherapeutics, photoactive agents, diagnostic markers and the like. In certain embodiments, the pharmaceutically active moieties of the invention comprise at least one scFv molecule that is operably linked via a linker peptide to the C-terminus and/or N-terminus of an Fc region.

In certain embodiments, a compound of the invention comprising a TfR-specific binding moiety is multispecific, i.e., has at least one binding site that binds to a first molecule or epitope of a molecule (e.g., human TfR-1) and one or more other binding sites that bind to at least one heterologous molecule or to an epitope of either TfR-1 or another molecule. Multispecific binding molecules of the invention may comprise at least two binding sites, three binding sites, four binding sites or more. In certain embodiments, at least two binding sites of a multispecific binding molecule of the invention are capable of transporting a linked molecule across the BBB.

The invention thus further provides methods of making derivatives of TfR specific VNARs of the invention using biochemical engineering techniques well known to those of skill in the art. Such derivatives include, inter alia, multivalent or multispecific molecules comprising a TfR-specific binding moiety, including immunoconjugates. A large body of art is available relating to how to make and use antibody drug conjugates. Such knowledge and skill in the art may be adapted for use with the TfR specific binding moieties and TfR selective binding compounds of the invention. See, e.g., WO2007/140371; WO2006/068867 specific to TfR; methods relating to making and/or using different ligand conjugates may be applied. In certain embodiments, the TfR selective binding moieties and TfR selective binding compounds of the present invention include covalently modified and conjugated polypeptides forms of the polypeptides (e.g., immunoadhesins, radiolabeled or fluorescently labeled compounds, and the like). Methods for peptide conjugation and for labeling polypeptides and conjugating molecules are well known in the art.

Nucleic Acid Sequences that Encode a TfR Selective Binding Moiety or TfR Antagonist Compound In one aspect, the invention provides an isolated nucleic acid which encodes a TfR specific binding moiety or compound of the invention, or a fragment or derivative thereof. The invention also provides an isolated nucleic acid molecule comprising a sequence that hybridizes under stringent conditions to a nucleic acid sequence which encodes a TfR specific binding moiety or compound of the invention, or a fragment or derivative thereof, or the antisense or complement of any such sequence.

In another aspect, the invention provides an isolated nucleic acid molecule encoding a fusion protein comprising at least two segments, wherein one of the segments comprises a Clone H variant according to the invention. In certain embodiments, a second segment comprises a heterologous signal polypeptide, a heterologous binding moiety, an immunoglobulin fragment such as a Fc domain, or a detectable marker.

One aspect of the invention provides isolated nucleic acid molecules that encode TfR specific binding moiety proteins or biologically active portions thereof. Also included are nucleic acid fragments sufficient for use as hybridization probes to identify TfR binding moiety encoding nucleic acids and fragments for use as polymerase chain reaction (PCR) primers for the amplification or mutation of TfR specific binding moiety encoding nucleic acid molecules.

As used herein, the term "nucleic acid molecule" is intended to include DNA molecules, RNA molecules (e.g., mRNA, shRNA, siRNA, microRNA), analogs of the DNA or RNA generated using nucleotide analogs, and derivatives, fragments and homologs thereof. The nucleic acid molecules of the invention may be single-, double-, or triple-stranded. A nucleic acid molecule of the present invention may be isolated using sequence information provided herein and well known molecular biological techniques (e.g., as described in Sambrook et al., Eds., MOLECULAR CLONING: A LABORATORY MANUAL 2ND ED., Cold Spring Harbor Laboratory Press, Cold Spring Harbor, N.Y., 1989; and Ausubel, et al., Eds., CURRENT PROTOCOLS IN MOLECULAR BIOLOGY, John Wiley & Sons, New York, N.Y., 1993).

A nucleic acid molecule of the invention may be amplified using any form of nucleic acid template and appropriate oligonucleotide primers according to standard PCR amplification techniques. Amplified nucleic acid may be cloned into an appropriate vector and characterized, e.g., by restriction analysis or DNA sequencing. Furthermore, oligonucleotides corresponding to nucleotide sequences that encode a TfR selective binding moiety or compound of the invention may be prepared by standard synthetic techniques, e.g., using an automated DNA synthesizer.

The term "oligonucleotide" as used herein refers to a series of covalently linked nucleotide (or nucleoside residues, including ribonucleoside or deoxyribonucleoside residues) wherein the oligonucleotide has a sufficient number of nucleotide bases to be used in a PCR reaction. Oligonucleotides comprise portions of a nucleic acid sequence having at least about 10 nucleotides and as many as 50 nucleotides, preferably about 15 nucleotides to 30 nucleotides. Oligonucleotides may be chemically synthesized and may be used as probes. A short oligonucleotide sequence may be used to amplify, confirm, or reveal the presence of an identical, similar or complementary DNA or RNA in a particular cell or tissue.

Derivatives or analogs of the nucleic acid molecules (or proteins) of the invention include, inter alia, nucleic acid (or polypeptide) molecules having regions that are substantially homologous to the nucleic acid molecules or proteins of the invention, e.g., by at least about 45%, 50%, 70%, 80%, 95%, 98%, or even 99% identity (with a preferred identity of 80-99%) over a nucleic acid or amino acid sequence of the same size or when compared to an aligned sequence in which the alignment is done by a computer homology program known in the art. A percent identity for any candidate nucleic acid or polypeptide relative to a reference nucleic acid or polypeptide may be determined by aligning a reference sequence to one or more test sequences using, for example, the computer program ClustalW (version 1.83, default parameters), which enable nucleic acid or polypeptide sequence alignments across their entire lengths (global alignment) or across a specified length. The number of identical matches in such a ClustalW alignment is divided by the length of the reference sequence and multiplied by 100.

Also included are nucleic acid molecules capable of hybridizing to the complement of a sequence encoding the proteins of the invention under stringent or moderately stringent conditions. See e.g. Ausubel, et al., CURRENT PROTOCOLS IN MOLECULAR BIOLOGY, John Wiley & Sons, New York, N.Y., 1993, and below. An exemplary program is the GAP program (Wisconsin Sequence Analysis Package, Version 8 for UNIX, Genetics Computer Group, University Research Park, Madison, Wis.) using the default settings, which uses the algorithm of Smith and Waterman (1981) Adv. Appl. Math. 2:482489). Derivatives and analogs may be full length or other than full length, if the derivative or analog contains a modified nucleic acid or amino acid, as described below.

Stringent conditions are known to those skilled in the art and may be found in CURRENT PROTOCOLS IN MOLECULAR BIOLOGY, John Wiley & Sons, N.Y. (1989), 6.3.1-6.3.6. In certain embodiments, stringent conditions typically permit sequences at least about 65%, 70%, 75%, 85%, 90%, 95%, 98%, or 99% homologous to each other to remain hybridized to each other. A non-limiting example of stringent hybridization conditions is hybridization in a high salt buffer comprising 6×SSC, 50 mM Tris-HCl (pH 7.5), 1 mM EDTA, 0.02% PVP, 0.02% Ficoll, 0.02% BSA, and 500 mg/ml denatured salmon sperm DNA at 65° C. This hybridization is followed by one or more washes in 0.2×SSC, 0.01% BSA at 50° C. The term "stringent hybridization conditions" as used herein refers to conditions under which a nucleic acid probe, primer or oligonucleotide will hybridize to its target sequence, but only negligibly or not at all to other nucleic acid sequences. Stringent conditions are sequence- and length-dependent, and depend on % (percent)-identity (or %-mismatch) over a certain length of nucleotide residues. Longer sequences hybridize specifically at higher temperatures than shorter sequences. Generally, stringent conditions are selected to be about 5° C. lower than the thermal melting point (Tm) for the specific sequence at a defined ionic strength and pH. Stringent conditions may also be achieved with the addition of destabilizing agents, such as formamide.

Methods of Producing TfR Specific VNAR Binding Moieties and Compounds Comprising Them The compounds of the invention may be manufactured by standard synthetic methods, by use of recombinant expression systems, or by any other suitable method. Thus, the compounds may be synthesized in a number of ways, including, e.g., methods comprising: (1) synthesizing a polypeptide or polypeptide component of a TfR specific binding compound using standard solid-phase or liquid-phase methodology, either stepwise or by fragment assembly, and isolating and purifying the final peptide compound product; (2) expressing a nucleic acid construct that encodes a polypeptide or polypeptide component of a TfR specific binding compound in a host cell and recovering the expression product from the host cell or host cell culture; or (3) cell-free in vitro expression of a nucleic acid construct encoding a polypeptide or polypeptide component of a TfR specific binding compound, and recovering the expression product; or by any combination of the methods of (1), (2) or (3) to obtain fragments of the peptide component, subsequently joining (e.g., ligating) the fragments to obtain the peptide component, and recovering the peptide component.

It may be preferable to synthesize a polypeptide or polypeptide component of a TfR-specific binding compound of the invention by means of solid-phase or liquid-phase peptide synthesis. Compounds of the invention may suitably be manufactured by standard synthetic methods. Thus, peptides may be synthesized by, e.g., methods comprising synthesizing the peptide by standard solid-phase or liquid-phase methodology, either stepwise or by fragment assembly, and isolating and purifying the final peptide product. In this context, reference may be made to WO1998/11125 or, inter alia, Fields, G. B. et al., "Principles and Practice of Solid-Phase Peptide Synthesis"; in: Synthetic Peptides, Gregory A. Grant (ed.), Oxford University Press (2nd edition, 2002) and the synthesis examples herein.

Accordingly, the present invention also provides methods for producing a TfR specific binding compound of the invention according to above recited methods; a nucleic acid molecule encoding part or all of a polypeptide of the invention, a vector comprising at least one nucleic acid of the invention, expression vectors comprising at least one nucleic acid of the invention capable of producing a polypeptide of the invention when introduced into a host cell, and a host cell comprising a nucleic acid molecule, vector or expression vector of the invention.

TfR specific binding compounds of the invention may be prepared using recombinant techniques well known in the art. In general, methods for producing polypeptides by culturing host cells transformed or transfected with a vector comprising the encoding nucleic acid and recovering the polypeptide from cell culture are described in, e.g., Sambrook et al., Molecular Cloning: A Laboratory Manual (New York: Cold Spring Harbor Laboratory Press, 1989); Dieffenbach et al., PCR Primer: A Laboratory Manual (Cold Spring Harbor Laboratory Press, 1995).

A nucleic acid encoding a desired polypeptide may be inserted into a replication vector for further cloning (amplification) of the DNA or for expression of the nucleic acid into RNA and protein. A multitude of cloning and expression vectors are publicly available.

Expression vectors capable of directing transient or stable expression of genes to which they are operably linked are well known in the art. The vector components generally include, but are not limited to, one or more of the following: a heterologous signal sequence or peptide, an origin of replication, one or more marker genes, an enhancer element, a promoter, and a transcription termination sequence, each of which is well known in the art. Optional regulatory control sequences, integration sequences, and useful markers that can be employed are known in the art.

Any suitable host cell may be used to produce TfR specific binding compounds of the invention. Host cells may be cells stably or transiently transfected, transformed, transduced or infected with one or more expression vectors which drive expression of a polypeptide of the invention. Suitable host cells for cloning or expressing nucleic acids of the invention include prokaryote, yeast, or higher eukaryote cells. Eukaryotic microbes such as filamentous fungi yeast, *Arabidopsis*, and other plant and animal eukaryotic host cells that may be grown in liquid culture are suitable cloning or expression hosts for vectors. Suitable host cells for the expression of glycosylated polypeptides may also be derived from multicellular organisms.

Creation and isolation of host cell lines producing a TfR-specific binding moiety, conjugate or compound of the invention can be accomplished using standard techniques known in the art. Mammalian cells are preferred host cells for expression of peptides. Particularly useful mammalian cells include, inter alia, HEK 293, NSO, DG-44, and CHO cells, but any other suitable host cell may be used according to the invention. Preferably, the TfR-specific moieties, conjugates or compounds are secreted into the medium in which the host cells are cultured, from which the TfR-specific binding moieties, conjugates or compounds may be recovered or purified.

When a polypeptide is produced in a recombinant cell other than one of human origin, it is typically free of polypeptides of human origin. In certain embodiments, it is advantageous to separate a polypeptide away from other recombinant cell components such as host cell polypeptides to obtain preparations that are of high purity or substantially homogeneous. As a first step, culture medium or cell lysates may be centrifuged to remove particulate cell debris and suitable protein purification procedures may be performed. Such procedures include, inter alia, fractionation (e.g., size separation by gel filtration or charge separation by ion-exchange column); ethanol precipitation; Protein A Sepharose columns to remove contaminants such as IgG; hydrophobic interaction chromatography; reverse phase HPLC; chromatography on silica or on cation-exchange resins such as DEAE and the like; chromatofocusing; electrophoretic separations; ammonium sulfate precipitation; gel filtration using, for example, Sephadex beads such as G-75. Any number of biochemical purification techniques may be used to increase the purity of a TfR-specific binding moiety, conjugate or compound of the invention.

Methods of Detection

In certain embodiments, the TfR specific binding compounds of the invention may be used to detect and quantify levels of TfR, or cells that express TfR. This can be achieved, for example, by contacting a test sample (such as an in vitro sample) and a control sample with a TfR specific binding moiety of the invention, or a compound comprising it, under conditions which permit formation of a complex between the compound and TfR, or between TfR and an anti-TfR antibody, or both. Any bound TfR complexes are detected and/or quantified in TfR specific VNAR containing samples and control samples.

Accordingly, the invention further provides methods for detecting the presence of TfR or TfR antibodies in a sample, or measuring the amount of either of the foregoing, comprising contacting the sample, and preferably a control sample, with a TfR-binding compound of the invention under conditions that permit complex formation between the TfR binding moiety of the compound and TfR, e.g., human TfR. Formation or inhibition of formation of a TfR-binding compound/TfR complex is then detected and/or quantified. A variety of tests can be designed based on features of binding or competition for binding. For example, the presence of TfR in a test sample may be detected directly, or may be detected and quantified based on the ability to compete for binding of TfR by a TfR-binding moiety, conjugate or compound. In general, the difference in complex formation between a test sample and a control sample is indicative of a binding interaction.

Methods of Treatment Using TfR Binding Moieties and Compositions

The present invention provides a TfR binding moiety or TfR specific binding compound for use, alone or in combination with one or more additional therapeutic agents in a pharmaceutical composition, for treatment or prophylaxis of conditions, diseases and disorders responsive to modulation (such as inhibiting or blocking) of the interaction between TfR and its in vivo ligands.

In certain embodiments, a TfR specific binding moiety or a conjugate or drug delivery vehicle comprising such a binding moiety is administered in combination with at least one additional agent that mediates blood-brain barrier transport, such as an agent comprising a receptor binding domain of an apolipoprotein such as a receptor binding domain of ApoA, ApoB, ApoC, ApoD, ApoE, ApoE2, ApoE3 or ApoE4, and any combination thereof Any one of a number of other molecules which mediate transport of heterologous molecules across the blood brain barrier may be used in combination with the TfR specific binding moiety comprising agents of the invention, including, e.g., IgG, YY (PYY), neuropeptide Y (NPY), corticotropin releasing factor (CRF), and urocortin. Certain viral glycoproteins (e.g., rabies virus glycoprotein (RVG) peptide) and antibodies and antibody fragments may also be used in this regard. Such agents are also termed payloads.

Combination therapies may include co-administration of agents or alternate administrations which result in a combination therapy within the patient based on duration of the therapeutic agent(s) or their biological effects in the patient.

In certain embodiments, a therapeutic agent transported across the BBB in association with a TfR-specific binding moiety of the invention is effective in treating a brain or CNS disease, condition, injury or disorder, such as, for example, neurodegenerative diseases, neuronal injury, stroke, genetic disorders, psychiatric disorders, developmental disorders, inflammation, infection or damage, and brain cancers, spinal cord injury (SCI) and traumatic brain injury (TBI). In certain embodiments, a brain disorder is selected from epilepsy, meningitis, encephalitis including HIV Encephalitis, progressive multifocal leukoencephalopathy, neuromyelitis optica, multiple sclerosis, late-stage neurological trypanosomiasis, amyotrophic lateral sclerosis (ALS), progressive bulbar palsy (PBP), primary lateral sclerosis (PLS), progressive muscular atrophy (PMA), Alzheimer's disease, Parkinson's disease, Huntington's disease, De Vivo disease, and any type of tumor, cancer or hyperproliferative disease in the brain or CNS.

In certain embodiments, a therapeutic agent transported across a hTfR1-containing membrane in association with a TfR-specific binding moiety of the invention is effective in treating a condition, disease or disorder associated with the GI tract or one which will otherwise benefit from drug delivery across an epithelial membrane of the gut mediated by hTfR1 transport.

The invention in certain embodiments provides methods of treatment or prevention of a TfR associated disorder, the method comprising the step of administering to a subject (e.g., a patient) in need thereof a therapeutically effective amount of the TfR specific binding compound or pharmaceutical composition comprising a TfR binding compound of the invention, as described herein. As used herein, an "effective amount," a "therapeutically effective amount" or an "effective dose" is an amount of a composition (e.g., a therapeutic composition or agent) that produces at least one desired therapeutic effect in a subject, such as preventing or treating a target condition or beneficially alleviating a symptom associated with the condition.

The most desirable therapeutically effective amount is an amount that will produce a desired efficacy of a particular treatment selected by one of skill in the art for a given subject in need thereof. This amount will vary depending upon a variety of factors understood by the skilled worker, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. See, e.g., Remington: The Science and Practice of Pharmacy 21st Ed., Univ. of Sciences in Philadelphia (USIP), Lippincott Williams & Wilkins, Philadelphia, PA, 2005.

Additionally, for some embodiments, specificity for TfR1 is an important feature for a BBB carrier because off-target binding to TfR2 could have undesirable safety and/or PK consequences. The expression of TfR2 is restricted to hepatocytes and erythroid precursors (Silvestri 2014). Interference with transferrin binding to TfR2, which is a component of the erythropoietin receptor complex, could disrupt normal erythropoiesis (Forejtnikovà 2010). Additionally, high levels of TfR2 expressed in the liver may be responsible for the rapid clearance and short half-life of some cross-reacting UR antibodies (Boado 2009). VNAR antibodies to TfR1 are highly specific and exhibit the same long half-life as IgG.

Hence, in some embodiments, the method of medical treatment comprises administering a therapeutically-effective amount of a pharmaceutical composition comprising a TfR-binding moiety of the invention, or a conjugate thereof, to the brain of a mammalian subject in need thereof.

Other embodiments of the invention are directed to methods of targeting delivery of a payload to brain parenchymal tissue in a mammal or to other tissue or cells in the mammal that have TfR-R-expressing cells which comprises contacting said tissue or cells with a TfR-specific binding moiety, or conjugate thereof. In some embodiments, targeting delivery of the payload comprises administering a TfR-specific binding moiety, or conjugate thereof, to a mammal in need of treatment for a medical condition.

As used herein, the payload comprises any of the therapeutic agents that can be conjugated to the TfR-specify binding moieties. In some embodiments, the payload dissociates from or can be cleaved from the TfR-specific binding moiety after internalization or after crossing the membranes. In some embodiments, the TfR-specific binding moiety and the payload remain conjugated after internalization or crossing the membrane. The TfR-specific binding moiety-payload conjugate is an immunoconjugate and can be bivalent or multivalent, and likewise can be bispecific or multispecific.

Pharmaceutical Compositions

The present invention further provides pharmaceutical compositions comprising a TfR-specific binding moiety of the invention or compound, or a pharmaceutically acceptable salt or solvate thereof, according to the invention, together with a pharmaceutically acceptable carrier, excipient or vehicle.

Accordingly, the present invention further provides a pharmaceutical composition comprising a TfR-specific binding moiety of the invention or compound comprising a TfR-specific binding moiety, as well as variant and derivative compounds comprising a TfR-specific binding moiety of the invention. Certain embodiments of the pharmaceutical compositions of the invention are described in further detail below.

The present invention also provides pharmaceutical compositions comprising a TfR-specific binding moiety or a TfR-specific binding compound for use in treating, ameliorating or preventing one or more diseases, conditions, disorders or symptoms relating to B cells and immunoglobulin production, as described in further detail below. Each such disease, condition, disorder or symptom is envisioned to be a separate embodiment with respect to uses of a pharmaceutical composition according to the invention.

Formulations, Administration and Dosing

TfR specific binding compounds of the present invention, or salts thereof, may be formulated as pharmaceutical compositions prepared for storage or administration, which typically comprise a therapeutically effective amount of a compound of the invention, or a salt thereof, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person. The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans.

The term "pharmaceutically acceptable salt" refers to the salt of the compounds. Salts include pharmaceutically acceptable salts such as acid addition salts and basic salts. Examples of acid addition salts include hydrochloride salts, citrate salts and acetate salts. Examples of basic salts include salts where the cation is selected from alkali metals, such as sodium and potassium, alkaline earth metals such as calcium, and ammonium ions $^+N(R^3)_3(R^4)$, where $R^3$ and $R^4$ independently designate optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, PA, U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms when compared to the absence of treatment, and is not necessarily meant to imply complete cessation of the relevant condition.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. Compositions may be formulated for any suitable route and means of administration.

Pharmaceutically acceptable carriers or diluents include those used in formulations suitable for oral, rectal, nasal or parenteral (including subcutaneous, intramuscular, intravenous, intradermal, and transdermal) administration. The formulations may conveniently be presented in unit dosage form and may be prepared by any of the methods well known in the art of pharmacy. Subcutaneous or transdermal modes of administration may be particularly suitable for the compounds described herein.

An acceptable route of administration may refer to any administration pathway known in the art, including but not limited to aerosol, enteral, nasal, ophthalmic, oral, parenteral, rectal, vaginal, or transdermal (e.g., topical administration of a cream, gel or ointment, or by means of a transdermal patch). "Parenteral administration" is typically associated with injection at or in communication with the intended site of action, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal administration.

In another aspect, the present invention provides a composition, e.g., a pharmaceutical composition, comprising one or a combination of different TfR specific binding compounds of the invention, or a VNAR sequence containing, TfR specific binding region thereof, or an ester, salt or amide of any of the foregoing, and at least one pharmaceutically acceptable carrier. Such compositions may include one or more different TfR specific binding moieties or compounds in combination to produce an immunoconjugate or multi-specific molecule comprising at least one TfR specific binding moiety. For example, a pharmaceutical composition of the invention may comprise a combination of TfR specific binding moieties which bind to different epitopes of TfR or which otherwise have complementary biological activities.

Pharmaceutical compositions of the invention may be administered alone or in combination with one or more other therapeutic or diagnostic agents. A combination therapy may include a TfR specific binding compound of the present invention combined with at least one other therapeutic agent selected based on the particular patient, disease or condition to be treated. Examples of other such agents include, inter alia, a cytotoxic, anti-cancer or chemotherapeutic agent, an anti-inflammatory or anti-proliferative agent, an antimicrobial or antiviral agent, growth factors, cytokines, an analgesic, a therapeutically active small molecule or polypeptide, a single chain antibody, a classical antibody or fragment thereof, or a nucleic acid molecule which modulates one or more signaling pathways, and similar modulating therapeutics which may complement or otherwise be beneficial in a therapeutic or prophylactic treatment regimen.

As used herein, "pharmaceutically acceptable carrier" includes any and all physiologically acceptable, i.e., compatible, solvents, dispersion media, coatings, antimicrobial agents, isotonic and absorption delaying agents, and the like. In certain embodiments, the carrier is suitable for intravenous, intramuscular, subcutaneous, parenteral, spinal or epidermal administration (e.g., by injection or infusion). Depending on selected route of administration, the TfR specific binding moiety comprising compound or component may be coated in a material or materials intended to protect the compound from the action of acids and other natural inactivating conditions to which the active TfR binding moiety may encounter when administered to a subject by a particular route of administration.

As above, a compound of the invention may encompass one or more pharmaceutically acceptable salts. As used herein a "pharmaceutically acceptable salt" retains qualitatively a desired biological activity of the parent compound without imparting any undesired effects relative to the compound. Examples of pharmaceutically acceptable salts include acid addition salts and base addition salts. Acid addition salts include salts derived from nontoxic inorganic acids, such as hydrochloric, nitric, phosphorous, phosphoric, sulfuric, hydrobromic, hydroiodic and the like, or from nontoxic organic acids such as aliphatic mono- and di-carboxylic acids, phenyl-substituted alkanoic acids, hydroxy alkanoic acids, aromatic acids, aliphatic and aromatic sulfonic acids and the like. Base addition salts include salts derived from alkaline earth metals, such as sodium, potassium, magnesium, calcium and the like, as well as from nontoxic organic amines, such as N, N'-dibenzylethylenediamine, N-methylglucamine, chloroprocaine, choline, diethanolamine, ethylenediamine, procaine and the like.

A pharmaceutical composition of the invention also optionally includes a pharmaceutically acceptable antioxidant. Exemplary pharmaceutically acceptable antioxidants are water soluble antioxidants such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propylgallate, alpha-tocopherol, and the like; and metal chelating agents, such as citric acid, ethylenediamine tetraacetic acid (EDTA), sorbitol, tartaric acid, phosphoric acid, and the like.

Examples of suitable aqueous and nonaqueous carriers that may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyloleate. Proper fluidity can be maintained, for example, by the use of coating materials, such as lecithin, by the maintenance of the required particle size in the case of dispersions, and by the use of surfactants.

TfR selective binding moieties and compositions may also contain adjuvants such as preservatives, wetting agents, emulsifying agents and dispersing agents. Prevention of presence of microorganisms may be ensured both by sterilization procedures, and by the inclusion of various antibacterial and antifungal agents, for example, paraben, chlorobutanol, phenol sorbic acid, and the like. Isotonic agents, such as sugars, sodium chloride, and the like into the compositions, may also be desirable. In addition, prolonged absorption of the injectable pharmaceutical form may be brought about by the inclusion of agents which delay absorption such as, aluminum monostearate and gelatin.

Exemplary pharmaceutically acceptable carriers include sterile aqueous solutions or dispersions and sterile powders for the extemporaneous preparation of sterile injectable solutions or dispersion. Such media and reagents for pharmaceutically active substances are known in the art. The pharmaceutical compositions of the invention may include any conventional media or agent unless any is incompatible with the active TfR specific binding compound. Supplementary active compounds may further be incorporated into the compositions.

Therapeutic compositions are typically sterile and stable under the conditions of manufacture and storage. The composition may be formulated as a solution, microemulsion, liposome, or other ordered structure suitable to high drug concentration. The carrier may be a solvent or dispersion medium containing, for example, water, alcohol such as ethanol, polyol (e.g., glycerol, propylene glycol, and liquid polyethylene glycol), or any suitable mixtures. The proper fluidity may be maintained, for example, by the use of a coating such as lecithin, by the maintenance of the required particle size in the case of dispersion and by use of surfactants according to formulation chemistry well known in the art. In certain embodiments, isotonic agents, e.g., sugars, polyalcohols such as mannitol, sorbitol, or sodium chloride may be desirable in the composition. Prolonged absorption of injectable compositions may be brought about by including in the composition an agent that delays absorption for example, monostearate salts and gelatin.

Solutions or suspensions used for intradermal or subcutaneous application typically include one or more of: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates; and tonicity adjusting agents such as, e.g., sodium chloride or dextrose. The pH can be adjusted with acids or bases, such as hydrochloric acid or sodium hydroxide, or buffers with citrate, phosphate, acetate and the like. Such preparations may be enclosed in ampoules, disposable syringes or multiple dose vials made of glass or plastic.

Sterile injectable solutions may be prepared by incorporating a TfR specific binding moiety (or a TfR binding compound comprising such a moiety) in the required amount in an appropriate solvent with one or a combination of ingredients described above, as required, followed by sterilization microfiltration. Dispersions may be prepared by incorporating the active compound into a sterile vehicle that contains dispersion medium and other ingredients, such as those described above. In the case of sterile powders for the preparation of sterile injectable solutions, the methods of preparation are vacuum drying and freeze-drying (lyophilization) that yield a powder of the active ingredient in addition to any additional desired ingredient from a sterile-filtered solution thereof.

When a therapeutically effective amount of a TfR selective binding moiety or composition of the invention is administered by, e.g., intravenous, cutaneous or subcutaneous injection, the binding agent will be in the form of a pyrogen-free, parenterally acceptable aqueous solution. Methods for preparing parenterally acceptable protein solutions, taking into consideration appropriate pH, isotonicity, stability, and the like, are within the skill in the art. A preferred pharmaceutical composition for intravenous, cutaneous, or subcutaneous injection will contain, in addition to binding agents, an isotonic vehicle such as sodium chloride injection, Ringer's injection, dextrose injection, dextrose and sodium chloride injection, lactated Ringer's injection, or other vehicle as known in the art. A pharmaceutical composition of the present invention may also contain stabilizers, preservatives, buffers, antioxidants, or other additives well known to those of skill in the art.

The amount of active ingredient which can be combined with a carrier material to produce a single dosage form will vary depending on a variety of factors, including the subject being treated, and the particular mode of administration. In general, it will be an amount of the composition that produces an appropriate therapeutic effect under the particular circumstances. Generally, out of one hundred percent, this amount will range from about 0.01 percent to about ninety-nine percent of active ingredient, from about 0.1 percent to about 70 percent, or from about 1 percent to about 30 percent of active ingredient in combination with a pharmaceutically acceptable carrier.

Dosage regimens may be adjusted to provide the optimum desired response (e.g., a therapeutic response). For example, a single bolus may be administered, several divided doses may be administered over time, or the dose may be proportionally reduced or increased as indicated by the particular circumstances of the therapeutic situation, on a case by case basis. It is especially advantageous to formulate parenteral compositions in dosage unit forms for ease of administration and uniformity of dosage when administered to the subject or patient. As used herein, a dosage unit form refers to physically discrete units suitable as unitary dosages for the subjects to be treated; each unit containing a predetermined quantity of active compound calculated to produce a desired therapeutic effect in association with the required pharmaceutical carrier. The specification for the dosage unit forms of the invention depend on the specific characteristics of the active compound and the particular therapeutic effect(s) to be achieved, taking into consideration and the treatment and sensitivity of any individual patient.

For administration of a TfR selective binding moiety or compound, the dosage range will generally be from about 0.0001 to 100 mg/kg, and more usually 0.01 to 5 mg/kg, of the host body weight. Exemplary dosages may be 0.25 mg/kg body weight, 1 mg/kg body weight, 3 mg/kg body weight, 5 mg/kg body weight or 10 mg/kg body weight or within the range of 1-10 mg/kg. An exemplary treatment regime is a once or twice daily administration, or a once or twice weekly administration, once every two weeks, once every three weeks, once every four weeks, once a month, once every two or three months or once every three to 6 months. Dosages may be selected and readjusted by the skilled health care professional as required to maximize therapeutic benefit for a particular subject, e.g., patient. TfR specific binding compounds will typically be administered on multiple occasions. Intervals between single dosages can be, for example, 2-5 days, weekly, monthly, every two or three months, every six months, or yearly. Intervals between administrations can also be irregular, based on regulating blood levels of TfR specific binding compound to the target TfR ligand in the subject or patient. In some methods, dosage is adjusted to achieve a plasma antagonist concentration of about 1-1000 µg/ml and in some methods about 25-300 µg/ml. Dosage regimens for a TfR specific binding compound of the invention include intravenous administration of 1 mg/kg body weight or 3 mg/kg body weight with the compound administered every two to four weeks for six dosages, then every three months at 3 mg/kg body weight or 1 mg/kg body weight.

In certain embodiments, two or more TfR specific binding compounds with different binding properties may be administered simultaneously or sequentially, in which case the dosage of each administered compound may be adjusted to fall within the ranges described herein.

In certain embodiments, a TfR specific binding compound of the invention may be administered as a sustained release formulation, in which case less frequent administration is required. Dosage and frequency vary depending on the half-life of the TfR specific binding compound in the subject or patient. The dosage and frequency of administration may vary depending on whether the treatment is therapeutic or prophylactic (e.g., preventative), and may be adjusted during the course of treatment. In certain prophylactic applications, a relatively low dosage is administered at relatively infrequent intervals over a relatively long period of time. Some subjects may continue to receive treatment over their lifetime. In certain therapeutic applications, a relatively high dosage at relatively short intervals is sometimes required until progression of the disease is reduced or until the patient shows partial or complete amelioration of symptoms of disease. Thereafter, the patient may be switched to a suitable prophylactic dosing regimen.

Actual dosage levels of the TfR specific binding compound alone or in combination with one or more other active ingredients in the pharmaceutical compositions of the present invention may be varied so as to obtain an amount of the active ingredient which is effective to achieve the desired therapeutic response for a particular patient, composition, and mode of administration, without causing deleterious side effects to the subject or patient. A selected dosage level will depend upon a variety of factors, such as pharmacokinetic factors, including the activity of the particular TfR specific binding compound or composition employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the subject or patient being treated, and similar factors well known in the medical arts.

Administration of a "therapeutically effective dosage" of a TfR-binding compound of the invention may result in a decrease in severity of disease symptoms, an increase in frequency and duration of disease symptom-free periods, or a prevention of impairment or disability due to the disease affliction.

A TfR specific binding compound or composition of the present invention may be administered via one or more routes of administration, using one or more of a variety of methods known in the art. As will be appreciated by the skilled worker, the route and/or mode of administration will vary depending upon the desired results. Routes of administration for TfR specific binding compounds or compositions of the invention include, e.g., intravenous, intramuscular, intradermal, intraperitoneal, subcutaneous, spinal or other parenteral routes of administration, for example by injection or infusion. The phrase "parenteral administration" as used herein refers to modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

In other embodiments, a TfR specific binding compound or composition of the invention may be administered by a non-parenteral route, such as a topical, epidermal or mucosal route of administration, for example, intranasally, orally, vaginally, rectally, sublingually or topically.

As described elsewhere herein, an active TfR specific binding compound may be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Sustained and Controlled Release Drug Delivery Systems, J. R. Robinson, ed., Marcel Dekker, Inc., New York, 1978.

Therapeutic compounds or compositions of the invention may be administered with one or more of a variety of medical devices known in the art. For example, in one embodiment, a therapeutic TfR specific binding composition of the invention may be administered with a needleless hypodermic injection device. Examples of well-known implants and modules useful in the present invention are in the art, including e.g., implantable micro-infusion pumps for controlled rate delivery; devices for administering through the skin; infusion pumps for delivery at a precise infusion rate; variable flow implantable infusion devices for continuous drug delivery; and osmotic drug delivery systems. These and other such implants, delivery systems, and modules are known to those skilled in the art.

In certain embodiments, the TfR specific binding compound or composition of the invention may be formulated to ensure a desired distribution in vivo. For example, the blood-brain barrier (BBB) excludes many highly hydrophilic compounds. To target a therapeutic compound or composition of the invention to a particular in vivo location, they can be formulated, for example, in liposomes which may comprise one or more moieties that are selectively transported into specific cells or organs, thus enhancing targeted drug delivery. Exemplary targeting moieties include folate or biotin; mannosides; antibodies; surfactant protein A receptor; p120 and the like.

Kits for Detecting or Quantifying TfR in a Sample

Also, within the scope of the invention are kits comprising at least one TfR specific binding moiety or TfR specific binding compound or composition of the invention, and optionally, instructions for use. Kits may be useful for quantifying TfR or TfR specific antibodies in a sample, or may be useful for detection of TfR, such as in diagnostics methods. The kit may further or alternatively comprise at least one nucleic acid encoding a TfR specific binding moiety of the invention. A kit of the invention may optionally comprise at least one additional reagent (e.g., standards, markers and the like). Kits typically include a label indicating the intended use of the contents of the kit. The kit may further comprise reagents and other tools for measuring TfR in a sample or in a subject, or for diagnosing whether a patient belongs to a group that responds to a TfR-specific binding compound which makes use of a compound, composition or related method of the invention as described herein.

Delivery Devices and Further Kits

In certain embodiments, the invention relates to a device comprising one or more UR specific binding compounds of the invention, or pharmaceutically acceptable salts or solvates thereof, for delivery to a subject. Thus, one or more compounds of the invention or pharmaceutically acceptable salts or solvates thereof can be administered to a patient in accordance with the present invention via a variety of delivery methods, including: intravenous, subcutaneous, intramuscular or intraperitoneal injection; oral administration; transdermal administration; pulmonary or transmucosal administration; administration by implant, osmotic pump, cartridge or micro pump; or by other means recognized by a person of skill in the art.

In some embodiments, the invention relates to a kit comprising one or more peptides, or pharmaceutically acceptable salts or solvates thereof, of the invention. In other embodiments, the kit comprises one or more pharmaceutical compositions comprising one or more peptides or pharmaceutically acceptable salts or solvates thereof. In certain embodiments, the kit further comprises packaging and/or instructions for use.

While some embodiments of the invention have been described by way of illustration, it will be apparent that the invention can be put into practice with many modifications, variations and adaptations, and with the use of numerous equivalents or alternative solutions that are within the scope of persons skilled in the art, without departing from the spirit of the invention or exceeding the scope of the claims.

All publications, patents, and patent applications are herein incorporated by reference in their entirety to the same extent as if each individual publication, patent or patent application was specifically and individually indicated to be incorporated by reference in its entirety.

EXAMPLES

The examples presented herein represent certain embodiments of the present invention. However, it is to be understood that these examples are for illustration purposes only and do not intend, nor should any be construed, to be wholly definitive as to conditions and scope of this invention. The examples were carried out using standard techniques, which are well known and routine to those of skill in the art, except where otherwise described in detail.

Example 1. Phenotypic Selection for In Vitro BBB Penetrant VNARs to Human TfR-1

Semi-synthetic Type I and Type II VNAR phage libraries (OsX-4 and OsX-3, respectively described in WO2015/

200883) were subjected to two rounds of in vitro biopanning on recombinant human TfR-1 ecto-domain (Sinobiological) as described in WO2018/031424 (Example 1). The resulting mixed pool of phage clones enriched for human TfR-1 binders was amplified and endotoxins were removed by Triton X-114 phase separation (Aida Y, Pabst M J: Removal of endotoxin from protein solutions by phase separation using Triton X-114. J Immunol Methods 1990, 132:191-195). The cleaned phage preparation was resuspended in sterile PBS and tittered.

Human hCMEC/D3 cells were seeded in flasks pre-coated with rat tail collagen type 1 (0.1 mg/ml) in endothelial basal medium (EBM-2) supplemented with recombinant human fibroblast growth factor, fetal bovine serum, long R3-insulin-like growth factor, vascular endothelial growth factor, recombinant human epidermal growth factor and hydrocortisone (EGM™-2 MV BulletKit™, Lonza). Cultures were maintained at 37° C. in 5% $CO_2$ and the cell medium was changed every 2-3 days.

For transcytosis, hCMEC/D3 cells were grow in flasks to 80-90% confluence before plating onto the 12-well Transwells® (Corning, 0.4 μm polyester membrane). For plating, the upper side of the Transwell filter was pre-coated with 0.1 mg/ml rat tail collagen type 1 for 2 hours and washed with PBS containing magnesium and calcium. Cells were seeded in top (apical) chambers at a density of ~25,000 cells/cm² in 0.5 ml of cell medium and 1.5 ml of medium was added to basolateral chambers. Formation of the endothelial barrier was monitored by measuring trans-endothelial electric resistance (TEER) using an XTX10 electrode connected to an epithelial volt/ohm meter (EVOM2, World Precision Instruments).

Medium containing $10^{11}$ cfu/ml of phage particles was added to the upper chamber of Transwells with hCMEC/D3 cells grown for 8 days, when TEER reached ~20 Ωcm2 and permeability of 40 kDa FITC-Dextran decreased to ~0.2× $10^{-3}$ cm/min. The cells were returned to the incubator and cultured for 1 h or 3 h. After that time, the medium from the bottom Transwell chamber was collected and used to infect a log phase culture of ER2738 *E. coli*. After one hour of culture, the bacteria were plated onto large bio-assay agar plates (2TY medium with glucose and ampicillin). The following day the bacterial colonies were scraped and pooled and an aliquot used to rescue the phages. This selection process was repeated two additional times (FIG. 1).

After the third round of selection, instead of pooling bacterial colonies, individual phagemid clones were grown in 1 ml of 2TY medium containing glucose and ampicillin in 96-well blocks and used to rescue the phages. After an overnight culturing, bacteria were spun down and an aliquot of the phage supernatant was sent for Sanger sequencing (Genewiz); VNAR CDR3 sequences were identified using BioEdit (a sequence alignment editor). Another aliquot was blocked with 2.5% milk for phage ELISAs. High-binding ELISA plates (Greiner) were coated with 1 μg/ml of recombinant human or mouse TfR-1. The plates were then blocked with 2.5% milk in PBST. Blocked phages were added to the blocked plates and the VNAR-phage clones binding to the antigens were detected with HRP-labelled anti-M13 coat protein antibodies (Sino Biological), and chromogenic TMB substrate (KLM)

Figure 2A:
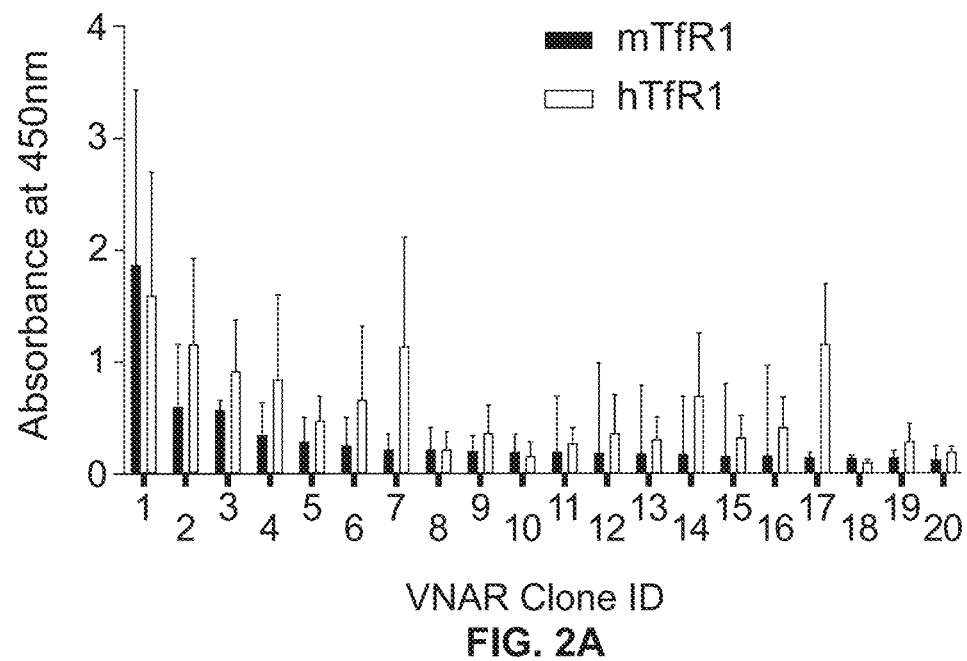
FIG. 2. Binding of selected VNAR phage clones to mouse and human TfR-1. Individual phage clones selected as described in FIG. 1 were analyzed by phage ELISA against mouse and human TfR-1. The top 60 clones are shown and ordered by signal obtained in the mouse TfR-1-binding ELISA. Clones 32 through 60 are considered as non-binding to mouse TfR-1. The corresponding VNAR domain amino acid sequence for each Clone ID is provided in Table 1.
Figure 2B:
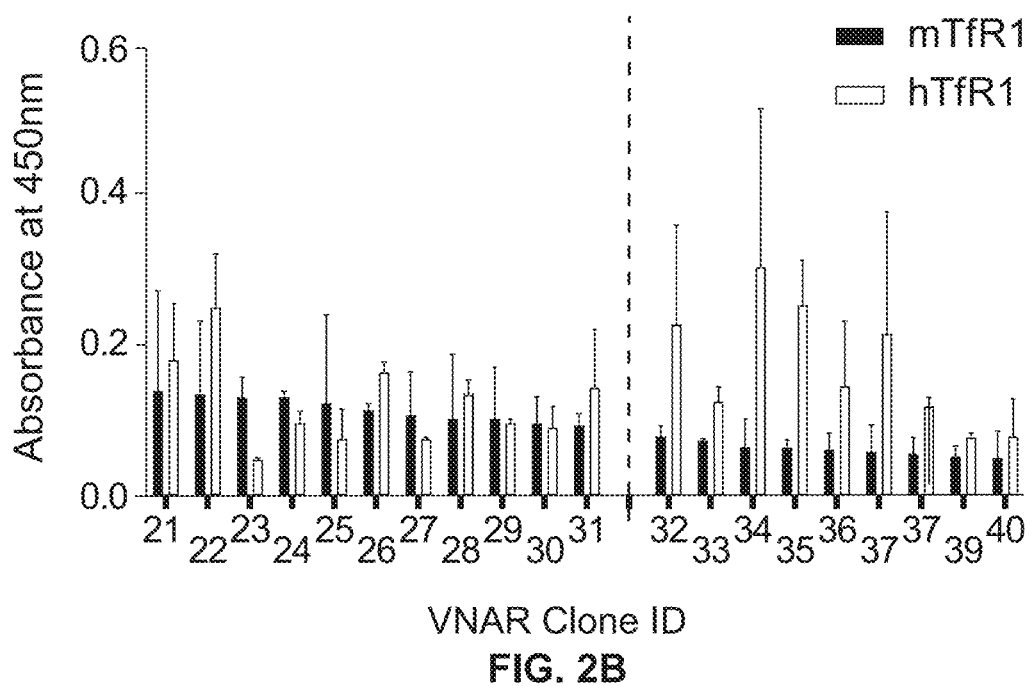
Figure 2C:
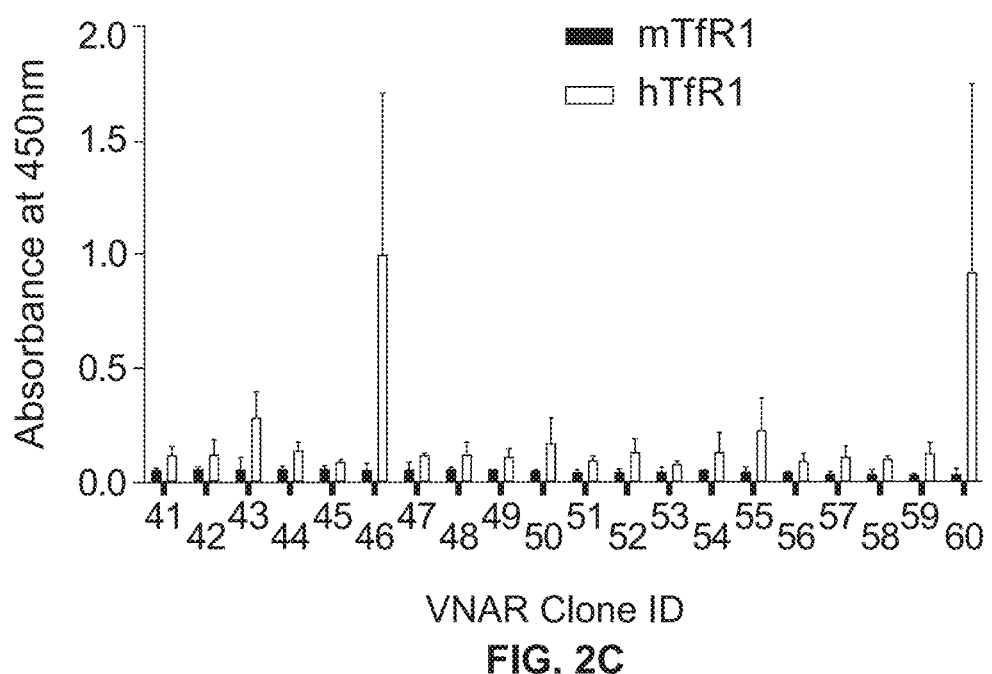

The deduced amino acid sequence of the 85 unique TfR1-binding VNARs selected by transcytosis on hCMEC/D3 cells is shown in Table 1. CDR3 lengths ranged from 11 to 27 amino acids and six of these VNARs were the Type I isoform, which contain 2 additional disulphide bridges. The remainder were Type II which have a disulphide bridge linking CDR3 to CDR1. As shown in FIG. 2, 31 clones showed significant binding to mouse TfR-1 (greater than 2× the background signal); of these, the majority of clones were cross-reactive with human TfR-1.

TABLE 1

Amino acid sequence of the TfR1-binding VNARs

| Clone ID | FW1 | CDR1 | FW2/3 | CDR3 | FW4 | Type | S# |
|---|---|---|---|---|---|---|---|
| 1 | ARVDQTPQTITKE TGESLTINCVLR | DNNCALS | TTYWYRKKSGSTNEESIS LGGRYVETVNSGSKSFSL RINDLTVEDSGTYRCNV | SDVVSCDDGW NWLDV | YGGGTAVTVNA | II | 14 |
| 2 | ARVDQTPQTITKE TGESLTINCVLR | DSNCELS | STYWYRKKSDSTNEASIS KGGRYVETVNSGSKSFSL KINDLTVEDSGTYRCNV | FTSDSYDLGD V | YGGGTVVTVNA | II | 15 |
| 3 | ARVDQTPQTITKE TGESLTINCVLR | DSNCALP | STYWYRKKSGSTNEESIS KGGRYVETVNSGSKSFSL RINDLTVKDSGTYRCNV | VQEPYSCKGR DDV | YGGGTAVTVNA | II | 16 |
| 4 | ARVDQTPQTITKE TGESLTINCVLR | DSNCALP | STYWYRKKSGSTNEESIS KGGRYVETVNSGSKSFSL RINDLTVKDSGTYRCKV | MSQEVRWQMT CKIVVMDV | YGGGTVVTVNA | II | 17 |
| 5 | ARVDQTPQTITKE TGESLTINCVLR | DSNCALS | STLWYRTKSGSRNEESIS KGGRYVETVNSGSKSFSL RINDLTVKDSGTYRCNV | QQYDCIASFD V | YGDGTAVTVNA | II | 18 |
| 6 | ARVDQTPQTVTKE TGESLTINCVLR | DSNCALS | STLWYRTKSGSRNEESIS KGGRYVETVNSGSKSFSL RINDLTVEDSGTYRCNV | CSNYCPIKDD V | YGDGTAVTVNA | II | 19 |
| 7 | ARVDQTPQTITKE TGESLTINCVLR | DNNCALS | STLWYRTKSGSRNEESIS KGGRYVETVNSGSKSFSL RINDLTVEDSGTYRCNV | QSWPPGNGWW CDV | YGDGTAVTVNA | II | 20 |

TABLE 1-continued

Amino acid sequence of the TfR1-binding VNARs

| Clone ID | FW1 | CDR1 | FW2/3 | CDR3 | FW4 | Type | S# |
|---|---|---|---|---|---|---|---|
| 8 | ARVDQTPQTITKE TGESLTINCVLR | DSNCALP | STYWYRKKSGSTNEESIS KGGRYVETVNSGSKSFSL RINDLTVEDSGTYRCKV | IAQLSSILRG CNYRKHDV | YGDGTAVTVNA | II | 7 |
| 9 | ARVDQTPQTITKE TGESLTINCVLR | DSNCALP | STWYRKKSDSTNEESISK GGRYVETVNSGSKSFSLR INDLTVKDSGTYRCKV | LYPNCYRCMW GQVTDV | YGGGTAVTVNA | II | 21 |
| 10 | ARVDQTPQTITKE TGESLTINCVLR | DSNCALS | NLYWYRKKSGSTNEESIS LGGRYVETVNSGSKSFSL RINDLTVEDSGTYRCNV | VQYPTAKCRQ VDV | YGGGTAVTVNA | II | 22 |
| 11 | ARVDQTPQTITKE TGESLTINCVLR | DSNCALP | STYWYRKKSGSTNEESIS KGGRYVETVNSGSKSFSL RINDLTVEDSGTYRCNV | QWLWSFSCLP CVEDV | YGGGTVVTVNA | II | 23 |
| 12 | ARVDQTPRSVTKE TGESLTINCVLR | DASYELG | STCWYRKKSGSTNEESIS KGGRYVETVNSGSKSFSL RINDLTVEDGGTYRCGA | WSRLSSSWGC DVGLQCMGCW DLWAA | CGDGTAVTVNA | I | 24 |
| 13 | ARVDQTPQTITKQ TGESLTINCVLR | DSNCALS | STYWYRKKSGSTNEESIS LGGRYVETVNSGSKSFSL RINDLTVEDSGTYRCNV | RRLQAWGSCR GGDV | YGGGTVVTVNA | II | 25 |
| 14 | ARVDQTPQTITKE TGESLTINCVLR | DSNCALP | STYWYRKKSGSTNEESIS KGGRYVETVNSGSKSFSL RINDLTVKDSGTYRCNV | MVFQVSGDYS RLEDV | YGGGTVVTVNA | II | 26 |
| 15 | ARVDQTPRSVTKE TGESLTINCVLR | DASYELG | STCWYRKKSGSTNEESIS KGGRYVETVNSGSKSFSL RINDLTVEDGGTYRCGA | PRWQMGGQWC DGGTAACRSG MAEVAA | CGDGTAVTVNA | I | 27 |
| 16 | ARVDQTPQTITKE TGESLTINCVLR | DSNCALS | STYWYRKKSGSTNEENIS KGGRYVETVNSGSKSFSL RINDLTVEDSGTYRCKV | QSAQGMGLNG CKPGRVDV | YGDGTAVTVNA | II | 28 |
| 17 | ARVDQTPQTITKE TGESLTINCVLR | DSNCALS | NLYWYRKKSGSTNEESIS LGGRYVETVNSGSKSFSL RINDITVEDSGRYRCNV | YNFFTYQCRW FQSDV | YGDGTAVTVNA | II | 29 |
| 18 | ARVDQTPQTITKE TGESLTINCVLR | DSNCALS | STYWYRKKSDSTNEESIS KGGRYVETVNSGSKSFSL RINDLTVEDSGTYRCKV | CTGMSCPCLG RRQTDV | YGGGTAVTVNA | II | 30 |
| 19 | ARVDQTPQTITKE TGESLTINCVLR | DSNCALS | STYWYRKKSGSTNEESIS KGGRYVETVNSGSKSFSL RINDLTVEDSGTYRCNVG | QAQRLRSNVD DV | YGGGTVVTVNA | II | 31 |
| 20 | ARVDQTPRSVTKE TGESLTINCVLR | DSNCALP | STYWYRKKSGSTNEESIS KGGRYVETVNSGSKSFSL RINDLTVKDSGTYRCNV | KWDCRYQCIC VSADV | YGDGTAVTVNA | II | 32 |
| 21 | ARVDQTPRVTKET GESLTINCVLR | DNNCALS | TTYWYRKKSGSTNEENIS KGGRYVETVNSGSKSFSL RINDLTVEDSGTYRCNV | YMTACSNDMD V | YGGGTVVTVNA | II | 33 |
| 22 | ARVDQTPQTITKE TGESLTINCVLR | DSNCALS | NLYWYRKKSGSTNEESIS LGGRYVETVNSGSKSFSL RINDLTVEDSGTYRCNV | QQQSSGTFYD V | YGGGTAVTVNA | II | 34 |
| 23 | ARVDQTPQTVTKE TGESLTINCVLR | DSNCDLS | RTYWYRKKSGSTNEESIS KGGRYVETVNSGSKSFSL RINDLTVEDSGTYRCNV | GGDLCGDQRD V | YGGGTAVTVNA | II | 35 |
| 24 | ARVDQTPQTITKE TGESLTINCVLR | DSNCALP | STYWYRKKSGSTNEESIS KGGRYVETVNSGSKSFSL RINDLTVKDSGTYRCKV | GPRCMGPNWQ SYSCDV | YGGGTVVTVNA | II | 36 |
| 25 | ARVDQTPRSVTKE TGESLTINCVLR | DSICALS | STYWYRKKSGSTNEESIS KGGRYVETVNSGSKSFSL KINDLTVEDSGTYRCNV | FTEMRGRCWA WGVDV | YGDGTAVTVNA | II | 37 |

TABLE 1-continued

Amino acid sequence of the TfR1-binding VNARs

| Clone ID | FW1 | CDR1 | FW2/3 | CDR3 | FW4 | Type | S# |
|---|---|---|---|---|---|---|---|
| 26 | ARVDQTPQTITKE TGESLTINCVLR | DSNCALS | STLWYRTKSGSRNEESIS KGGRYVETVNSGSKSFSL KINDLTVEDSGTYRCNV | CMGVTCNHVP DV | YGGGTVVTVNA | II | 38 |
| 27 | ARVDQTPRSVTKE TGESLTINCVLR | DASYALG | STCWYRKKSGSTNEESIS KGGRYVETVNSGSKSFSL RINDLTVEDSGTYRCNV | SRIGQYLCQA RSDV | YGDGTAVTVNA | I | 39 |
| 28 | ARVDQTPQTITKE TGESLTINCVLR | DSICALS | STHWYRKKSGSTNEESIS KGGRYVETVNSGSKSFSL RINDLTVEDSGTYRCNV | RTAQGTLCGD VSDV | YGDGTAVTVNA | II | 40 |
| 29 | ARVDQTPQTITKE TGESLTINCVLR | DSNCALS | STLWYRTKSGSRNEESIS KGGRYVETVNSGSKSFSL RINDLTVEDSGTYRCNV | QQGCESYNWM VDV | YGGGTAVTVNA | II | 41 |
| 30 | ARVDQTPQTITKE TGESLTINCVLR | DSNCALS | STLWYRTKSGSRNEESIS KGGRYVETVNSGSKSFSL KINDLTVEDSGTYRCNV | WFADYYWFQY DV | YGGGTAVTVNA | II | 42 |
| 31 | ARVDQTPQTITKE TGESLTINCVLR | DSNCALS | STYWYRKKSDSTNEENIS KGGRYVETVNSGSKSFSL KINDLTVEDSGTYRCNV | QPLFCDLWLD V | YGGGTVVTVNA | II | 43 |
| 32 | ARVDQTPQTITKE TGESLTINCVLR | DSNCALS | STYWYRKKSGSTNEENIS KGGRYVETVNSGSKSFSL RINDLTVEDSGTYRCNV | QDMLTPNDGQ LWDV | YGDGTAVTVNA | II | 44 |
| 33 | PRVDQTPQTITKE TGESLTINCVLR | DSNCALS | NLYWYRKKSGSTNEESIS KGGRYVETVNSGSKSFSL RINDLTVEDSGTYRCNV | LVGMLSGCGF QRGDV | YGGGTAVTVNA | II | 45 |
| 34 | PRVDQTPQTITKE TGESLTINCVLR | DSNCALS | STYWYRKKSGSTNEESIS KGGRYVETVNSGSKSFSL RINDLTVEDSGTYRCNV | SSNAHCDGRR RDV | YGGGTAVTVNA | II | 46 |
| 35 | ARVDQTPQTITKE TGESLTINCVLR | DSNCALS | STYWYRKKSDSTNEESIS KGGRYVETVNSGSKSFSL RINDLTVKDSGTYRCNV | SEDLQAICCW NDV | YGDGTAVTVNA | II | 47 |
| 36 | ARVDQTPQTITKE TGESLTINCVLR | DSNCALP | STYWYRKKSGSTNEESIS KGGRYVETVNSGSKSFSL RINDLVVEDSGTYRCNV | HCYGGDLHQL DV | YGGGTAVTVNA | II | 48 |
| 37 | ARVDQTPQTITKE TGESLTINCVLR | DSNCALS | STYWYRKKSDSTNEESIS KGGRYVETVNSGSKSFSL RINDLTVKDSGTYRCNV | SEDLQAICCW NDV | YGDGTAVTVNA | II | 47 |
| 38 | ARVDQTPQTITKE TGESLTINCVLR | DSNCALP | STYWYRKKSGSTNEESIS KGGRYVETVNSGSKSFSL KINDLTVEDSGTYRCNV | RIIQCCVSQD V | YGGGTVVTVNA | II | 49 |
| 39 | ARVDQTPQTITKE TGESLTINCVLR | DSNCELS | STYWYRKKSGSTNEESIS LGGRYVETVNSGSKSFSL RINDLTVEDSGTYRCNV | QSAMLMLCLS RFDV | YGGGTVVTVNA | II | 50 |
| 40 | ARVDQTPQTITKE TGESLTINCVLR | DSNCALS | STYWYRKKSGSTNEESIS KGGRYVETVNSGSKSFSL RINDLTVEDSGTYRCKV | VQFEKDCQGL LRQTNDV | YGGGTVVTVNA | II | 51 |
| 41 | ARVDQTPQTITKE TGESLTINCVLR | DSNCALS | NLYWYRKKSGSTNEESIS LGGRYVETVNSGSKSFSL RINDLTVEDSGTYRCKV | TCEVALQPYY GQEPTQDV | YGGGTVVTVNA | II | 52 |
| 42 | ARVDQTPQTITKE TGESLTINCVLR | DSNCELS | STYWYRKKSGSTNEARIS KGGRYVETVNSGSKSFSL RINDLTVEDSGTYRCKV | RKALVQSQSC CQPLHRDV | YGDGTAVTVNA | II | 53 |
| 43 | ARVDQTPQTITKE TGESLTINCVLR | DSNCALP | STYWYRKKSGSTNEESIS KGGRYVETVNSGSKSFSL RINDLTVEDSGTYRCNV | SDFMWESCSQ DV | YGGGTAVTVNA | II | 54 |
| 44 | ARVDQTPRSVTKE TGESLTINCVLR | DASYELG | STCWYRKKSGSTNEESIS KGGRYVETVNSGSKSFSL RINDLTVEDGGTYRCGA | GSVQRSTSQC DRLWSRCWRT RFKIAA | CGDGTAVTVNA | II | 55 |

TABLE 1-continued

Amino acid sequence of the TfR1-binding VNARs

| Clone ID | FW1 | CDR1 | FW2/3 | CDR3 | FW4 | Type | S# |
|---|---|---|---|---|---|---|---|
| 45 | AVDQTPQTITKET GESLTINCVLR | DSNCALS | NLYWYRKKSDSTNEESIS KGGRYVETVNSGSKSFSL RINDLTVEDSGTYRCNV | CWWFSSRCTT CDV | YGDGTAVTVNA | II | 56 |
| 46 | ARVDQTPRVTKET GESLTINCVLR | DASYELG | STCWYRKKSGSTNEESIS KGGRYVETVNSGSKSFSL RINDLTVEDGGTYRCGA | SGSQGQVYRC DRLTLCCLQM QWQVAA | CGDGTAVTVNA | II | 57 |
| 47 | PRVDQTPQTITKE TGESLTINCVLR | DSNCALP | STYWYRKKSGSTNEENIS KGGRYVETVNSGSKSFSL KINDLTVEDSGTYRCNV | IINPLSCYYL QLQDV | YGGGTAVTVNA | II | 58 |
| 48 | ARVDQTPRSVTKE TGESLTINCVLR | DASYELG | STCWYRKKSGSTNEESIS KGGRYVETVNSGSKSFSL RINDLTVEDGGTYRCGA | SFMLSHPGGC DSCVIMCQTR RQGVAA | CGDGTAVTVNA | I | 59 |
| 49 | ARVDQTPQTITKE TGESLTINCVLR | DSNCALP | STYWYRKKSGSTNEESIS KGGRYVETVNSGSKSFSL KINDLTVEDSGTYRCNV | QGRAAYSGLV CDV | YGGGTAVTVNA | II | 60 |
| 50 | ARVDQTPQTITKE TGESLTINCVLR | DSNCALP | STYWYRKKSDSTNEESIS KGGRYVETVNSGSKSFSL RINDLTVKDSGTYRCNV | LIQCCSPTCD V | YGGGTAVTVNA | II | 61 |
| 51 | ARVDQTPQTITKE TGESLTINCVLR | DSNCALS | STLWYRTKSGSRNEESIS KGGRYVETVNSGSKSFSL RINDLVVEDSGTYRCKV | SHSGLCQYCH DLEDDV | YGDGTAVTVNA | II | 62 |
| 52 | PRVDQTPQTITKE TGESLTINCVLR | DSNCALS | STYWYRKKSGSTNEENIS KGGRYVETVNSGSKSFSL RINDLTVEDSGTYRCNV | AFFACQYKND V | YGGGTVVTVNA | II | 63 |
| 53 | ARVDQTPQTITKE TGESLTINCVLR | DSNCALS | STYWYRKKSDSTNEESIS KGGRYVETVNSGSKSFSL RINDLTVEDSGTYRCNV | YLQDRPVCSP FNYDV | YGGGTAVTVNA | II | 64 |
| 54 | ARVDQTPQTITKE TGESLTINCVLR | DSNCALP | ITYWYRKKSGSTNEESIS KGGRYVETVNSGSKSFSL RINDLTVKDSGTYRCNV | GAQYCDREIS DV | YGDGTAVTVNA | II | 65 |
| 55 | PRVDQTPQTITKE TGESLTINCVLR | DSNCALS | STLWYRTKSGSRNEESIS KGGRYVETVNSGSKSFSL RINDLTVEDSGTYRCNV | WCLTLGCSGK WDV | YGGGTAVTVNA | II | 66 |
| 56 | ARVDQTPQTITKE TGESLTINCVLR | DSNCALS | STYWYRKKSDSTNEESIS KGGRYVETVNSGSKSFSL RINDLVVEDSGTYRCNV | QSKEKLHCQV VVDV | YGGGTAVTVNA | II | 67 |
| 57 | ARVDQTPQTITKE TGESLTINCVLR | DSNCALP | STYWYRKKSGSTNEESIS KGGRYVETVNSGSKSFSL RINDLTVEDSGTYRCNV | RGFKQCYDLR LDV | YGGGTAVTVNA | II | 68 |
| 58 | ARVDQTPQTITKE TGESLTINCVLR | DSNCELS | STYWYRKKSGSTNEARIS KGGRYVETVNSGSKSFSL RINDLTVEDSGTYRCNV | GFSQSWGNSV GIVDV | YGGGTAVTVNE | II | 69 |
| 59 | ARVDQTPQTITKE TGESLTINCVLR | DSNCALP | STYWYRKKSGSTNEESIS KGGRYVETVNSGSKSFSL RINDLTVEDSGTYRCNV | SLQFCCLSFD V | YGGGTAVTVNA | II | 70 |
| 60 | ARVDQTPQTITKE TGESLTINCVLR | DSNCDLS | RTYWYRKKSGSTNEESIS KGGRYVETVNSGSKSFSL RINDLTVEDSGTYRCNV | YNPGNGWAMY DV | YGGGTAVTVNA | II | 71 |
| 61 | ARVDQTPQTITKE TGESLTINCVLR | DSNCALS | STYWYRKKSDSTNEESIS KGGRYVETVNSGSKSFSL KINDLTVEDSGTYRCKV | LSVQRLFCAI FASEDV | YGDGTAVTVNA | II | 72 |
| 62 | ARVDQTPQTITKE TGESLTINCVLR | DSNCALS | STYQYRKKSGSTNEESIS KGGRYVETVNSGSKSFSL RINDLTVKDSGTYRCNV | LSVQRLFCAI FASEDV | YGDGTAVTVNA | II | 73 |

TABLE 1-continued

Amino acid sequence of the TfR1-binding VNARs

| Clone ID | FW1 | CDR1 | FW2/3 | CDR3 | FW4 | Type | S# |
|---|---|---|---|---|---|---|---|
| 63 | ARVDQTPQTITKE TGESLTINCVLR | DSNCALP | STYWYRKKSGSTNEESIS KGGRYVETVNSGSKSFSL KINDLTVEDSGTYRCKV | ANEYWLRLNQ CFYLQHDV | YGGGTVVTVNA | II | 74 |
| 64 | ARVDQTPQTITKE TGESLTINCVLR | DSNCALS | STYWYRKKSGSTNEESIS KGGRYVETVNSGSKSFSL RINDLTVEDSGTYRCNV | QLQFDCKEWE DV | YGGGTVVTVNA | II | 75 |
| 65 | ARVDQTPRSVTKE TGESLTINCVLR | DSICALS | STHWYRKKSGSTNEESIS KGGRYVETVNSGSKSFSL RINDLTVEDSGTYRCKV | TVTKWCCKQR DGCTGDV | YGGGTAVTVNA | II | 76 |
| 66 | ARVDQTPQTITKE TGESLTINCVLR | DSICALS | STHWYRKKSGSTNQESIS KGGRYVETVNSGSKSFSL RINDLTVEDSGTYRCNV | VQKGRIKCSR MLEDV | YGGGTVVTMNA | II | 77 |
| 67 | ARVDQTPQTITKE TGESLTINCVLR | DNNCASS | TTYWYRKKSGSTNEENIS KGGRYVETVNSGSKSFSL KINDLTVEDSGTYRCNV | RDVQACGNDW VWLDV | YGGGTVVTVNA | II | 78 |
| 68 | PRVDQTPQTITKE TGESLTINCVLR | DSNCALP | STYWYRKKSGSTNEESIS KGGRYVETVNSGSKSFSL RINDLTVEDSGTYRCNV | SGGRGGVCWQ GSDV | YGGGTVVTVNA | II | 79 |
| 69 | ARVDQTPQTITKE TGESLTINCVLR | DSNCALP | ITYWYRKKSGSTNEESIS KGGRYVETVNSGSKSFSL RINDLTVKDSGTYRCNV | PAQLLLYSGQ QGVDV | YGDGTVVTVNA | II | 80 |
| 70 | ARVDQTPQTITKE TGESLTINCVLR | DSNCALS | STYWYRKKSDSTNEESIS KGGRYVETVNSGSKSFSL RINDLTVKDSGTYRCNV | SEDLQAICCW NDV | YGDGTAVTVNA | II | 47 |
| 71 | ARVDQTPRSVTKE TGESLTINCVLR | DASYELG | STCWYRKKSGSTNEESIS KGGRYVETVNSGSKSFSL RINDLTVEDGGTYRCGA | LIQSHRNGRC DGWFDICPTS LGGAA | CGDGTAVTVNA | I | 81 |
| 72 | ARVDQTPQTVTKE TGESLTINCVLR | DSNCALP | STYWYRKKSGSTNEESIS KGGRYVETVNSGSKSFSL RINDLTVEDSGTYRCNV | IWLQVGVCDD YPYDV | YGDGTAVTVNA | II | 82 |
| 73 | ARVDQTPQTITKE TGESLTINCVLR | DSNCALP | STYWYRKKSGSTNEESIS KGGRYVETVNSGSKSFSL RINDLTVEDSGTYRCNV | DGWSLCQELC DV | YGGGTVVTVNT | II | 83 |
| 74 | ARVDQTPRSVTKE TGESLTINCVLR | DASYALG | STCWYRKKSGSTNEESIS KGGRYVETVNSGSKSFSL RINDLTVEDGGTYRCGV | SLRGKTMRGE CDYQVSVGLC GGQAAA | CGDGTAVTVNA | I | 84 |
| 75 | ARVDQTPQTITKE TGESLTINCVLR | DSNCALP | STYWYRKKSDSTNEESIS KGGRYVETVNSGSKSFSL RINDLVVEDSGTYRCNV | MRLERCRQNG DV | YGGGTAVTVNA | II | 85 |
| 76 | ARVDQTPQTVTKE TGESLTINCVLR | DSNCALS | NLYWYRKKSGSTNEESIS LGGRYVETVNSGSKSFSL KINDLTVEDSGTYRCNV | PALQVCCDGT QLDV | YGGGTAVTVNA | II | 86 |
| 77 | ARVDQTPQTITKE TGSLTINCVLR | DSNCDLS | RTYWYRKKSGSTNEESIS KGGRYVETVNSGSKSFSL RINDLVVEDSGTYRCNV | PVGHCCYCAG FDV | YGDGTVVTVNA | II | 87 |
| 78 | ARVDQTPQTITKE TGESLTINCVLR | DSNCALP | STYWYRKKSGSTNEESIS KGGRYVETVNSGSKSFSL RINDLTVKDSGTYRCNV | FILGQLYGYD YLDV | YGGGTAVTVNA | II | 88 |
| 79 | ARVDQTPQTITKE TGESLTINCVLR | DSNCALS | NLYWYRKKSGSTNEESIS LGGRYVETVNSGSKSFSL RINDLTVEDSGTYRCKV | SRRAQRLVSD DQSAWMDV | YGGGTVVTVNA | II | 89 |
| 80 | ARVDQTPQTITKE TGESLTINCVLR | DSNCALS | NLYWYRKKSGSTNEESIS KGGRYVETVNSGSKSFSL RINDLTVKDSGTYRCKV | GAERYKSSWQ CMGRSASDV | YGGGTVVTVNA | II | 90 |

TABLE 1-continued

Amino acid sequence of the TfR1-binding VNARs

| Clone ID | FW1 | CDR1 | FW2/3 | CDR3 | FW4 | Type | S# |
|---|---|---|---|---|---|---|---|
| 81 | ARVDQTPRSVTKE TGESLTINCVLR | DSNCDLS | RTYWYRKKSGSTNEESIS LGGRYVETVNSGSKSFSL RINDLTVEDSGTYRCNV | ECGTFGYSQC RDV | YGDGTAVTVNA | II | 91 |
| 82 | ARVDQTPQTITKE TGESLTINCVLR | DSNCDLS | RTYWYRKKSGSTNEESIS KGGRYVETVNSGSKSFSL RINDLVVEDSGTYRCNV | YNPSSYTSVC DV | YGGGTAVTVNA | II | 92 |
| 83 | ARVDQTPQTITKE TGESLTINCVLR | DSNCALP | STYWYRKKSGSTNEESIS KGGRYVETVNSGSKSFSL RINDLTVEDSGTYRCKV | MNKSYRCQRG LPLPRDV | YGDGTAVTVNA | II | 93 |
| 84 | ARVDQTPQTITKE TGESLTINCVLR | DSNCALS | NLYWYRKKSGSTNEESIS LGGRYVETVNSGSKSFSL KINDLTVEDSGTYRCNV | QLSNYYVDWY DV | YGGGTVVTVNA | II | 94 |
| 85 | ARVDQTPQTITKE TGESLTINCVLRA | DSNCELS | STYWYRKKSGSTNEARIS KGGRYVETVNSGSKSFSL RINDLTVEDSGTYRCNV | FAQRHCGYYR DV | YGDGTAVTVNA | II | 95 |

The column entitled "S #" provides the respective SEQ ID NO. for the full length of each of these 85 TfR1-binding VNARs in Table 1.

Example 2. Expression and Characterization of Selected VNAR Clones as Human Fc (hFc) Fusions VNAR clones that showed binding to mouse and human TfR-1 as VNAR-phage were cloned in frame as N-terminal fusions to the human IgG1-Fc in pFuse-hIgG1-Fc2 vector. The Fc region of the protein contained CH2 and CH3 domains engineered for the reduced ADCC and CDC. The cDNAs encoding the VNARs were synthesized and cloned using EcoRV and BglII restrictions site. In addition, the IgG hinge region was extended by incorporating a flexible linker sequences comprising glycine- and serine-rich residues $(GxSx)_n$, where x and n were typically from 0 to 4 (SEQ ID NO. 96). The IL2 secretory signal sequence (IL2Ss) of the parent plasmid was retained to allow secretion.

An HEK Expi293 expression system (Invitrogen) was used to transiently express the proteins. For these experiments, the VNAR-Fc fusions were expressed in small (1 ml) scale in 96-well plates according to manufacturer's protocol. For small scale expression, 425 µl of Expi293 cells at the concentration of $2.94 \times 10^6$/ml were plated into a 96-well block. Transfection was done by mixing 0.5 µg of each DNA with Opti-MEM media (Thermo) to make a total volume of 25 µl. Further, 1.35 µl of expifectamine was mixed with 23.65 µl Opti-MEM media and after 5 minutes added to the DNA mix; then incubated for an additional 25 minutes. The cells were grown in an incubator at 350 rpm, 37° C. with 8% $CO_2$ overnight before enhancer 1 (2.5 µl) and enhancer 2 (25 µl) were added and the cells grown for 5 more days.

The expression levels of individual clones were examined by human Fc-capture ELISA. Briefly, high-binding ELISA plates were coated overnight with a 1:500 dilution of goat α-human Fc antibody (Sigma). The plates were then blocked with 2.5% milk in PBST (PBS with 0.1% Tween20) for 1 hour at room temperature. After 4 days of expression, transfected cells were spun down at 2000 rpm for 10 minutes and the collected supernatant was mixed with milk in PBST to a final 2.5% concentration and incubated for 30 minutes. 100µl of blocked supernatant was transferred onto coated plates and incubated for 1 hour. After washing with PBST, bound VNAR-hFc was detected using a goat α-human Fc/HRP antibody (Sigma). The ELISA plates were developed using the chromogenic TMB substrate. Absorbance was measured at 450 nm. A VNAR-Fc at know concentration was used for standard curve to calculate VNAR-Fc expression level.

To confirm the binding ability of the VNAR-hFc fusions to mouse and human TfR-1, media was collected and used directly in a standard ELISA on Maxisorp™ plates (Nunc, Thermo) coated with 100 µl of 1 µg/ml of recombinant mouse TfR-1 (Sino 50741-M07H-100) or human TfR-1 (Sino 11020-H07H-100). The remainder of the assay was conducted as above.

Figure 3:
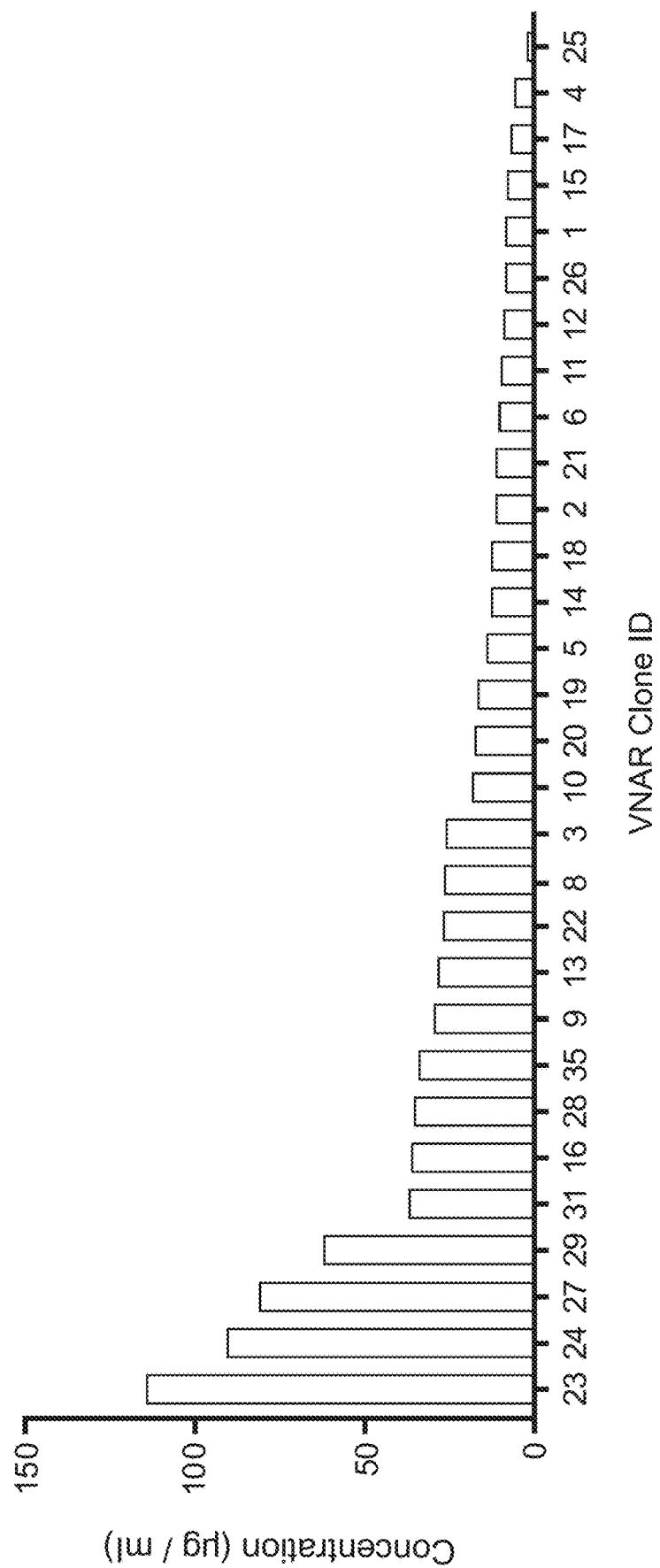
FIG. 3. VNAR-hFc expression levels. The VNAR domains from the 31 positive clones described in FIG. 2 fused to the human Fc domain were analyzed for expression levels by human Fc-capture ELISA after small scale transfection into Expi293F cells.
Figure 4:
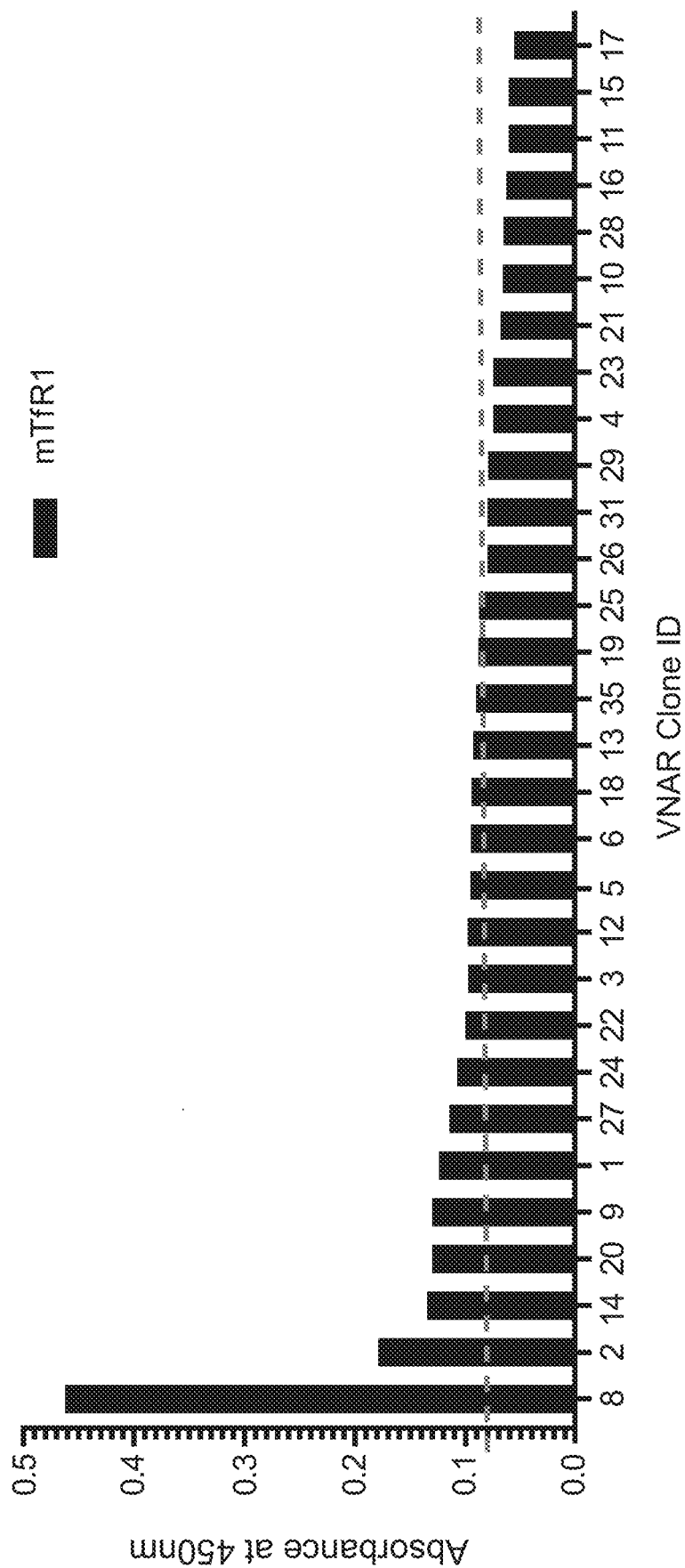
FIG. 4. Binding of VNAR-hFc fusions to mouse TfR-1. The fusions from the small-scale expression were analyzed for binding to mouse TfR-1 by ELISA. The dotted line shows absorbance of 0.08, the minimum value where clones are considered as positive mouse TfR-1 binders.
Figure 5:
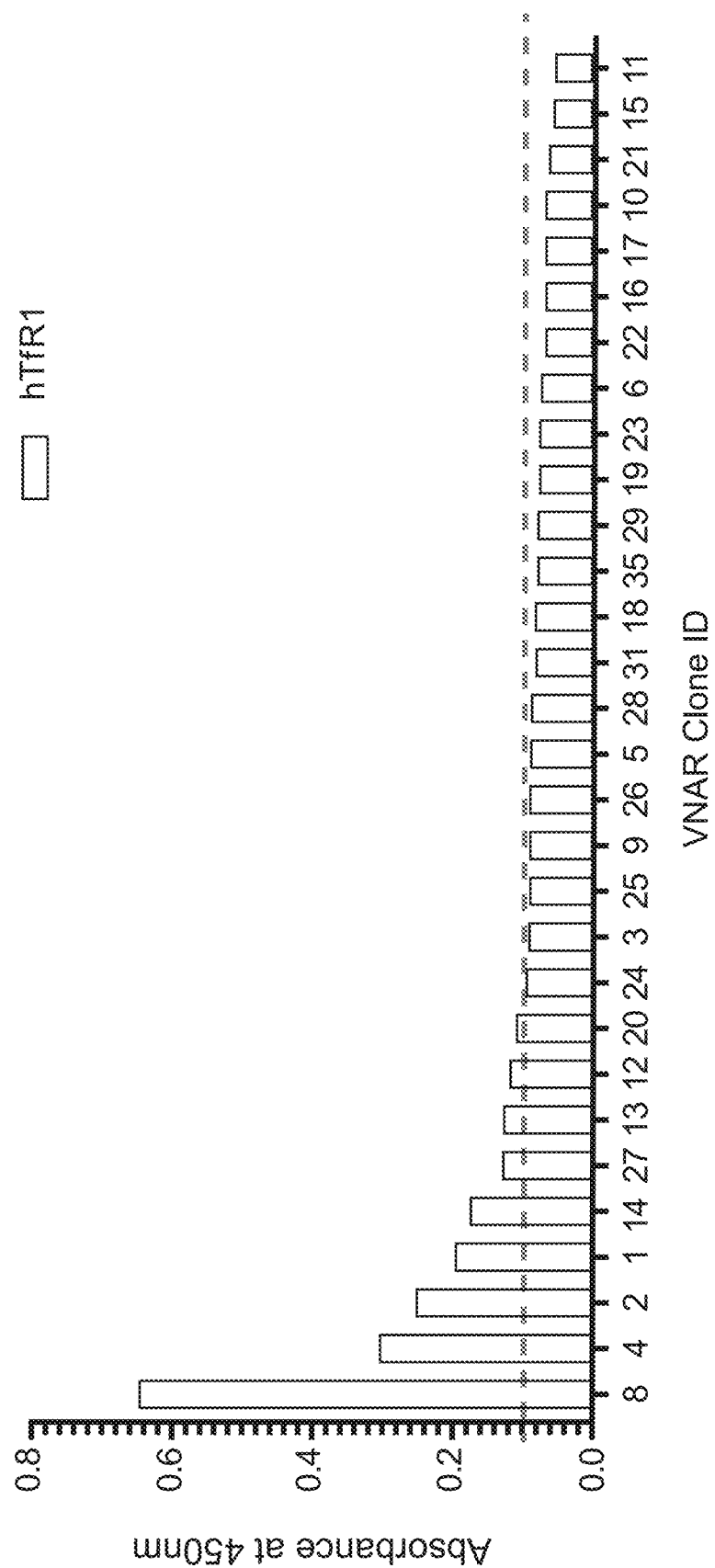
FIG. 5. Binding of VNAR-hFc fusions to human TfR-1. The fusions from the small-scale expression were analyzed for binding to human TfR-1 by ELISA. The dotted line shows absorbance of 0.08, the minimum value where clones are considered as positive human TfR-1 binders.

Expression levels are shown in FIG. 3 and were quite variable, ranging from 10 to 115 µg/ml. Only one clone was very poorly expressed. The VNAR-hFc proteins were tested for binding to human and mouse TfR-1 and FIGS. 4 and 5 show, that upon reformatting to hFc fusions, many clones appear to have lost target binding (with an A450 of 0.08 being the minimum value for clones to be considered binders). Clone 8, however, showed the strongest binding to both mouse and human TfR-1 and was followed in potency by Clone 2. Clone 4 bound to the human TfR-1 but not the mouse TfR-1.

Example 3. Brain Uptake of Selected VNAR Clones as Human Fc (hFc) Fusions

Based on their TfR-1 binding properties, nine VNAR-Fc fusion proteins were selected for testing brain shuttle activity in mice. The fusion proteins were expressed in 50 ml scale in expi293F cells and purified from medium using Protein A agarose bead slurry (Thermo Scientific) followed by buffer exchange to PBS using PD-10 column (GE).

For the large-scale expression, Expi293F (Invitrogen) cells were cultured in Expi293 expression medium (Invitrogen) supplemented with penicillin (100 U/ml), streptomycin (100 µg/ml) and maintained in a humidified shaking incubator at 37° C. and 5% $CO_2$. Cells were transfected using ExpiFectamine™ 293 Transfection Kit (Invitrogen) according to the manufacturer's protocol. Cells were removed from the expression medium by centrifugation 5 days post transfection, the media was filtered and mixed with a PBS-equilibrated slurry of MabSelect Sure (GE Life Sciences), and buffer exchanged followed by loading into PD-10 column and the recombinant protein eluted with a linear gradient of 0.1M glycine, pH 2.5 and PBS. Fractions containing the proteins were pooled and buffer exchanged to PBS using Sepadex 25 desalting columns (GE Life Sciences). Protein concentrations were estimated by absorbance at $280_{nm}$. Purified proteins were stored at −80° C. and once thawed maintained at 4° C. for a period of up to 2 weeks.

Balb/c mice (6-8 weeks) were injected intravenously with 12.5 nmol/kg (0.9375 mg/kg) of protein and a blood sample was taken after 18 h later. The animals were then perfused, and the brains were dissected and stored frozen. The whole brains were homogenized in 1% Triton X-100 and used for ELISA with anti-Fc capture and detection antibody. Standard curves were prepared individually for each of the molecules to assure accuracy of the calculated concentrations. R3D11 and 1A served as negative VNAR-Fc controls that bind at nM concentration to TfR-1 but lack a blood brain penetration property.

Figure 6:
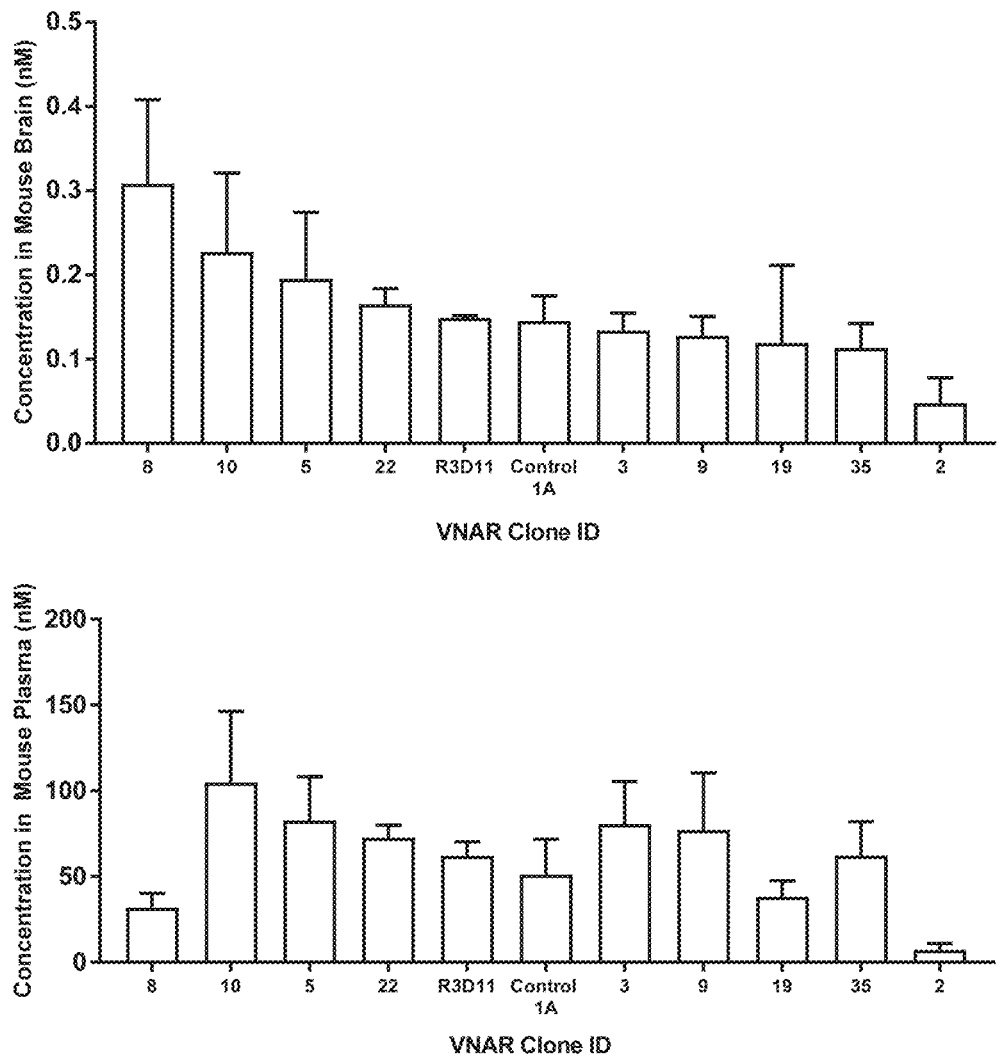
FIG. 6. Brain uptake of VNAR-Fc fusions. Selected VNAR-Fc fusions, indicated by Clone ID number, were tested for brain penetration in mice. VNAR-Fcs were administered intravenously in mice tail veins at 12.5 nmol/kg (0.9375 mg/kg) and brains were excised 18 hours later following cardiac perfusion. The VNAR-Fc concentration in brain homogenates (top panel) and plasma (bottom panel) was measured by human Fc-capture ELISA. R3D11 and 1A are control VNAR-hFc fusions that do not penetrate brain efficiently.
Figure 7:
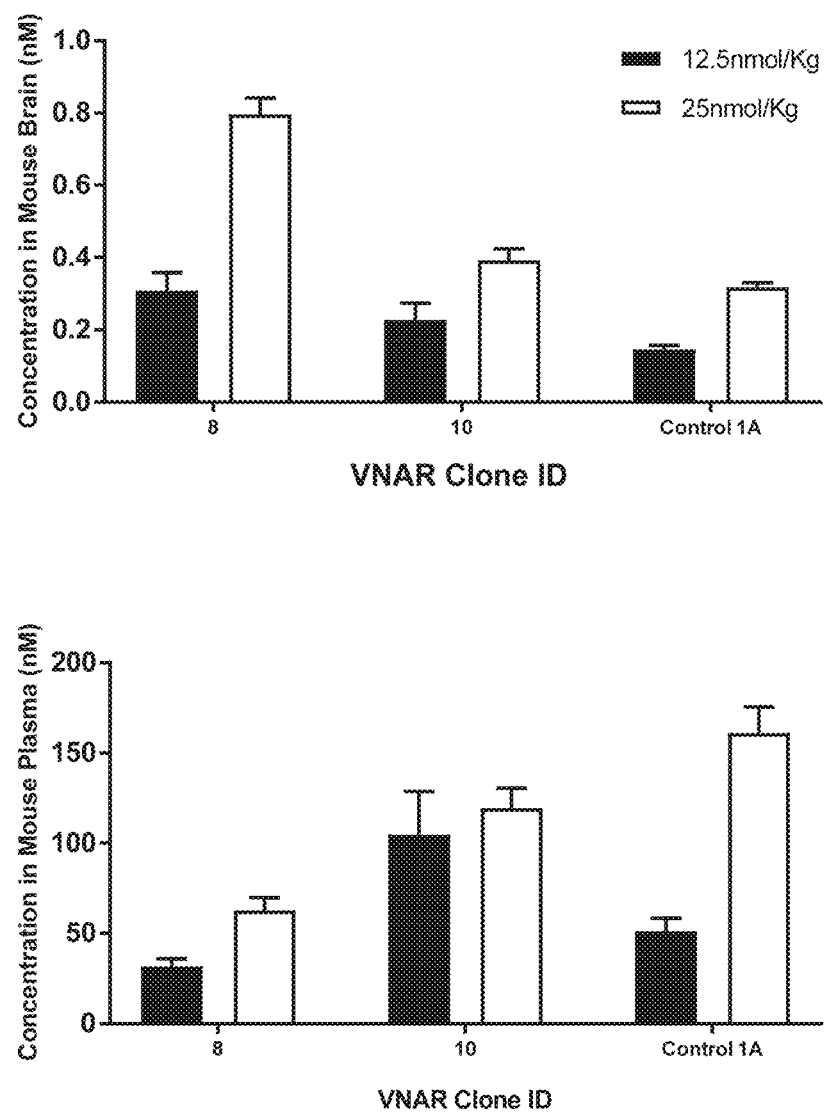
FIG. 7. Dose-dependent brain uptake of top two VNAR-Fc fusions. The VNAR-Fc fusions of Clone 8, Clone 10 and control 1A were administered intravenously in mice tail veins at doses of 12.5 nM/kg and 25 nM/kg and analyzed as in FIG. 7 for brain uptake (top panel) and plasma levels (bottom panel).

As shown in FIG. 6, top panel, Clone 8 and Clone 10 showed the best brain uptake, up to 2× better than that of the control VNAR-Fcs. Other VNAR-Fcs showed only moderate increase over the controls or no increase at all. Of the two brain-penetrant clones Clone 8 showed the lowest plasma levels 18 hours after dosing (FIG. 6, bottom panel). To determine if there was a dose-response relationship, the Clone 8 and Clone 10 Fc fusion proteins were injected intravenously into mice at 12.5 and 25 nmol/kg. Blood samples and brain homogenates were prepared as before. As shown in FIG. 7, Clone 8 showed a clear dose-dependent increase in both brain and in plasma.

Example 4. Restricted, Random Mutagenesis of Clone 8

The VNAR domain amino acid sequence for Clone 8 is:

(SEQ ID NO. 7)
ARVDQTPQTITKETGESLTINCVLR*DSNCALP*STYWYRKKSGSTNEESISK

GGRYVETVNSGS KSFSLRINDLTVEDSGTYRCKVIAQLSSILRGCNYRKH

DVYGDGTAVTVNA.

The CDR1 domain is bolded, underlined and italicized; the CDR3 domain is bolded and underlined.

To improve BBB shuttling function and binding specificity, the CDR3 region was subjected to a restricted randomization process. Seven different phage libraries were generated that each contained three contiguous randomly substituted amino acids (except for cysteine), which overlapped to cover the CDR3 region (FIG. 8). Omitting cysteine in the randomization process and maintaining cysteine at position 11, ensured retaining the Type 2 isoform structure. Additionally, the invariable DV dipeptide at the C-terminus of CDR3 was retained.

From over 48,000 variants generated, 184 clones were selected at random and the DNA was sequenced and analyzed. Of the 172 unambiguous sequences obtained, eight sequences were present more than once, including three instances where the clone had a sequence identical to the parent clone 8 (Table 2). Clones are ordered in order of highest apparent mouse TfR-1 binding in the phage ELISA.

Figure 9:
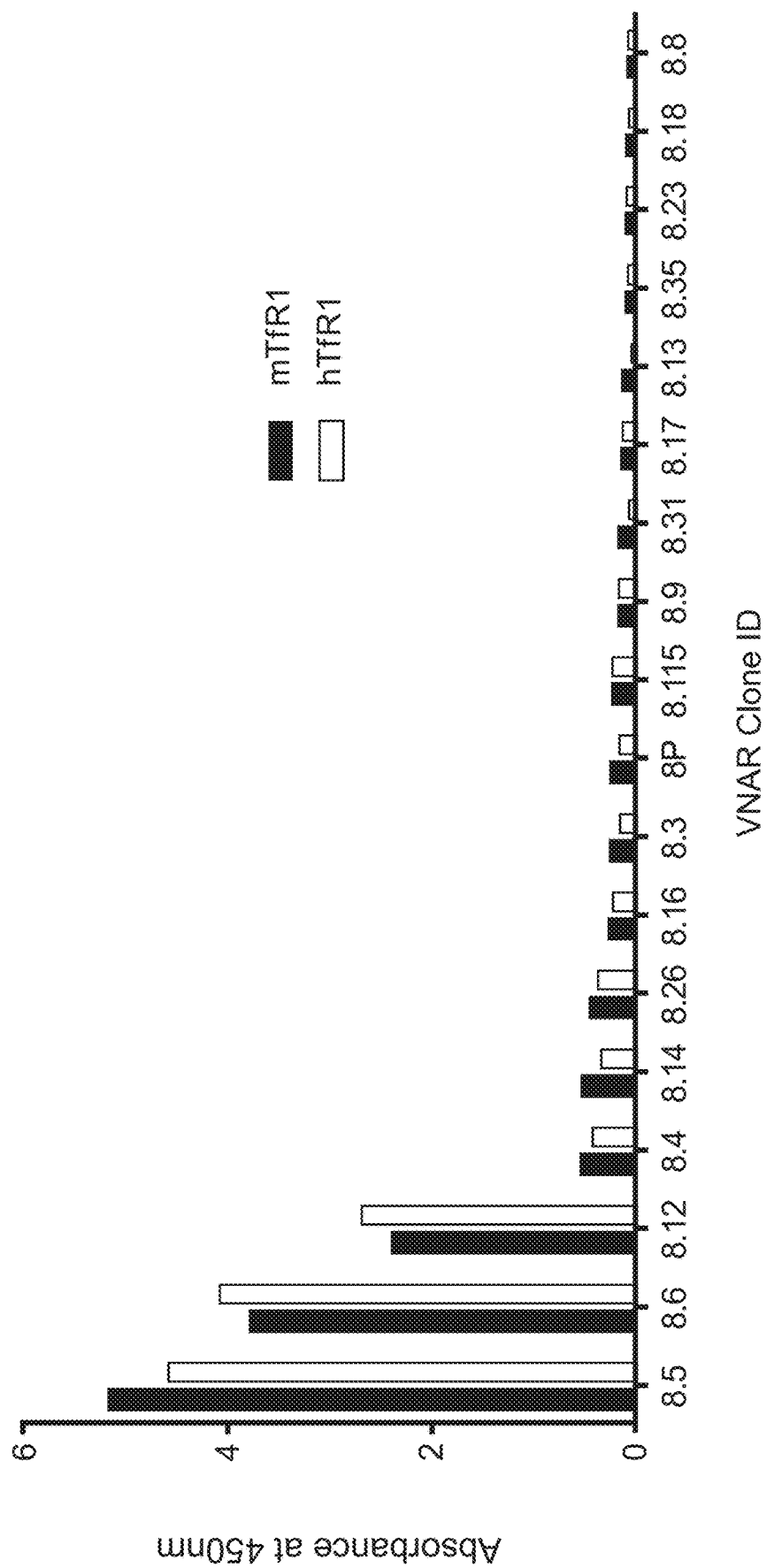
FIG. 9. Binding of selected Clone 8 variants to mouse and human TfR-1. This panel shows the binding of the top seventeen Clone 8 variants (by ID number) and Clone 8 (8P) to mouse and human TfR-1 as analyzed by phage ELISA. The clones are ordered by signal obtained in the mouse TfR1-binding ELISA. Binding was determined as an absorbance >0.08 for mouse TfR-1 and >0.1 for human TfR-1. The VNAR domain amino acid sequence for each variant is provided in Table 2.

The TfR-1 binding activity against human and mouse TfR-1 was assessed by phage ELISA and FIG. 9 shows the results for a subset of those clones. From the complete analysis, 41 out of 162 unique Clone 8 variants (25%) retained binding to mouse or human TfR1; 26 out of 162 (16%) retained binding to the mouse TfR1 and 14 out of 162 (8.6%) retained binding to human TfR1. A few of the variants appeared to be stronger binders than the original Clone 8.

Figure 10A:
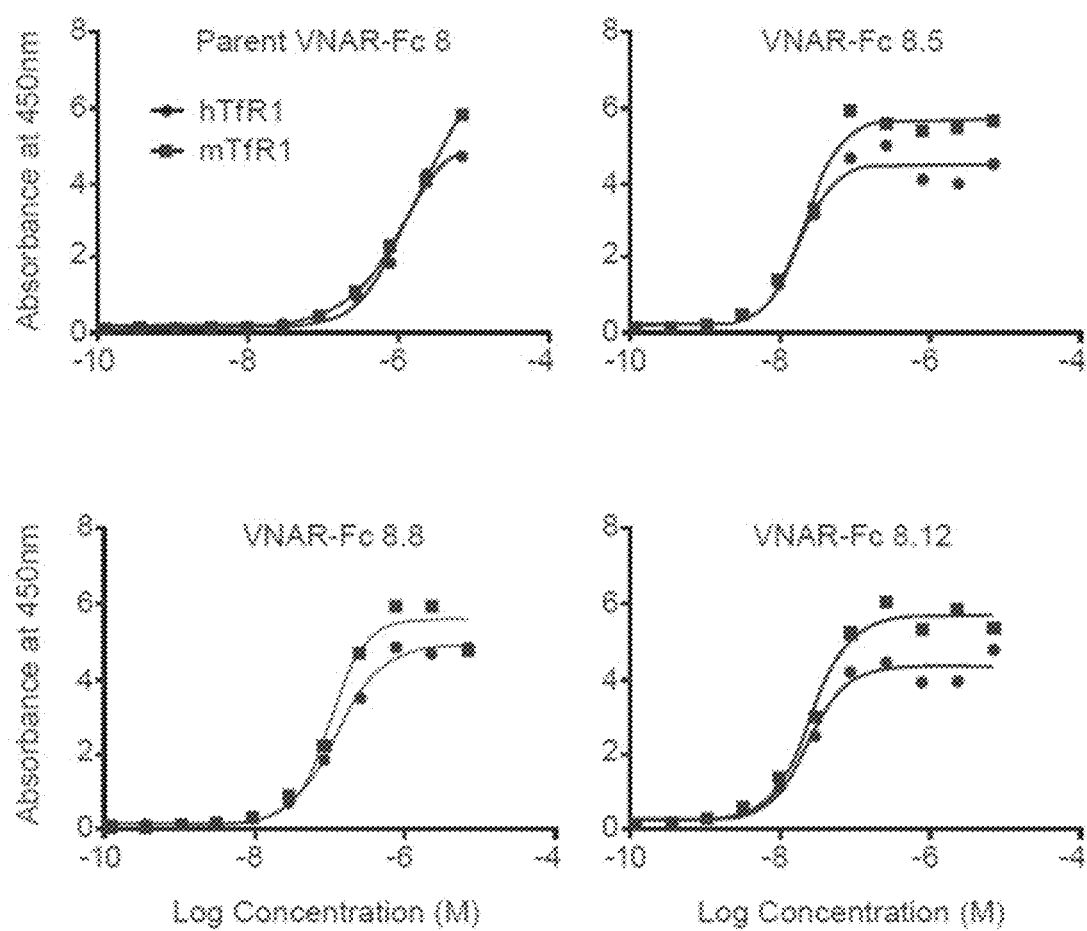
FIG. 10. Binding of Clone 8 variants to mouse and human TfR-1. The VNAR domains of Clone 8 and the indicated Clone 8 variants fused to the human Fc domain were analyzed for expression levels by human Fc-capture ELISA after small scale transfection into Expi293F cells.
Figure 10B:
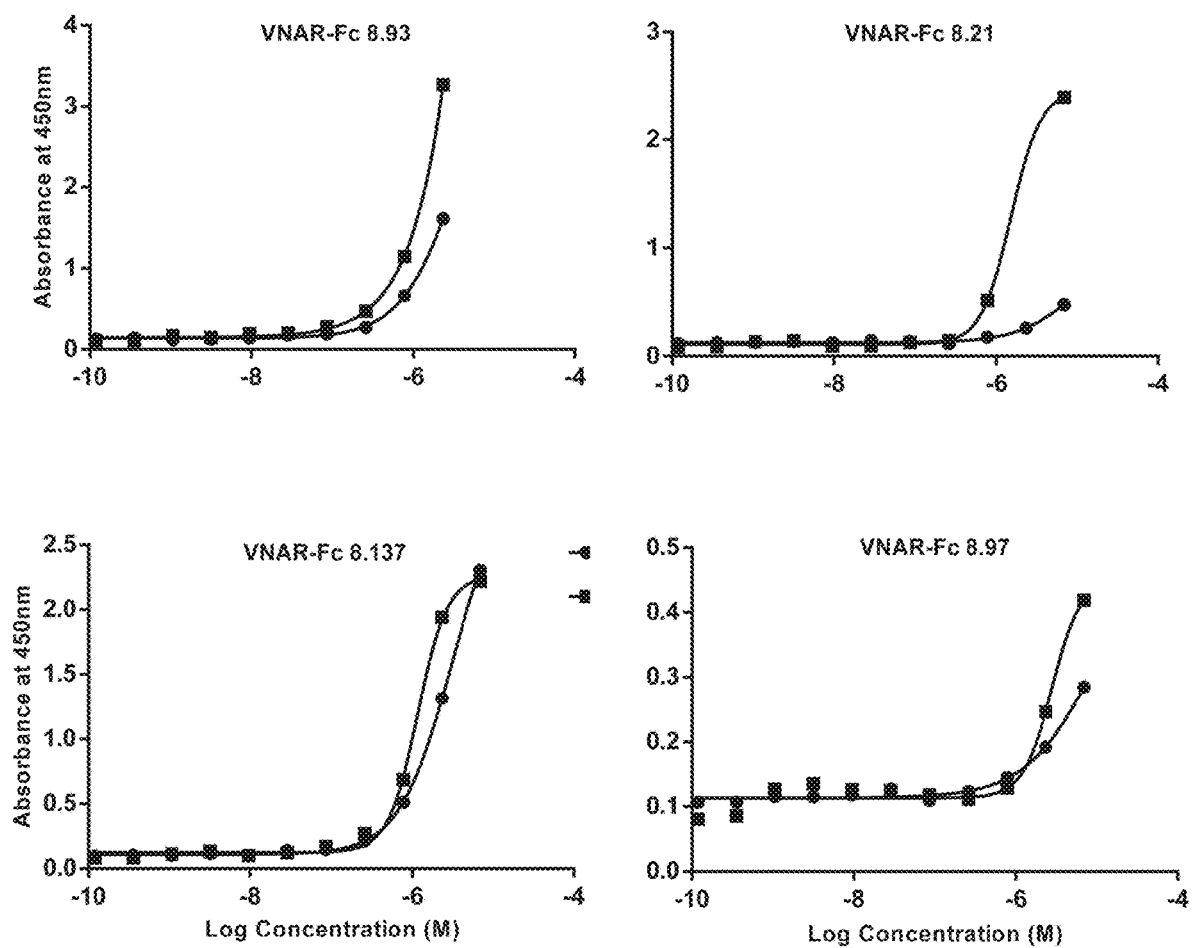
Figure 11:
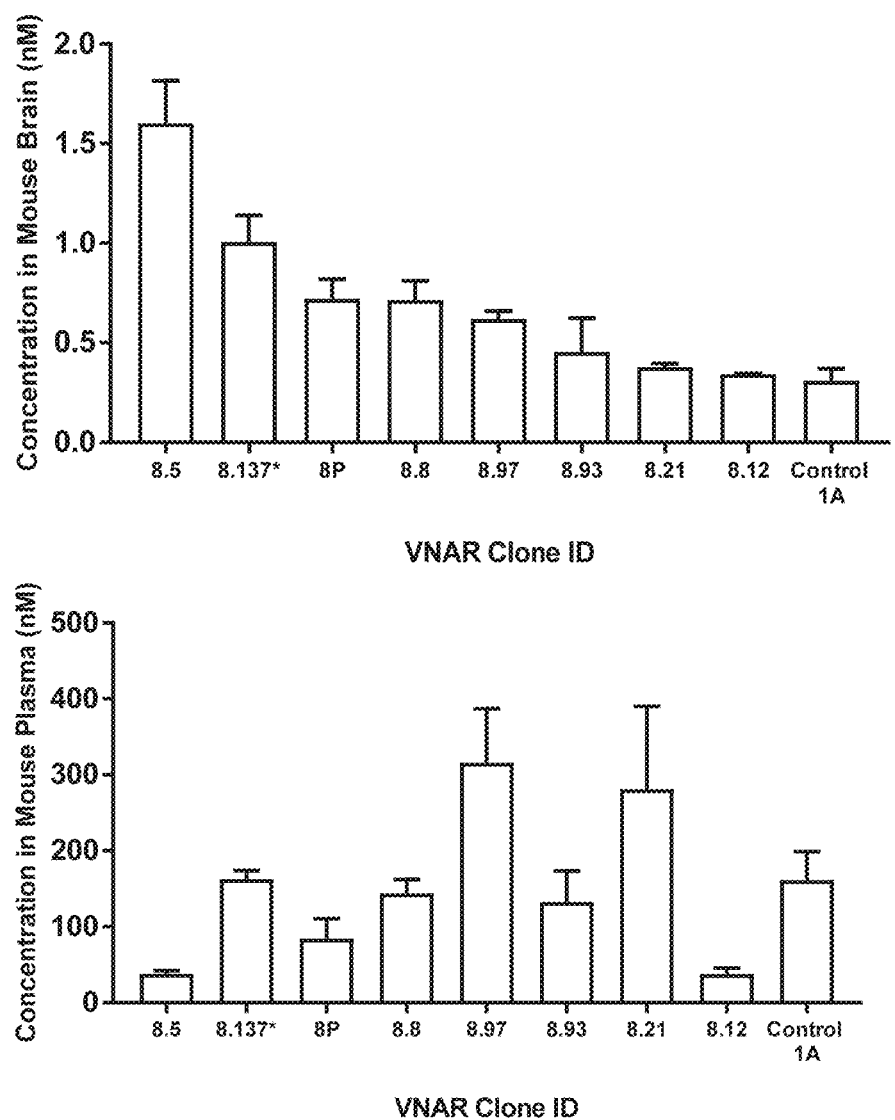
FIG. 11. Brain uptake of Clone 8 variants. Selected hFc fusions of the Clone 8 variants, prepared at small scale and indicated by Clone ID number, were tested for brain penetration in mice. The fusions were administered intravenously in mice tail veins at 25 nmol/kg and brains were excised 18 hours later following cardiac perfusion. The fusion concentration in brain homogenates (top panel) and plasma (bottom panel) was measured by human Fc-capture ELISA. 1A is a control VNAR-Fc fusion that does not penetrate brain efficiently.

Seven of the Clone 8 variants were formatted as VNAR-hFc fusions, expressed in expi293F cells at small scale (1 ml) and purified by Protein A chromatography (generally as described in Example 3). These variants were tested for their mouse and human TfR-1 binding activity (FIG. 10). Four clones (8.21, 8.93, 8.97, and 8.137) showed similar or weaker binding to TfR1 compared to the parental Clone 8, whereas Clones 8.5, 8.8, and 8.12 appeared to be more potent binders than parental Clone 8. The VNAR-hFc fusions were injected intravenously into mice at 25 nmol/kg, and brain and plasma levels were measured 18h post-injection as describe in Example 3. In this analysis, shown in FIG. 11, Clone 8.5 showed significantly higher brain uptake than the parental Clone 8 while the other variants tested showed comparable or lower levels of uptake.

Figure 12:
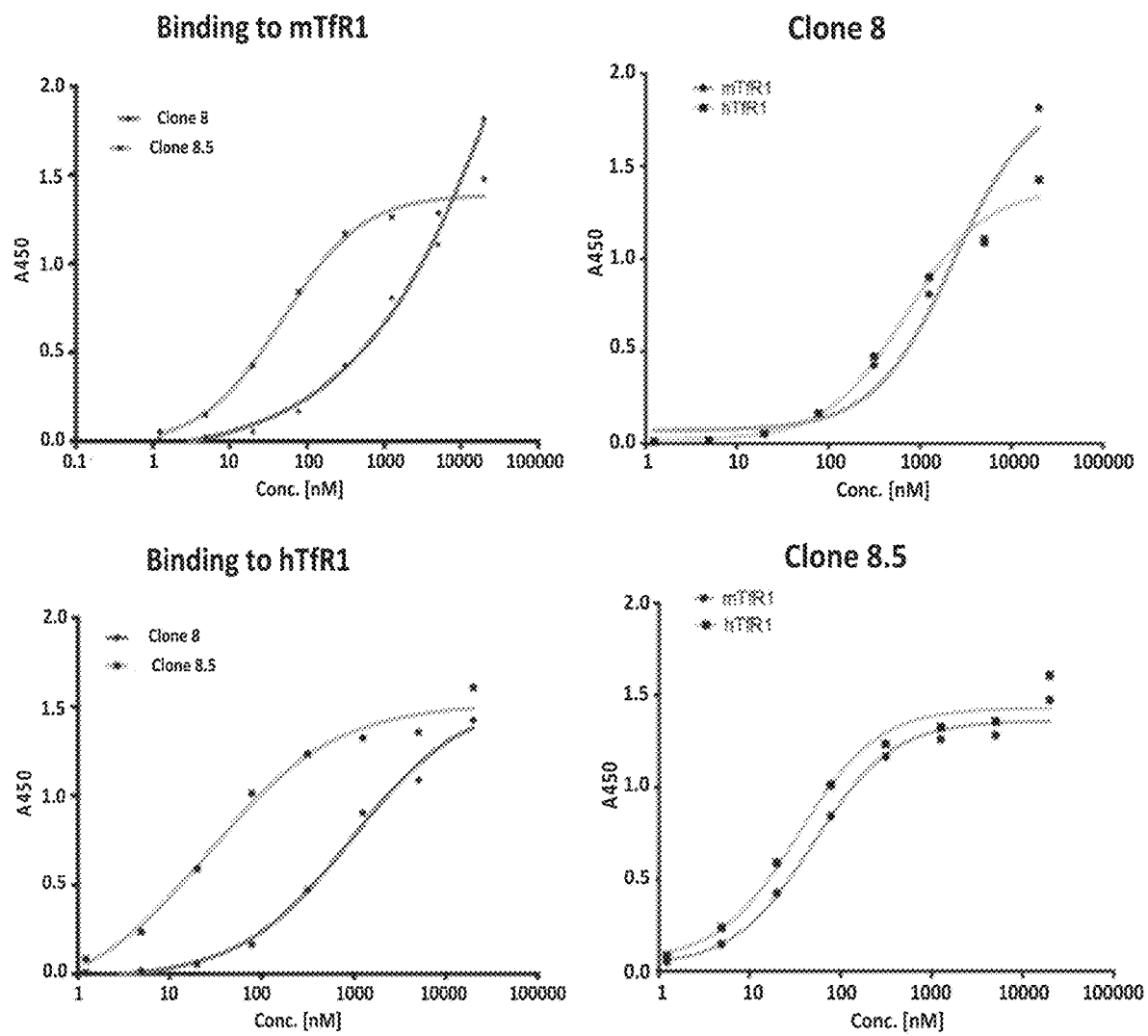
FIG. 12. Binding of Clone 8 and Clone 8.5 as VNAR-hFc fusions. The Fc fusions of Clones 8 and 8.5 expressed at large scale, purified and tested in an ELISA against increasing concentrations of mouse and human TfR-1. The results are presented in the left panels as a comparison of clone binding to each species (top, mouse TfR-1; bottom human TfR-1) and in the right panels as species binding for each clone (top, Clone 8; bottom, Clone 8.5).

To confirm the binding and functional activity of the Clone 8 variants, the VNAR-hFc fusion proteins were expressed at a larger scale and further purified. The binding potency of Clone 8.5 to both mouse and human TfR-1 was higher relative to parental Clone 8 (FIG. 12, left panels) and both clones bind similarly to both species of the receptor (FIG. 12, right panels). The EC50 for Clone 8.5 was more than 25-fold higher than parental Clone 8, with EC50x for the variant of 27 nM for human TfR-1 and 47 nM for mouse TfR-1 compared to approximately 930 µM for the parent against both species.

Figure 13:
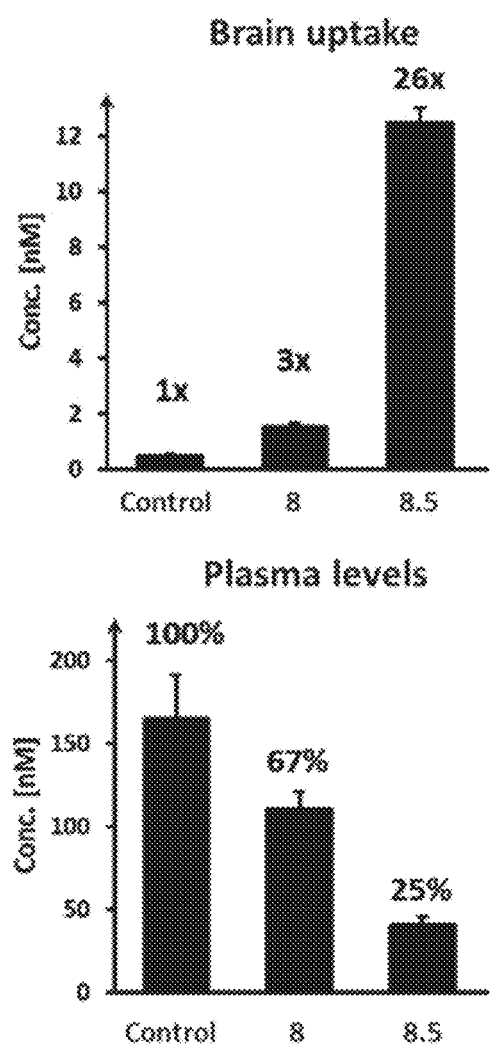
FIG. 13. Comparison of brain uptake of Clone 8 and Clone 8.5. The hFc fusions of these clones, expressed on a larger scale than used in FIG. 12, were tested for brain penetration in mice. The fusions were administered intravenously in mice tail veins at 25 nmol/kg and brains were excised 18 hours later following cardiac perfusion. The fusion concentration in brain homogenates (top panel) and plasma (bottom panel) was measured by human Fc capture ELISA. 1A is a control VNAR-Fc fusion that does not penetrate brain efficiently.
Figure 14:
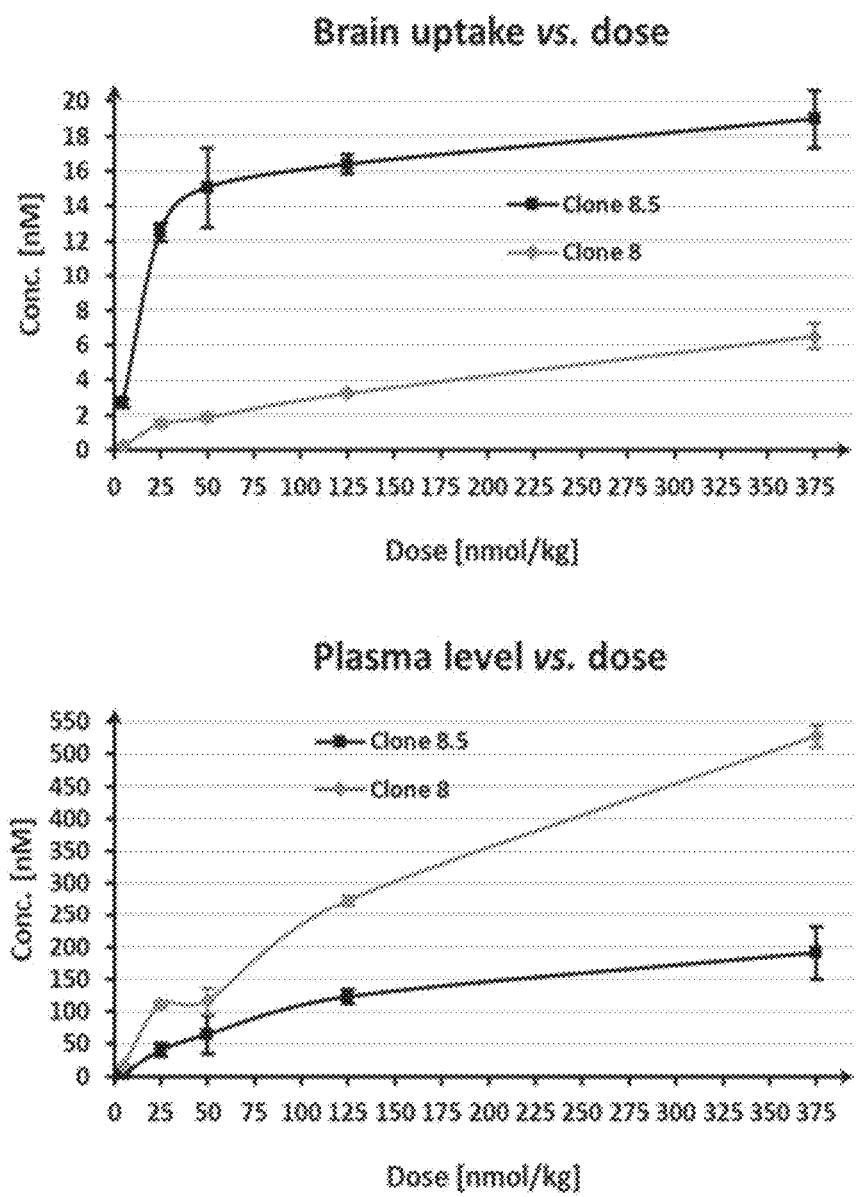
FIG. 14. Dose-dependent brain uptake of Clone 8 and Clone 8.5. The VNAR-Fc fusions of Clone 8, Clone 8.5 and 1A were administered intravenously in mice tail veins at various doses and analyzed as in FIG. 14 for brain uptake (top panel) and plasma levels (bottom panel).

FIG. 13 shows the brain and plasma levels of Clone 8.5 at 18h after intravenous injection of 25 nmol/kg (1.875 mg/kg). The parental clone was increased 3-fold relative to a control TfR1-binding VNAR with poor brain uptake and Clone 8. variant was elevated 26-fold relative to the control. The dose-response curves of brain and plasma level for Clone 8.5 and parental Clone 8 as VNAR-hFc fusion proteins are shown in FIG. 14. There was a very steep rise in brain concentration which reached 15 nM at approximately 50 nmol/kg (3.75 mg/kg). Brain concentration began to plateau at this dose indicative of receptor saturation.

Figure 15:
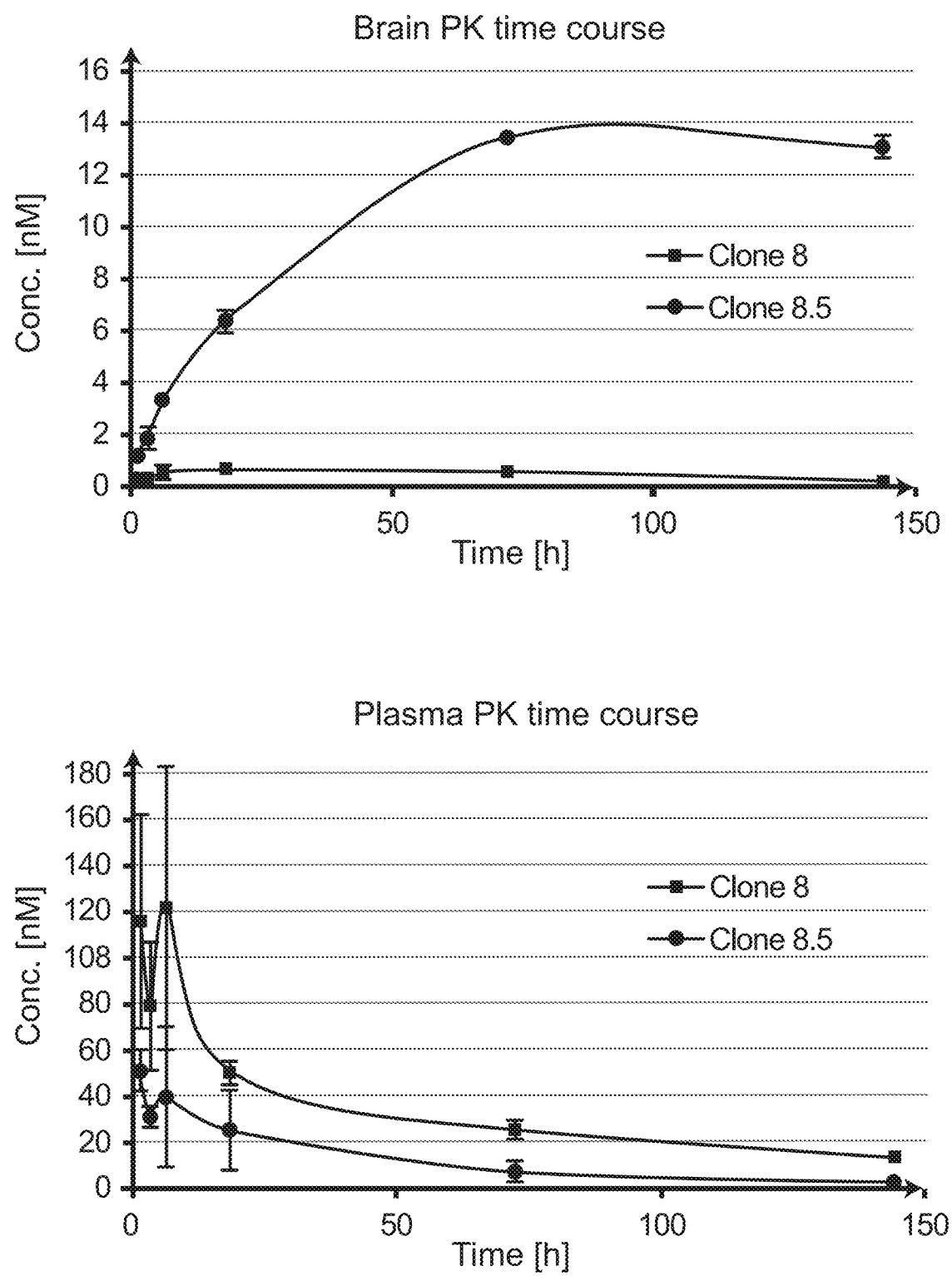
FIG. 15. Pharmacokinetic (PK) time course for Clone 8 and Clone 8.5. This graph depicts the pharmacokinetic time course of VNAR-hFc fusions of Clone 8.5 and Clone 8 in brain homogenates (top panel) and plasma (bottom panel) after a single intravenous injection of 12.5 nmol/kg of the fusions into mice tail veins.

The brain and plasma pharmacokinetics after a single intravenous injection of 12.5 nmol/kg (0.9375 mg/kg) is shown in FIG. 15 for Clone 8.5 relative to parental Clone 8 as VNAR-hFc fusion proteins. Clone 8.5 is markedly more potent than the Clone 8 and the brain concentrations continued to climb while plasma concentrations declined rapidly. The brain concentration of Clone 8.5 peaked at 14 nM between 75 and 100 hours after dosing, indicating a very long half-life in the brain (still near maximal after 6 days) despite a short half-life in plasma.

In summary, a VNAR against TfR-1 (Clone 8) was isolated from a semi-synthetic phage display library based on its ability to transcytosis through human brain capillary endothelial cells in vitro and its binding potency to the human and mouse receptor was improved by CDR3 mutagenesis. The clone 8.5 variant as an Fc fusion protein achieved receptor saturation in vivo at a dose <50 nmol/kg (3.75 mg/kg) and sustained brain concentration >10 nM for more than 6 days after a single intravenous dose of <12.5 nmol/kg (0.9375 mg/kg) in mice. The potency and duration of activity of Clone VNAR 8.5 exceeds that of any BBB shuttle to date.

TABLE 2

Amino Acid Sequences and Phage ELISA Results for Clone 8 Variants.

| SEQ. ID. | | | PHAGE ELISA $A_{450}$ | |
|---|---|---|---|---|
| NO. | Clone ID | CDR3 Sequence | mTfR1 | hTfR1 |
| 97 | 8.1 | LRLLSSILRGCNYRKHDV | 0.312 | 0.371 |
| 98 | 8.2 | LFNLSSILRGCNYRKHDV | 0.242 | 0.315 |
| 99 | 8.3 | VRFLSSILRGCNYRKHDV | 0.194 | 0.27 |
| 100 | 8.4 | KLWLSSILRGCNYRKHDV | 0.188 | 0.173 |
| 10 | Clone 8, Plate 2 | IAQLSSILRGCNYRKHDV | 0.181 | 0.296 |
| 11 | 8.5 | IAQLGWWLRGCNYRKHDV | 0.172 | 0.152 |
| 101 | 8.6 | IAQWWSILRGCNYRKHDV | 0.164 | 0.199 |
| 102 | 8.7 | IAQLSSILKACKYRKHDV | 0.123 | 0.087 |
| 12 | 8.8 | FAPLSSILRGCNYRKHDV | 0.118 | 0.103 |
| 103 | 8.9 | WNMLSSILRGCNYRKHDV | 0.108 | 0.119 |
| 104 | 8.10 | IAQLAIELRGCNYRKHDV | 0.101 | 0.072 |
| 105 | 8.11 | IAQLSSIYPGCNYRKHDV | 0.101 | 0.066 |
| 13 | 8.12 | RWRLSSILRGCNYRKHDV | 0.100 | 0.108 |
| 106 | 8.13 | IAQLALALRGCNYRKHDV | 0.096 | 0.075 |
| 107 | 8.14 | IAQLSSILGYCYYRKHDV | 0.095 | 0.067 |
| 108 | 8.15 | MWNLSSILRGCNYRKHDV | 0.095 | 0.095 |
| 10 | Clone 8, Plate 1 | IAQLSSILRGCNYRKHDV | 0.093 | 0.116 |
| 109 | 8.16 | IAKLFSILCGCNYRKHDV | 0.092 | 0.138 |
| 110 | 8.17 | IAYRKSIVRGCNYRKHDV | 0.091 | 0.091 |
| 111 | 8.18 | IAQLSSKYVGCNYRKHDV | 0.090 | 0.060 |
| 112 | 8.19 | QSQLSIVLRGCNYRKHDV | 0.088 | 0.078 |
| 113 | 8.20 | IAQLSSILRGCLDKKHDV | 0.087 | 0.084 |
| 114 | 8.21 | IAHLSSFRDGCNYRKHDV | 0.086 | 0.058 |
| 115 | 8.22 | IAQQKSILRGCNYHKHDV | 0.086 | 0.066 |
| 116 | 8.23 | IAQLPKQLRGCNYRKHDV | 0.085 | 0.055 |
| 117 | 8.24 | IAQLSSILRGCNYFFPDV | 0.084 | 0.093 |
| 118 | 8.25 | IAQLSSMELGCNYRKHDV | 0.084 | 0.06 |
| 119 | 8.26 | IASAFSILRGCNYRKHDV | 0.082 | 0.087 |
| 120 | 8.27 | QGMLSSILRGCNYRKHDV | 0.080 | 0.079 |
| 121 | 8.28 | AFILSSILRGCNYRKHDV | 0.077 | 0.085 |
| 122 | 8.29 | IAQLSSILLTCEYRKHDV | 0.077 | 0.059 |
| 123 | 8.30 | SMLLSSILRGCNYRKHDV | 0.077 | 0.114 |
| 124 | 8.31 | IAQLISILRGCNKNKHDV | 0.075 | 0.077 |
| 125 | 8.32 | IAQLSSIWKGCKYRKHDV | 0.074 | 0.065 |

TABLE 2-continued

Amino Acid Sequences and Phage ELISA Results for Clone 8 Variants.

| SEQ. ID. NO. | Clone ID | CDR3 Sequence | PHAGE ELISA $A_{450}$ | |
| --- | --- | --- | --- | --- |
| | | | mTfR1 | hTfR1 |
| 126 | 8.33 | RDALSSILRGCNYRKHDV | 0.073 | 0.090 |
| 127 | 8.34 | IAQLSSILRGCNYIAYDV | 0.072 | 0.078 |
| 128 | 8.35 | IAELFSILRGCNYRKHDV | 0.071 | 0.078 |
| 129 | 8.36 | IAQLSSILRGCNYWRWDV | 0.071 | 0.058 |
| 130 | 8.37 | IAQLSSQRWGCNYRKHDV | 0.071 | 0.069 |
| 131 | 8.38 | IAQLVLNLRGCNYRKHDV | 0.071 | 0.075 |
| 132 | 8.39 | IAQLSSILDDCEYRKHDV | 0.070 | 0.063 |
| 133 | 8.40 | IAQLYVGLRGCNYRKHDV | 0.070 | 0.066 |
| 134 | 8.41 | IAPQKSILRGCNYHKIDV | 0.068 | 0.072 |
| 135 | 8.42 | IAQLFIDLRGCNYRKHDV | 0.068 | 0.062 |
| 136 | 8.43 | IAQLSSILKPCWYRKHDV | 0.067 | 0.093 |
| 137 | 8.44 | IAQLSSILRGCNYLSMDV | 0.067 | 0.056 |
| 138 | 8.45 | IAQLSSILRGCNYNMEDV | 0.067 | 0.060 |
| 139 | 8.46 | IAQLSSYVVGCNYRKHDV | 0.067 | 0.056 |
| 140 | 8.47 | QTTLSSILRGCNYRKHDV | 0.067 | 0.072 |
| 141 | 8.48 | IAQLSSILRGCNYMMYDV | 0.066 | 0.082 |
| 142 | 8.49 | IAEMGSILRGCNYRKHDV | 0.065 | 0.060 |
| 143 | 8.50 | IANLSSILRGCNYRKHDV | 0.065 | 0.057 |
| 144 | 8.51 | IAQLSSDHPGCNYRKHDV | 0.065 | 0.058 |
| 145 | 8.52 | IAQLSSILRGCDRWKHDV | 0.065 | 0.049 |
| 146 | 8.53 | IAQLSSILRGCNYAWLDV | 0.065 | 0.051 |
| 147 | 8.54 | IASAVSILRGCNYRKHDV | 0.065 | 0.072 |
| 148 | 8.55 | IAQLSSILFWCAYRKHDV | 0.064 | 0.055 |
| 149 | 8.56 | IAQLSSILRGCTFDKHDV | 0.064 | 0.051 |
| 150 | 8.57 | IAQLGNLLRGCNYRKHDV | 0.063 | 0.083 |
| 151 | 8.58 | IAQLSSAGMGCNYRKHDV | 0.063 | 0.059 |
| 152 | 8.59 | IAQLSSHDHGCNYRKHDV | 0.063 | 0.073 |
| 153 | 8.60 | IAQLSSILLTCLYRKHDV | 0.063 | 0.073 |
| 154 | 8.61 | IAQLSSILQRCNYRKHDV | 0.063 | 0.067 |
| 155 | 8.62 | IAQLSSILRGCNYAAGDV | 0.063 | 0.056 |
| 156 | 8.63 | YRYLSSILRGCNYRKHDV | 0.063 | 0.071 |
| 157 | 8.64 | IAQLAFWLRGCNYRKHDV | 0.062 | 0.083 |
| 158 | 8.65 | IAQLSSIHDGCNYRKHDV | 0.062 | 0.081 |
| 159 | 8.66 | IAQLSSILRGCNYLAHDV | 0.062 | 0.052 |
| 160 | 8.67 | IAQLSSILRGCVEPKHDV | 0.062 | 0.051 |
| 161 | 8.68 | IAQLSSILSSCHYRKHDV | 0.062 | 0.056 |

TABLE 2-continued

Amino Acid Sequences and Phage ELISA Results for Clone 8 Variants.

| SEQ. ID. NO. | Clone ID | CDR3 Sequence | PHAGE ELISA $A_{450}$ | |
|---|---|---|---|---|
| | | | mTfR1 | hTfR1 |
| 162 | 8.69 | IAQLSSAPAGCNYRKHDV | 0.061 | 0.065 |
| 163 | 8.70 | IAQLSSILRGCNYQTSDV | 0.061 | 0.052 |
| 164 | 8.71 | IAQLSSILRGCTPHKHDV | 0.061 | 0.073 |
| 165 | 8.72 | IAQLSSILRGCSGVKHDV | 0.060 | 0.063 |
| 166 | 8.73 | IAQLSSILKGCNYRKHDV | 0.059 | 0.051 |
| 167 | 8.74 | IAQLSSLQDGCIYRKHDV | 0.059 | 0.061 |
| 168 | 8.75 | IAQLTEMLRGCNYRKHDV | 0.059 | 0.049 |
| 169 | 8.76 | QEELSSILRGCNYRKHDV | 0.059 | 0.050 |
| 170 | 8.77 | IAQLSSILRGCHLWKHDV | 0.058 | 0.055 |
| 171 | 8.78 | IAQLSSVVIGCNYSKHDV | 0.058 | 0.049 |
| 172 | 8.79 | MNQLDHFLRGCNYRKHDV | 0.058 | 0.061 |
| 173 | 8.80 | IAQLPHDLRGCNYRKHDV | 0.057 | 0.059 |
| 174 | 8.81 | IAQLSSAPDGCNYRKHDV | 0.057 | 0.065 |
| 175 | 8.82 | IAQLSSILRGCVYPKHDV | 0.057 | 0.048 |
| 176 | 8.83 | IAQLSSIRAGCNYRKHDV | 0.057 | 0.046 |
| 177 | 8.84 | IAWQSSILRGCNYRKHDV | 0.057 | 0.058 |
| 178 | 8.85 | IAQLRKKLRGCNYRKHDV | 0.056 | 0.059 |
| 179 | 8.86 | IAQLSSILVNCFYRKHDV | 0.056 | 0.053 |
| 180 | 8.87 | IAQFSSILCSCRYRKHDV | 0.055 | 0.070 |
| 181 | 8.88 | IAQLSSILFGCAYRKHDV | 0.055 | 0.050 |
| 182 | 8.89 | IAQLSSILFGCDYRKHDV | 0.055 | 0.048 |
| 183 | 8.90 | IAQLSSILRGCNYLYIDV | 0.055 | 0.054 |
| 184 | 8.91 | IAQLSSRKGGCNYRKHDV | 0.055 | 0.071 |
| 185 | 8.92 | IAQLTQWLRGCNYRKHDV | 0.055 | 0.051 |
| 186 | 8.93 | IAQQSSILRGCNYRKHDV | 0.055 | 0.050 |
| 187 | 8.94 | IADVGSILRGCNYRKHDV | 0.054 | 0.060 |
| 188 | 8.95 | IAQLSSILLKCEYRKHDV | 0.054 | 0.049 |
| 189 | 8.96 | IAQLSSMYKGCNYRKHDV | 0.054 | 0.051 |
| 190 | 8.97 | IAQLSSILRGCNYNIDDV | 0.053 | 0.057 |
| 191 | 8.98 | LEKLSSILRGCNYRKHDV | 0.053 | 0.055 |
| 192 | 8.99 | LFDLSSILRGCNYRKHDV | 0.053 | 0.059 |
| 193 | 8.100 | PHMLSSILRGCNYRKHDV | 0.053 | 0.048 |
| 194 | 8.101 | IAQLHTHLRGCNYRKHDV | 0.052 | 0.048 |
| 195 | 8.102 | IAQLSSILRGCAGVKHDV | 0.052 | 0.049 |
| 196 | 8.103 | IAQLSSILRGCKQFEYDV | 0.052 | 0.050 |
| 197 | 8.104 | IAQLSSRELGCNYRKHDV | 0.052 | 0.050 |

TABLE 2-continued

Amino Acid Sequences and Phage ELISA Results for Clone 8 Variants.

| SEQ. ID. NO. | Clone ID | CDR3 Sequence | PHAGE ELISA A$_{450}$ | |
|---|---|---|---|---|
| | | | mTfR1 | hTfR1 |
| 198 | 8.105 | VALQESILRGCNYRKHDV | 0.051 | 0.047 |
| 199 | 8.106 | VAQLSSHYDGCNYRKHDV | 0.051 | 0.054 |
| 200 | 8.107 | IAQLSSILFGCNYFKNDV | 0.051 | 0.048 |
| 201 | 8.108 | IAQLSSILRGCNYKNVDV | 0.051 | 0.044 |
| 202 | 8.109 | IAQLSSILRGCNYTLYDV | 0.051 | 0.055 |
| 203 | 8.110 | IAQLKWGLRGCNYRKHDV | 0.050 | 0.055 |
| 204 | 8.111 | IAQLSSILRGCNYDVNDV | 0.050 | 0.056 |
| 205 | 8.112 | IAQLSSVYKGCNYRKHDV | 0.050 | 0.050 |
| 206 | 8.113 | IAQLSSYRPGCNYRKHDV | 0.050 | 0.051 |
| 207 | 8.114 | IAQPSSILRGCNYGKLDV | 0.050 | 0.058 |
| 208 | 8.115 | IALHRSILRGCNYRKHDV | 0.049 | 0.047 |
| 209 | 8.116 | IAQLNHYLRGCNYRKHDV | 0.049 | 0.066 |
| 210 | 8.117 | IAQLSSILALCMYRKHDV | 0.049 | 0.056 |
| 211 | 8.118 | IAQLSSRAMGCNYRKHDV | 0.049 | 0.051 |
| 212 | 8.119 | IAQLSSVFIGCNYRKHDV | 0.049 | 0.045 |
| 206 | 8.120 | IAQLSSYRPGCNYRKHDV | 0.049 | 0.048 |
| 213 | 8.121 | IATLGSILRGCNYRKHDV | 0.049 | 0.049 |
| 214 | 8.122 | IAQLSSILRGCNYRASDV | 0.048 | 0.047 |
| 215 | 8.123 | IAQLSSIMRGCNYIMRDV | 0.048 | 0.048 |
| 216 | 8.124 | IAQLSSVKDGCNYRKHDV | 0.048 | 0.049 |
| 217 | 8.125 | IAQLSSYETGCNYRKHDV | 0.048 | 0.050 |
| 218 | 8.126 | IAQQDQDLRGCNYRKHDV | 0.048 | 0.050 |
| 219 | 8.127 | IAKPNSILRGCNYRKHDV | 0.047 | 0.047 |
| 220 | 8.128 | IAQLIKNLRGCNYRKHDV | 0.047 | 0.051 |
| 221 | 8.129 | IAQLSSILRGCNQPKHDV | 0.047 | 0.047 |
| 222 | 8.130 | IAQLSSILRGCNYAHLDV | 0.047 | 0.049 |
| 223 | 8.131 | IAQLSSILRGCNYLDLDV | 0.047 | 0.066 |
| 224 | 8.132 | IAQLSSILRGCNYMHPDV | 0.047 | 0.053 |
| 197 | 8.133 | IAQLSSRELGCNYRKHDV | 0.047 | 0.047 |
| 225 | 8.134 | DLTLSSILRGCNYRKHDV | 0.046 | 0.053 |
| 226 | 8.135 | IAQLFPPLRGCNYRKHDV | 0.046 | 0.058 |
| 227 | 8.136 | IAQLSSAGIGCNYRKHDV | 0.046 | 0.055 |
| 228 | 8.137 | IAQLSSILRGCNYFGKDV | 0.046 | 0.076 |
| 229 | 8.138 | IAQLSSLSFGCNYRKHDV | 0.046 | 0.047 |
| 230 | 8.139 | DAHLSSILRGCNYRKHDV | 0.045 | 0.050 |
| 231 | 8.140 | IAITLSILRGCNYRKHDV | 0.045 | 0.053 |

TABLE 2-continued

Amino Acid Sequences and Phage ELISA Results for Clone 8 Variants.

| SEQ. ID. NO. | Clone ID | CDR3 Sequence | PHAGE ELISA $A_{450}$ | |
| --- | --- | --- | --- | --- |
| | | | mTfR1 | hTfR1 |
| 232 | 8.141 | IAKASSILRGCNYRKHDV | 0.045 | 0.051 |
| 233 | 8.142 | IAQLHANLRGCNYRKHDV | 0.045 | 0.052 |
| 234 | 8.143 | IAQLHCMLRGCNYRKHDV | 0.045 | 0.051 |
| 235 | 8.144 | IAQLSSGHRGCNYRKHDV | 0.045 | 0.050 |
| 236 | 8.145 | IAQLSSILQPCYYRKHDV | 0.045 | 0.053 |
| 237 | 8.146 | IAQLSSILRGCEARKHDV | 0.045 | 0.045 |
| 238 | 8.147 | IAQLSSILRGCEGDKHDV | 0.045 | 0.052 |
| 239 | 8.148 | IAQLSSILRGCNYEHHDV | 0.045 | 0.049 |
| 240 | 8.149 | IAQLSSILRGCNYHPHDV | 0.045 | 0.052 |
| 241 | 8.150 | IAQLSSILRGCNYNQQDV | 0.045 | 0.058 |
| 242 | 8.151 | IAQLSSLERGCNYFQFDV | 0.045 | 0.048 |
| 243 | 8.152 | MDQLSNMLRGCNYRKHDV | 0.045 | 0.059 |
| 244 | 8.153 | IAQLAFGLRGCNYRKHDV | 0.044 | 0.048 |
| 245 | 8.154 | IAQLSSILRGCGGSKHDV | 0.044 | 0.055 |
| 246 | 8.155 | IAQLSSILRGCNYKIADV | 0.044 | 0.053 |
| 247 | 8.156 | IAQLSSQSVGCNYRKHDV | 0.044 | 0.062 |
| 110 | 8.157 | IAYRKSIVRGCNYRKHDV | 0.044 | 0.048 |
| 248 | 8.158 | IAQLNVILRGCNYRKHDV | 0.043 | 0.046 |
| 249 | 8.159 | IAQLSSDGQGCNYRKHDV | 0.043 | 0.057 |
| 250 | 8.160 | IAQLSSILRGCFPQKHDV | 0.043 | 0.049 |
| 251 | 8.161 | IAQLSSILRGCIAGKHDV | 0.043 | 0.048 |
| 252 | 8.162 | IAQLSSNRGCNYRKHDV | 0.042 | 0.055 |

REFERENCES

Abbott et al. (2010) Neurobiol. Dis. 37(1):13-25).

Boado et al (2009) "Engineering and Expression of a Chimeric Transferrin Receptor Monoclonal Antibody for Blood-Brain Barrier Delivery in the Mouse," Biotechnol. Bioeng. 102:1251-8.

Chen et al (2011) J. Immunol. 186:3215-3225.

Daniels et al. (2006) "The transferrin receptor part I: Biology and targeting with cytotoxic antibodies for the treatment of cancer." Clin. Immunol. 121:144-58.

Demogines et al. (2013). "Dual host virus arms races shape an essential housekeeping protein." PLoS Biol. 11(5):e1001571.

Forejtnikovà et al. (2010) "Transferrin receptor 2 is a component of the erythropoietin receptor complex and is required for efficient erythropoiesis," Blood 116: 5357-67.

Friden et al. (1991) "Anti-transferrin receptor antibody and antibody-drug conjugates cross the blood-brain barrier," Proc. Natl. Acad. Sci. USA 88:4771-5.

Gerhardt et al. (1991) "The cDNA sequence and primary structure of the chicken transferrin receptor." Gene 102:249-54.

Greenberg et al. (1995). "A new antigen receptor gene family that undergoes rearrangement and extensive somatic diversification in sharks." Nature 374:168-173.

Hollmann et al. (2017) "Accelerated differentiation of human induced pluripotent stem cells to blood-brain barrier endothelial cells." Fluids Barriers CNS (2017) 14:9, 13 pages.

Jefferies et al. (1985) "Analysis of lymphopoietic stem cells with a monoclonal antibody to the rat transferrin receptor," Immunology 54:333-341.

Jones et al. (2007) "Blood-Brain Barrier Transport of Therapeutics via Receptor-Mediation," Pharm. Res. 24:1759-71.

Könning et al. (2017) "Camelid and shark single antibodies: structural features and therapeutic potential." Curr. Opin. Struct. Biol. 45:10-16.

Krah et al. (2016). "Single-domain antibodies for biomedical applications. Immunopharmacol. Immunotoxicol. 38:21-28.

Liu et al. (2014). "Thermal stability and refolding capability of shark derived single domain antibodies." Mol. Immunol. 59(2):194-199.
Munoz-Martinez et al (2010) Biochemical Pharmacology 80:793-800.
Nałęcz et al. (2017) Neurochem Res. 42(3):795-809.
Niewoehner et al. (2014) "Increased Brain Penetration and Potency of a Therapeutic Antibody Using a Monovalent Molecular Shuttle," Neuron 81:49-60.
Pardridge (2012) "Drug transport across the blood-brain barrier," J. Cereb. Blood Flow Metab. 32:1959-72.
Rahman et al. (2016) "Immortalized endothelial cell lines for in vitro blood-brain barrier models: As systematic review." Brain Res. 1642:532-545.
Silvestri et al. (2014) "The extrahepatic role of TFR2 in iron homeostasis," Front. Pharmacol. 5:93, 6 pages.
Srinivasan et al. (2015) "TEER measurement techniques for in vitro barrier model systems" J. Lab. Autom. 20: 107-126.
Stanfield et al. (2004). "Crystal structure of a shark single-domain antibody V region in complex with lysozyme." Science 305:1770-1773.
Streltsov et al. (2005). "Structure of a shark IgNAR antibody variable domain and modeling of an early developmental isotype." Protein Sci. 14:2901-2909.
Tuma et al. (2003) "Transcytosis: Crossing Cellular Barriers," Physiol. Rev. 83:871-932.
White et al. (1990) "Combinations of anti-transferrin receptor monoclonal antibodies inhibit human tumor cell growth in vitro and in vivo: evidence for synergistic antiproliferative effects." Cancer Res. 50:6295-301.
White et al. (1992). "Monoclonal antibodies against defined epitopes of the human transferrin receptor cytoplasmic tail." Biochim. Biophys. Acta. 11136(1): 28-34.
Yu et al. (2014) "Therapeutic bispecific antibodies cross the blood-brain barrier in nonhuman primates," Sci. Transl. Med. 3:84ra44, 10 pages.

We claim:

1. An isolated TfR-specific binding moiety comprising a VNAR domain capable of specifically binding to human TfR-1 without interfering with transferrin binding to and/or transport by human TfR-1, wherein said VNAR domain has the amino acid sequence of any one of SEQ ID NOS. 18, 7, 22 or 34.

2. The binding moiety of claim 1, wherein said moiety is capable of uptake across the blood brain barrier.

3. A conjugate comprising the binding moiety of claim 1 operably linked to a heterologous molecule which differs in biological activity from said moiety.

4. A nucleic acid molecule or a vector encoding at least one binding moiety of claim 1 or a conjugate thereof, wherein said conjugate is a fusion protein with a heterologous diagnostic or therapeutic agent operably linked to said moiety, which further comprises expression control sequences to enable expression of the nucleic acid molecule in a host cell to thereby produce said at least one binding moiety or conjugate.

5. A pharmaceutical composition comprising a TfR-specific binding moiety of claim 1 or a conjugate thereof.

6. A method of medical treatment which comprises administering a therapeutically-effective amount of the pharmaceutical composition of claim 5 to deliver a diagnostic or therapeutic agent to the brain of a mammalian subject in need thereof.

7. A kit for detecting or quantifying TfR in a sample which comprises at least one TfR-specific binding moiety of claim 1 or a conjugate thereof.

8. A method of delivering a diagnostic or therapeutic agent across a cell membrane in a subject, which comprises administering a diagnostic or therapeutic agent operably linked to a TfR-specific binding moiety of claim 1, wherein said binding moiety is endocytosed to thereby deliver said diagnostic or therapeutic agent across the cell membrane, wherein said cell membrane is part of the blood brain barrier or the GI tract.

9. A method of delivering a therapeutic or diagnostic molecule across the blood brain barrier or to the gastrointestinal (GI) tract which comprises administering a TfR-specific binding moiety of claim 1 to a subject for a time and in an amount effective to treat or diagnose a CNS disease or condition or a GI disease or condition, said therapeutic or diagnostic molecule being operably conjugated to said moiety.

10. An isolated TfR-specific binding moiety comprising a VNAR domain represented by the formula, from N to C terminus,

FW1-CDR1-FW2-HV2-FW2'-HV4-FW3-CDR3-FW4, wherein
(a) FW1 is ARVDQTPQTITKETGESLTINCVLR (SEQ ID NO. 1) or PRVDQTPQTITKETGESLTINCVLR (SEQ ID NO. 2),
(b) CDR1 is DSNCALP (SEQ ID NO. 3),
(c) FW2-HV2-FW2'-HV4-FW3 is STYWYRKKSGSTNEESISKGGRYVETVNSGSKSFSLRINDLTVEDSGTYRCKV (SEQ ID NO. 4),
(d) CDR3 is IAQLSSILRGCNYRKHDV (SEQ ID NO. 10), IAQLGWWLRGCNYRKHDV (SEQ ID NO. 11), FAPLSSILRGCNYRKHDV (SEQ ID NO. 12) or RWRLSSILRGCNYRKHDV (SEQ ID NO. 13); and
(e) FW4 is YGDGTAVTVNA (SEQ ID NO. 6), wherein the moiety is specific for human TfR-1 and capable of crossing the blood brain barrier.

11. The binding moiety of claim 10, wherein FW1 is ARVDQTPQTITKETGESLTINCVLR (SEQ ID NO. 1) and CDR3 is IAQLSSILRGCNYRKHDV (SEQ ID NO. 10).

12. The binding moiety of claim 10, wherein FW1 is ARVDQTPQTITKETGESLTINCVLR (SEQ ID NO. 1) and CDR3 is IAQLGWWLRGCNYRKHDV (SEQ ID NO. 11).

13. The binding moiety of claim 10, wherein FW1 is ARVDQTPQTITKETGESLTINCVLR (SEQ ID NO. 1) and CDR3 is FAPLSSILRGCNYRKHDV (SEQ ID NO. 12).

14. The binding moiety of claim 10, wherein FW1 is ARVDQTPQTITKETGESLTINCVLR (SEQ ID NO. 1) and CDR3 is RWRLSSILRGCNYRKHDV (SEQ ID NO. 13).

15. The binding moiety of claim 1, wherein said moiety comprises the VNAR domain having the amino acid sequence of SEQ ID NO. 7.

16. A conjugate comprising the binding moiety of claim 10 operably linked to a heterologous molecule which differs in biological activity from said moiety.

17. A nucleic acid molecule or a vector encoding at least one binding moiety of claim 10 or a conjugate thereof, wherein said conjugate is a fusion protein with a heterologous diagnostic or therapeutic agent operably linked to said moiety, which further comprises expression control sequences to enable expression of the nucleic acid molecule in a host cell to thereby produce said at least one binding moiety or conjugate.

18. A pharmaceutical composition comprising a TfR-specific binding moiety of claim 10 or a conjugate thereof.

19. A method of medical treatment which comprises administering a therapeutically-effective amount of the pharmaceutical composition of claim 18 to deliver a diagnostic or therapeutic agent to the brain of a mammalian subject in need thereof.

20. A kit for detecting or quantifying TfR in a sample which comprises at least one TfR-specific binding moiety of claim 10 or a conjugate thereof.

21. A method of delivering a diagnostic or therapeutic agent across a cell membrane in a subject, which comprises administering a diagnostic or therapeutic agent operably linked to a TfR-specific binding moiety of claim 10, wherein said binding moiety is endocytosed to thereby deliver said diagnostic or therapeutic agent across the cell membrane, wherein said cell membrane is part of the blood brain barrier or the GI tract.

22. A method of delivering a therapeutic or diagnostic molecule across the blood brain barrier or to the gastrointestinal (GI) tract which comprises administering a TrF-specific binding moiety of claim 10 to a subject for a time and in an amount effective to treat or diagnose a CNS disease or condition or a GI disease or condition, said therapeutic or diagnostic molecule being operably conjugated to said moiety.

* * * * *

SEQUENCE LISTING

```
<160> NUMBER OF SEQ ID NOS: 252

<210> SEQ ID NO 1
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Ala Arg Val Asp Gln Thr Pro Gln Thr Ile Thr Lys Glu Thr Gly Glu
1               5                   10                  15

Ser Leu Thr Ile Asn Cys Val Leu Arg
            20                  25

<210> SEQ ID NO 2
<211> LENGTH: 25
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Pro Arg Val Asp Gln Thr Pro Gln Thr Ile Thr Lys Glu Thr Gly Glu
1               5                   10                  15

Ser Leu Thr Ile Asn Cys Val Leu Arg
            20                  25

<210> SEQ ID NO 3
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Asp Ser Asn Cys Ala Leu Pro
1               5
```

<210> SEQ ID NO 4
<211> LENGTH: 53
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 4

Ser Thr Tyr Trp Tyr Arg Lys Lys Ser Gly Ser Thr Asn Glu Glu Ser
1               5                   10                  15

Ile Ser Lys Gly Gly Arg Tyr Val Glu Thr Val Asn Ser Gly Ser Lys
            20                  25                  30

Ser Phe Ser Leu Arg Ile Asn Asp Leu Thr Val Glu Asp Ser Gly Thr
        35                  40                  45

Tyr Arg Cys Lys Val
    50

<210> SEQ ID NO 5
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence: Synthetic peptide"
<220> FEATURE:
<221> NAME/KEY: VARIANT
<222> LOCATION: (1)..(1)
<223> OTHER INFORMATION: /replace="Ile" or "Arg"
<220> FEATURE:
<221> NAME/KEY: VARIANT
<222> LOCATION: (2)..(2)
<223> OTHER INFORMATION: /replace="Trp"
<220> FEATURE:
<221> NAME/KEY: VARIANT
<222> LOCATION: (3)..(3)
<223> OTHER INFORMATION: /replace="Gln" or "Arg"
<220> FEATURE:
<221> NAME/KEY: VARIANT
<222> LOCATION: (5)..(5)
<223> OTHER INFORMATION: /replace="Ser"
<220> FEATURE:
<221> NAME/KEY: VARIANT
<222> LOCATION: (6)..(6)
<223> OTHER INFORMATION: /replace="Trp"
<220> FEATURE:
<221> NAME/KEY: VARIANT
<222> LOCATION: (7)..(7)
<223> OTHER INFORMATION: /replace="Trp"
<220> FEATURE:
<221> NAME/KEY: SITE
<222> LOCATION: (1)..(18)
<223> OTHER INFORMATION: /note="Variant residues given in the sequence have no preference with respect to those in the annotations for variant positions"

<400> SEQUENCE: 5

Phe Ala Pro Leu Gly Ser Ile Leu Arg Gly Cys Asn Tyr Arg Lys His
1               5                   10                  15

Asp Val

<210> SEQ ID NO 6
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic peptide"

<400> SEQUENCE: 6

Tyr Gly Asp Gly Thr Ala Val Thr Val Asn Ala
1               5                   10

<210> SEQ ID NO 7
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 7

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Ile Ala Gln Leu Ser Ser Ile Leu Arg Gly Cys
                85                  90                  95

Asn Tyr Arg Lys His Asp Val Tyr Gly Asp Gly Thr Ala Val Thr Val
                100                 105                 110

Asn Ala

<210> SEQ ID NO 8
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"
<220> FEATURE:
<221> NAME/KEY: SITE
<222> LOCATION: (86)..(103)
<223> OTHER INFORMATION: /note="This region may encompass
    'IAQLSSILRGCNYRKHDV', 'IAQLGWWLRGCNYRKHDV', 'FAPLSSILRGCNYRKHDV',
    or 'RWRLSSILRGCNYRKHDV'"

<400> SEQUENCE: 8

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Xaa Xaa Xaa Xaa Xaa Xaa Xaa Xaa Xaa Xaa
                85                  90                  95

Xaa Xaa Xaa Xaa Xaa Xaa Tyr Gly Asp Gly Thr Ala Val Thr Val
            100                 105                 110

Asn Ala

<210> SEQ ID NO 9
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (86)..(103)
<223> OTHER INFORMATION: /note="This region may encompass
      'IAQLSSILRGCNYRKHDV', 'IAQLGWWLRGCNYRKHDV', 'FAPLSSILRGCNYRKHDV',
      or 'RWRLSSILRGCNYRKHDV'"

<400> SEQUENCE: 9

Pro Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Lys Val Xaa Xaa Xaa Xaa Xaa Xaa Xaa Xaa Xaa Xaa
                85                  90                  95

Xaa Xaa Xaa Xaa Xaa Xaa Xaa Tyr Gly Asp Gly Thr Ala Val Thr Val
            100                 105                 110

Asn Ala

<210> SEQ ID NO 10
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

Ile Ala Gln Leu Ser Ser Ile Leu Arg Gly Cys Asn Tyr Arg Lys His
1               5                   10                  15

Asp Val

<210> SEQ ID NO 11
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

Ile Ala Gln Leu Gly Trp Trp Leu Arg Gly Cys Asn Tyr Arg Lys His
1               5                   10                  15

Asp Val

```
<210> SEQ ID NO 12
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Phe Ala Pro Leu Ser Ser Ile Leu Arg Gly Cys Asn Tyr Arg Lys His
1               5                   10                  15

Asp Val

<210> SEQ ID NO 13
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Arg Trp Arg Leu Ser Ser Ile Leu Arg Gly Cys Asn Tyr Arg Lys His
1               5                   10                  15

Asp Val

<210> SEQ ID NO 14
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 14

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Ser
                20                  25                  30

Thr Thr Tyr Trp Tyr Arg Lys Lys Ser Gly Ser Thr Asn Glu Glu Ser
            35                  40                  45

Ile Ser Leu Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Ser Asp Val Val Ser Cys Asp Asp Gly Trp Asn
                85                  90                  95

Trp Leu Asp Val Tyr Gly Gly Gly Thr Ala Val Thr Val Asn Ala
                100                 105                 110

<210> SEQ ID NO 15
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

<400> SEQUENCE: 15

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Glu Leu Ser
            20                  25                  30

Ser Thr Tyr Trp Tyr Arg Lys Lys Ser Asp Ser Thr Asn Glu Ala Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Phe Thr Ser Asp Ser Tyr Asp Leu Gly Asp Val
                85                  90                  95

Tyr Gly Gly Gly Thr Val Val Thr Val Asn Ala
            100                 105

<210> SEQ ID NO 16
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 16

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Lys Asp Ser Gly Thr
65                  70                  75                  80

Tyr Arg Cys Asn Val Val Gln Glu Pro Tyr Ser Cys Lys Gly Arg Asp
                85                  90                  95

Asp Val Tyr Gly Gly Gly Thr Ala Val Thr Val Asn Ala
            100                 105

<210> SEQ ID NO 17
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
    Synthetic polypeptide"

<400> SEQUENCE: 17

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

```
Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Lys Asp Ser Gly Thr
65                  70                  75                  80

Tyr Arg Cys Lys Val Met Ser Gln Glu Val Arg Trp Gln Met Thr Cys
                85                  90                  95

Lys Ile Val Val Met Asp Val Tyr Gly Gly Gly Thr Val Thr Val
                100                 105                 110

Asn Ala
```

```
<210> SEQ ID NO 18
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 18

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Leu Trp Tyr Arg Thr Lys Ser Gly Ser Arg Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Lys Asp Ser Gly Thr
65                  70                  75                  80

Tyr Arg Cys Asn Val Gln Gln Tyr Asp Cys Ile Ala Ser Phe Asp Val
                85                  90                  95

Tyr Gly Asp Gly Thr Ala Val Thr Val Asn Ala
                100                 105
```

```
<210> SEQ ID NO 19
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 19

Ala Arg Val Asp Gln Thr Pro Gln Thr Val Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Leu Trp Tyr Arg Thr Lys Ser Gly Ser Arg Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Cys Ser Asn Tyr Cys Pro Ile Lys Asp Asp Val
                85                  90                  95
```

-continued

```
Tyr Gly Asp Gly Thr Ala Val Thr Val Asn Ala
            100                 105

<210> SEQ ID NO 20
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 20

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Leu Ser
            20                  25                  30

Ser Thr Leu Trp Tyr Arg Thr Lys Ser Gly Ser Arg Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gln Ser Trp Pro Pro Gly Asn Gly Trp Trp Cys
                85                  90                  95

Asp Val Tyr Gly Asp Gly Thr Ala Val Thr Val Asn Ala
            100                 105

<210> SEQ ID NO 21
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 21

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Trp Tyr Arg Lys Lys Ser Asp Ser Thr Asn Glu Glu Ser Ile
        35                  40                  45

Ser Lys Gly Gly Arg Tyr Val Glu Thr Val Asn Ser Gly Ser Lys Ser
    50                  55                  60

Phe Ser Leu Arg Ile Asn Asp Leu Thr Val Lys Asp Ser Gly Thr Tyr
65                  70                  75                  80

Arg Cys Lys Val Leu Tyr Pro Asn Cys Tyr Arg Cys Met Trp Gly Gln
                85                  90                  95

Val Thr Asp Val Tyr Gly Gly Gly Thr Ala Val Thr Val Asn Ala
            100                 105                 110

<210> SEQ ID NO 22
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
```

```
<400> SEQUENCE: 22

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Val Gln Tyr Pro Thr Ala Lys Cys Arg Gln Val
                85                  90                  95

Asp Val Tyr Gly Gly Gly Thr Ala Val Thr Val Asn Ala
            100                 105

<210> SEQ ID NO 23
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 23

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gln Trp Leu Trp Ser Phe Ser Cys Leu Pro Cys
                85                  90                  95

Val Glu Asp Val Tyr Gly Gly Gly Thr Val Val Thr Val Asn Ala
            100                 105                 110

<210> SEQ ID NO 24
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 24

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Glu Leu Gly
            20                  25                  30

Ser Thr Cys Trp Tyr Arg Lys Lys Ser Gly Ser Thr Asn Glu Glu Ser
        35                  40                  45
```

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Gly Gly Thr
65                  70                  75                  80

Tyr Arg Cys Gly Ala Trp Ser Arg Leu Ser Ser Trp Gly Cys Asp
             85                  90                  95

Val Gly Leu Gln Cys Met Gly Cys Trp Asp Leu Trp Ala Ala Cys Gly
             100                 105                 110

Asp Gly Thr Ala Val Thr Val Asn Ala
         115                 120

<210> SEQ ID NO 25
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Ala Arg Val Asp Gln Thr Pro Gln Thr Ile Thr Lys Gln Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
             35                  40                  45

Ile Ser Leu Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
65                  70                  75                  80

Tyr Arg Cys Asn Val Arg Arg Leu Gln Ala Trp Gly Ser Cys Arg Gly
             85                  90                  95

Gly Asp Val Tyr Gly Gly Thr Val Val Thr Val Asn Ala
             100                 105                 110

<210> SEQ ID NO 26
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
                20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Lys Asp Ser Gly Thr
65                  70                  75                  80

Tyr Arg Cys Asn Val Met Val Phe Gln Val Ser Gly Asp Tyr Ser Arg
             85                  90                  95

```
Leu Glu Asp Val Tyr Gly Gly Gly Thr Val Val Thr Val Asn Ala
            100                 105                 110
```

```
<210> SEQ ID NO 27
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Glu Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Ala Pro Arg Trp Gln Met Gly Gly Gln Trp Cys Asp
                85                  90                  95

Gly Gly Thr Ala Ala Cys Arg Ser Gly Met Ala Glu Val Ala Ala Cys
            100                 105                 110

Gly Asp Gly Thr Ala Val Thr Val Asn Ala
            115                 120
```

```
<210> SEQ ID NO 28
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Gln Ser Ala Gln Gly Met Gly Leu Asn Gly Cys
                85                  90                  95

Lys Pro Gly Arg Val Asp Val Tyr Gly Asp Gly Thr Ala Val Thr Val
            100                 105                 110

Asn Ala
```

```
<210> SEQ ID NO 29
<211> LENGTH: 111
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic polypeptide"

<400> SEQUENCE: 29

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Ile Thr Val Glu Asp Ser Gly Arg
65                  70                  75                  80

Tyr Arg Cys Asn Val Tyr Asn Phe Phe Thr Tyr Gln Cys Arg Trp Phe
                85                  90                  95

Gln Ser Asp Val Tyr Gly Asp Gly Thr Ala Val Thr Val Asn Ala
            100                 105                 110

<210> SEQ ID NO 30
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 30

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Asp Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Cys Thr Gly Met Ser Cys Pro Cys Leu Gly Arg
                85                  90                  95

Arg Gln Thr Asp Val Tyr Gly Gly Gly Thr Ala Val Thr Val Asn Ala
            100                 105                 110

<210> SEQ ID NO 31
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30
```

```
Ser Thr Tyr Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Gly Gln Ala Gln Arg Leu Arg Ser Asn Val Asp
             85                  90                  95

Asp Val Tyr Gly Gly Gly Thr Val Thr Val Asn Ala
            100                 105

<210> SEQ ID NO 32
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Ala Arg Val Asp Gln Thr Pro Arg Ser Val Thr Lys Glu Thr Gly Glu
 1               5                  10                  15

Ser Leu Thr Ile Asn Cys Val Leu Arg Asp Ser Asn Cys Ala Leu Pro
             20                  25                  30

Ser Thr Tyr Trp Tyr Arg Lys Lys Ser Gly Ser Thr Asn Glu Glu Ser
         35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Lys Asp Ser Gly Thr
 65                  70                  75                  80

Tyr Arg Cys Asn Val Lys Trp Asp Cys Arg Tyr Gln Cys Ile Cys Val
             85                  90                  95

Ser Ala Asp Val Tyr Gly Asp Gly Thr Ala Val Thr Val Asn Ala
            100                 105                 110

<210> SEQ ID NO 33
<211> LENGTH: 106
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Ala Arg Val Asp Gln Thr Pro Arg Val Thr Lys Glu Thr Gly Glu Ser
 1               5                  10                  15

Leu Thr Ile Asn Cys Val Leu Arg Asp Asn Asn Cys Ala Leu Ser Thr
             20                  25                  30

Thr Tyr Trp Tyr Arg Lys Lys Ser Gly Ser Thr Asn Glu Glu Asn Ile
         35                  40                  45

Ser Lys Gly Gly Arg Tyr Val Glu Thr Val Asn Ser Gly Ser Lys Ser
 50                  55                  60

Phe Ser Leu Arg Ile Asn Asp Leu Thr Val Glu Asp Ser Gly Thr Tyr
 65                  70                  75                  80

Arg Cys Asn Val Tyr Met Thr Ala Cys Ser Asn Asp Met Asp Val Tyr
             85                  90                  95
```

Gly Gly Gly Thr Val Val Thr Val Asn Ala
            100             105

<210> SEQ ID NO 34
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gln Gln Gln Ser Ser Gly Thr Phe Tyr Asp Val
                85                  90                  95

Tyr Gly Gly Gly Thr Ala Val Thr Val Asn Ala
            100                 105

<210> SEQ ID NO 35
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Ala Arg Val Asp Gln Thr Pro Gln Thr Val Thr Lys Glu Thr Gly Glu
1               5                   10                  15

Ser Leu Thr Ile Asn Cys Val Leu Arg Asp Ser Asn Cys Asp Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gly Gly Asp Leu Cys Gly Asp Gln Arg Asp Val
                85                  90                  95

Tyr Gly Gly Gly Thr Ala Val Thr Val Asn Ala
            100                 105

<210> SEQ ID NO 36
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Lys Asp Ser Gly Thr
65                  70                  75                  80

Tyr Arg Cys Lys Val Gly Pro Arg Cys Met Gly Pro Asn Trp Gln Ser
                85                  90                  95

Tyr Ser Cys Asp Val Tyr Gly Gly Gly Thr Val Val Thr Val Asn Ala
                100                 105                 110

<210> SEQ ID NO 37
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Phe Thr Glu Met Arg Gly Arg Cys Trp Ala Trp
                85                  90                  95

Gly Val Asp Val Tyr Gly Asp Gly Thr Ala Val Thr Val Asn Ala
                100                 105                 110

<210> SEQ ID NO 38
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Leu Trp Tyr Arg Thr Lys Ser Gly Ser Arg Asn Glu Glu Ser
        35                  40                  45

Ile Ser Lys Gly Gly Arg Tyr Val Glu Thr Val Asn Ser Gly Ser Lys
            50                  55                  60

Ser Phe Ser Leu Lys Ile Asn Asp Leu Thr Val Glu Asp Ser Gly Thr
65                  70                  75                  80

Tyr Arg Cys Asn Val Cys Met Gly Val Thr Cys Asn His Val Pro Asp
                85                  90                  95

Val Tyr Gly Gly Gly Thr Val Val Thr Val Asn Ala
            100                 105

<210> SEQ ID NO 39
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
            50                  55                  60

Ser Phe Ser Leu Arg Ile Asn Asp Leu Thr Val Glu Asp Ser Gly Thr
65                  70                  75                  80

Tyr Arg Cys Asn Val Ser Arg Ile Gly Gln Tyr Leu Cys Gln Ala Arg
                85                  90                  95

Ser Asp Val Tyr Gly Asp Gly Thr Ala Val Thr Val Asn Ala
            100                 105                 110

<210> SEQ ID NO 40
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 40

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
            20                  25                  30

Ser Thr His Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
            50                  55                  60

Ser Phe Ser Leu Arg Ile Asn Asp Leu Thr Val Glu Asp Ser Gly Thr
65                  70                  75                  80

Tyr Arg Cys Asn Val Arg Thr Ala Gln Gly Thr Leu Cys Gly Asp Val
                85                  90                  95

Ser Asp Val Tyr Gly Asp Gly Thr Ala Val Thr Val Asn Ala
            100                 105                 110

<210> SEQ ID NO 41
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 41

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Leu Trp Tyr Arg Thr Lys Ser Gly Ser Arg Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gln Gln Gly Cys Glu Ser Tyr Asn Trp Met Val
                85                  90                  95

Asp Val Tyr Gly Gly Gly Thr Ala Val Thr Val Asn Ala
            100                 105
```

<210> SEQ ID NO 42
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 42

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Leu Trp Tyr Arg Thr Lys Ser Gly Ser Arg Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Trp Phe Ala Asp Tyr Tyr Trp Phe Gln Tyr Asp
                85                  90                  95

Val Tyr Gly Gly Gly Thr Ala Val Thr Val Asn Ala
            100                 105
```

<210> SEQ ID NO 43
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

```
<400> SEQUENCE: 43

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Asp Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Gln Pro Leu Phe Cys Asp Leu Trp Leu Asp Val
                85                  90                  95

Tyr Gly Gly Gly Thr Val Val Thr Val Asn Ala
            100                 105

<210> SEQ ID NO 44
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 44

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gln Asp Met Leu Thr Pro Asn Asp Gly Gln Leu
                85                  90                  95

Trp Asp Val Tyr Gly Asp Gly Thr Ala Val Thr Val Asn Ala
            100                 105                 110

<210> SEQ ID NO 45
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Pro Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45
```

Ile Ser Lys Gly Gly Arg Tyr Val Glu Thr Val Asn Ser Gly Ser Lys
            50                  55                  60

Ser Phe Ser Leu Arg Ile Asn Asp Leu Thr Val Glu Asp Ser Gly Thr
 65                  70                  75                  80

Tyr Arg Cys Asn Val Leu Val Gly Met Leu Ser Gly Cys Gly Phe Gln
                85                  90                  95

Arg Gly Asp Val Tyr Gly Gly Gly Thr Ala Val Thr Val Asn Ala
                100                 105                 110

<210> SEQ ID NO 46
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Pro Arg Val Asp Gln Thr Pro Gln Thr Ile Thr Lys Glu Thr Gly Glu
 1                   5                  10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
            50                  55                  60

Ser Phe Ser Leu Arg Ile Asn Asp Leu Thr Val Glu Asp Ser Gly Thr
 65                  70                  75                  80

Tyr Arg Cys Asn Val Ser Ser Asn Ala His Cys Asp Gly Arg Arg Arg
                85                  90                  95

Asp Val Tyr Gly Gly Gly Thr Ala Val Thr Val Asn Ala
                100                 105

<210> SEQ ID NO 47
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Ala Arg Val Asp Gln Thr Pro Gln Thr Ile Thr Lys Glu Thr Gly Glu
 1                   5                  10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Asp Ser Thr Asn Glu Glu Ser
            35                  40                  45

Ile Ser Lys Gly Gly Arg Tyr Val Glu Thr Val Asn Ser Gly Ser Lys
            50                  55                  60

Ser Phe Ser Leu Arg Ile Asn Asp Leu Thr Val Lys Asp Ser Gly Thr
 65                  70                  75                  80

Tyr Arg Cys Asn Val Ser Glu Asp Leu Gln Ala Ile Cys Cys Trp Asn
                85                  90                  95

Asp Val Tyr Gly Asp Gly Thr Ala Val Thr Val Asn Ala
                100                 105

<210> SEQ ID NO 48
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Val Val Glu Asp Ser Gly Thr
65                  70                  75                  80

Tyr Arg Cys Asn Val His Cys Tyr Gly Gly Asp Leu His Gln Leu Asp
                85                  90                  95

Val Tyr Gly Gly Gly Thr Ala Val Thr Val Asn Ala
            100                 105

<210> SEQ ID NO 49
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 49

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Arg Ile Ile Gln Cys Cys Val Ser Gln Asp Val
                85                  90                  95

Tyr Gly Gly Gly Thr Val Val Thr Val Asn Ala
            100                 105

<210> SEQ ID NO 50
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 50

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Glu Leu Ser
            20                  25                  30

Ser Thr Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gln Ser Ala Met Leu Met Leu Cys Leu Ser Arg
                85                  90                  95

Phe Asp Val Tyr Gly Gly Gly Thr Ala Val Thr Val Asn Ala
            100                 105                 110

<210> SEQ ID NO 51
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 51

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Val Gln Phe Glu Lys Asp Cys Gln Gly Leu Leu
                85                  90                  95

Arg Gln Thr Asn Asp Val Tyr Gly Gly Gly Thr Val Val Thr Val Asn
            100                 105                 110

Ala

<210> SEQ ID NO 52
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 52

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

```
Ile Ser Leu Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Thr Cys Glu Val Ala Leu Gln Pro Tyr Tyr Gly
                85                  90                  95

Gln Glu Pro Thr Gln Asp Val Tyr Gly Gly Thr Val Val Thr Val
                100                 105                 110

Asn Ala

<210> SEQ ID NO 53
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Glu Leu Ser
                20                  25                  30

Ser Thr Tyr Trp Tyr Arg Lys Lys Ser Gly Ser Thr Asn Glu Ala Arg
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Arg Lys Ala Leu Val Gln Ser Gln Ser Cys Cys
                85                  90                  95

Gln Pro Leu His Arg Asp Val Tyr Gly Asp Gly Thr Ala Val Thr Val
                100                 105                 110

Asn Ala

<210> SEQ ID NO 54
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Ser Asp Phe Met Trp Glu Ser Cys Ser Gln Ala
                85                  90                  95
```

Ala Asp Val Tyr Gly Gly Gly Thr Ala Val Thr Val Asn Ala
            100                 105                 110

<210> SEQ ID NO 55
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 55

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Glu Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Ala Gly Ser Val Gln Arg Ser Thr Ser Gln Cys Asp
                85                  90                  95

Arg Leu Trp Ser Arg Cys Trp Arg Thr Arg Phe Lys Ile Ala Ala Cys
            100                 105                 110

Gly Asp Gly Thr Ala Val Thr Val Asn Ala
            115                 120

<210> SEQ ID NO 56
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56

Ala Val Asp Gln Thr Pro Gln Thr Ile Thr Lys Glu Thr Gly Glu Ser
1               5                   10                  15

Leu Thr Ile Asn Cys Val Leu Arg Asp Ser Asn Cys Ala Leu Ser Asn
            20                  25                  30

Leu Tyr Trp Tyr Arg Lys Lys Ser Asp Ser Thr Asn Glu Glu Ser Ile
        35                  40                  45

Ser Lys Gly Gly Arg Tyr Val Glu Thr Val Asn Ser Gly Ser Lys Ser
    50                  55                  60

Phe Ser Leu Arg Ile Asn Asp Leu Thr Val Glu Asp Ser Gly Thr Tyr
65                  70                  75                  80

Arg Cys Asn Val Cys Trp Trp Phe Ser Ser Arg Cys Thr Thr Cys Asp
                85                  90                  95

Val Tyr Gly Asp Gly Thr Ala Val Thr Val Asn Ala
            100                 105

<210> SEQ ID NO 57
<211> LENGTH: 121
<212> TYPE: PRT
<213> ORGANISM: Artificial Sequence
<220> FEATURE:

<221> NAME/KEY: source
<223> OTHER INFORMATION: /note="Description of Artificial Sequence:
      Synthetic polypeptide"

<400> SEQUENCE: 57

```
Ala Arg Val Asp Gln Thr Pro Arg Val Thr Lys Glu Thr Gly Glu Ser
1               5                   10                  15

Leu Thr Ile Asn Cys Val Leu Arg Asp Ala Ser Tyr Glu Leu Gly Ser
            20                  25                  30

Thr Cys Trp Tyr Arg Lys Lys Ser Gly Ser Thr Asn Glu Glu Ser Ile
        35                  40                  45

Ser Lys Gly Gly Arg Tyr Val Glu Thr Val Asn Ser Gly Ser Lys Ser
    50                  55                  60

Phe Ser Leu Arg Ile Asn Asp Leu Thr Val Glu Asp Gly Gly Thr Tyr
65                  70                  75                  80

Arg Cys Gly Ala Ser Gly Ser Gln Gly Gln Val Tyr Arg Cys Asp Arg
                85                  90                  95

Leu Thr Leu Cys Cys Leu Gln Met Gln Trp Gln Val Ala Ala Cys Gly
            100                 105                 110

Asp Gly Thr Ala Val Thr Val Asn Ala
        115                 120
```

<210> SEQ ID NO 58
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 58

```
Pro Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Ile Ile Asn Pro Leu Ser Cys Tyr Tyr Leu Gln
                85                  90                  95

Leu Gln Asp Val Tyr Gly Gly Gly Thr Ala Val Thr Val Asn Ala
            100                 105                 110
```

<210> SEQ ID NO 59
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 59

```
Ala Arg Val Asp Gln Thr Pro Arg Ser Val Thr Lys Glu Thr Gly Glu
1               5                   10                  15
```

```
Ser Leu Thr Ile Asn Cys Val Leu Arg Asp Ala Ser Tyr Glu Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Thr
65                  70                  75              80

Tyr Arg Cys Gly Ala Ser Phe Met Leu Ser His Pro Gly Cys Asp
                85                  90                  95

Ser Cys Val Ile Met Cys Gln Thr Arg Arg Gln Gly Val Ala Ala Cys
            100                 105                 110

Gly Asp Gly Thr Ala Val Thr Val Asn Ala
            115                 120
```

<210> SEQ ID NO 60
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 60

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Gln Gly Arg Ala Ala Tyr Ser Gly Leu Val Cys
                85                  90                  95

Asp Val Tyr Gly Gly Gly Thr Ala Val Thr Val Asn Ala
            100                 105
```

<210> SEQ ID NO 61
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 61

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Asp Ser Thr Asn Glu Glu Ser
        35                  40                  45

Ile Ser Lys Gly Gly Arg Tyr Val Glu Thr Val Asn Ser Gly Ser Lys
    50                  55                  60
```

Ser Phe Ser Leu Arg Ile Asn Asp Leu Thr Val Lys Asp Ser Gly Thr
65                  70                  75                  80

Tyr Arg Cys Asn Val Leu Ile Gln Cys Cys Ser Pro Thr Cys Asp Val
                85                  90                  95

Tyr Gly Gly Gly Thr Ala Val Thr Val Asn Ala
            100                 105

<210> SEQ ID NO 62
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 62

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Leu Trp Tyr Arg Thr Lys Ser Gly Ser Arg Asn Glu Glu Ser
            35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Val Val Glu Asp Ser Gly Thr
65                  70                  75                  80

Tyr Arg Cys Lys Val Ser His Ser Gly Leu Cys Gln Tyr Cys His Asp
                85                  90                  95

Leu Glu Asp Asp Val Tyr Gly Asp Gly Thr Ala Val Thr Val Asn Ala
            100                 105                 110

<210> SEQ ID NO 63
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 63

Pro Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Gly Ser Thr Asn Glu Glu Asn
            35                  40                  45

Ile Ser Lys Gly Gly Arg Tyr Val Glu Thr Val Asn Ser Gly Ser Lys
50                  55                  60

Ser Phe Ser Leu Arg Ile Asn Asp Leu Thr Val Glu Asp Ser Gly Thr
65                  70                  75                  80

Tyr Arg Cys Asn Val Ala Phe Phe Ala Cys Gln Tyr Lys Asn Asp Val
                85                  90                  95

Tyr Gly Gly Gly Thr Val Val Thr Val Asn Ala
            100                 105

<210> SEQ ID NO 64
<211> LENGTH: 111
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 64

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Asp Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Lys Asp Ser Gly Thr
65                  70                  75                  80

Tyr Arg Cys Asn Val Tyr Leu Gln Asp Arg Pro Val Cys Ser Pro Phe
                85                  90                  95

Asn Tyr Asp Val Tyr Gly Gly Gly Thr Ala Val Thr Val Asn Ala
            100                 105                 110
```

<210> SEQ ID NO 65
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 65

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ile Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Lys Asp Ser Gly Thr
65                  70                  75                  80

Tyr Arg Cys Asn Val Gly Ala Gln Tyr Cys Asp Arg Glu Ile Ser Asp
                85                  90                  95

Val Tyr Gly Asp Gly Thr Ala Val Thr Val Asn Ala
            100                 105
```

<210> SEQ ID NO 66
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 66

```
Pro Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30
```

Ser Thr Leu Trp Tyr Arg Thr Lys Ser Gly Ser Arg Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Trp Cys Leu Thr Leu Gly Cys Ser Gly Lys Trp
                85                  90                  95

Asp Val Tyr Gly Gly Gly Thr Ala Val Thr Val Asn Ala
                100                 105

<210> SEQ ID NO 67
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 67

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Ser Thr Tyr Trp Tyr Arg Lys Lys Ser Asp Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Val Val Glu Asp Ser Gly Thr
65                  70                  75                  80

Tyr Arg Cys Asn Val Gln Ser Lys Glu Lys Leu His Cys Gln Val Val
                85                  90                  95

Val Asp Val Tyr Gly Gly Gly Thr Ala Val Thr Val Asn Ala
                100                 105                 110

<210> SEQ ID NO 68
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 68

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
                20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Arg Gly Phe Lys Gln Cys Tyr Asp Leu Arg Leu
                85                  90                  95

```
Asp Val Tyr Gly Gly Thr Ala Val Thr Val Asn Ala
            100                 105
```

<210> SEQ ID NO 69
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 69

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Glu Leu Ser
            20                  25                  30

Ser Thr Tyr Trp Tyr Arg Lys Lys Ser Gly Ser Thr Asn Glu Ala Arg
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Gly Phe Ser Gln Ser Trp Gly Asn Ser Val Gly
                85                  90                  95

Ile Val Asp Val Tyr Gly Gly Thr Ala Val Thr Val Asn Glu
            100                 105                 110
```

<210> SEQ ID NO 70
<211> LENGTH: 107
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 70

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Ser Leu Gln Phe Cys Cys Leu Ser Phe Asp Val
                85                  90                  95

Tyr Gly Gly Gly Thr Ala Val Thr Val Asn Ala
            100                 105
```

<210> SEQ ID NO 71
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 71

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Tyr Asn Pro Gly Asn Gly Trp Ala Met Tyr Asp
                85                  90                  95

Val Tyr Gly Gly Gly Thr Ala Val Thr Val Asn Ala
            100                 105
```

<210> SEQ ID NO 72
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 72

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Trp Tyr Arg Lys Lys Ser Asp Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Lys Val Leu Ser Val Gln Arg Leu Phe Cys Ala Ile Phe
                85                  90                  95

Ala Ser Glu Asp Val Tyr Gly Asp Gly Thr Ala Val Thr Val Asn Ala
            100                 105                 110
```

<210> SEQ ID NO 73
<211> LENGTH: 112
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 73

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
            20                  25                  30

Ser Thr Tyr Gln Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60
```

```
Ser Phe Ser Leu Arg Ile Asn Asp Leu Thr Val Lys Asp Ser Gly Thr
 65                  70                  75                  80

Tyr Arg Cys Asn Val Leu Ser Val Gln Arg Leu Phe Cys Ala Ile Phe
                 85                  90                  95

Ala Ser Glu Asp Val Tyr Gly Asp Gly Thr Ala Val Thr Val Asn Ala
            100                 105                 110
```

<210> SEQ ID NO 74
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 74

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Pro
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Lys Ile Asn Asp Leu Thr Val Glu Asp Ser Gly Thr
 65                  70                  75                  80

Tyr Arg Cys Lys Val Ala Asn Glu Tyr Trp Leu Arg Leu Asn Gln Cys
                 85                  90                  95

Phe Tyr Leu Gln His Asp Val Tyr Gly Gly Gly Thr Val Thr Val
            100                 105                 110

Asn Ala
```

<210> SEQ ID NO 75
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 75

```
Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                 20                  25                  30

Ser Thr Tyr Trp Tyr Arg Lys Lys Ser Gly Ser Thr Asn Glu Glu Ser
             35                  40                  45

Ile Ser Lys Gly Gly Arg Tyr Val Glu Thr Val Asn Ser Gly Ser Lys
 50                  55                  60

Ser Phe Ser Leu Arg Ile Asn Asp Leu Thr Val Glu Asp Ser Gly Thr
 65                  70                  75                  80

Tyr Arg Cys Asn Val Gln Leu Gln Phe Asp Cys Lys Glu Trp Glu Asp
                 85                  90                  95

Val Tyr Gly Gly Gly Thr Val Val Thr Val Asn Ala
            100                 105
```

<210> SEQ ID NO 76
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 76

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Ile Cys Ala Leu Ser
                20                  25                  30

Ser Thr His Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Lys Val Thr Val Thr Lys Trp Cys Cys Lys Gln Arg Asp
                85                  90                  95

Gly Cys Thr Gly Asp Val Tyr Gly Gly Thr Ala Val Thr Val Asn
            100                 105                 110

Ala

<210> SEQ ID NO 77
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 77

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Ile Cys Ala Leu Ser
                20                  25                  30

Ser Thr His Trp Tyr Arg Lys Lys Ser Gly Ser Thr Asn Gln Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Val Gln Lys Gly Arg Ile Lys Cys Ser Arg Met
                85                  90                  95

Leu Glu Asp Val Tyr Gly Gly Thr Val Val Thr Met Asn Ala
            100                 105                 110

<210> SEQ ID NO 78
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 78

Ala Arg Val Asp Gln Thr Pro Gln Thr Ile Thr Lys Glu Thr Gly Glu
1               5                   10                  15

Ser Leu Thr Ile Asn Cys Val Leu Arg Asp Asn Asn Cys Ala Ser Ser
            20                  25                  30

Thr Thr Tyr Trp Tyr Arg Lys Lys Ser Gly Ser Thr Asn Glu Glu Asn
        35                  40                  45

Ile Ser Lys Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Arg Asp Val Gln Ala Cys Gly Asn Asp Trp Val
                85                  90                  95

Trp Leu Asp Val Tyr Gly Gly Gly Thr Val Val Thr Val Asn Ala
            100                 105                 110

<210> SEQ ID NO 79
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 79

Pro Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Ser Gly Gly Arg Gly Val Cys Trp Gln Gly
                85                  90                  95

Ser Asp Val Tyr Gly Gly Gly Thr Val Val Thr Val Asn Ala
            100                 105                 110

<210> SEQ ID NO 80
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 80

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ile Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                      55                  60

Ser Phe Ser Leu Arg Ile Asn Asp Leu Thr Val Lys Asp Ser Gly Thr
65                  70                  75                  80

Tyr Arg Cys Asn Val Pro Ala Gln Leu Leu Tyr Ser Gly Gln Gln
                85                  90                  95

Gly Val Asp Val Tyr Gly Asp Gly Thr Val Thr Val Asn Ala
            100                 105                 110

<210> SEQ ID NO 81
<211> LENGTH: 121
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 81

Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Glu Leu Gly
                20                  25                  30

Ser Thr Cys Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                      55                  60

Ser Phe Ser Leu Arg Ile Asn Asp Leu Thr Val Glu Asp Gly Gly Thr
65                  70                  75                  80

Tyr Arg Cys Gly Ala Leu Ile Gln Ser His Arg Asn Gly Arg Cys Asp
                85                  90                  95

Gly Trp Phe Asp Ile Cys Pro Thr Ser Leu Gly Gly Ala Ala Cys Gly
            100                 105                 110

Asp Gly Thr Ala Val Thr Val Asn Ala
            115                 120

<210> SEQ ID NO 82
<211> LENGTH: 111
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 82

Ala Arg Val Asp Gln Thr Pro Gln Thr Val Thr Lys Glu Thr Gly Glu
1               5                   10                  15

Ser Leu Thr Ile Asn Cys Val Leu Arg Asp Ser Asn Cys Ala Leu Pro
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
    50                      55                  60

Ser Phe Ser Leu Arg Ile Asn Asp Leu Thr Val Glu Asp Ser Gly Thr
65                  70                  75                  80

Tyr Arg Cys Asn Val Ile Trp Leu Gln Val Gly Val Cys Asp Asp Tyr
                85                  90                  95

```
Pro Tyr Asp Val Tyr Gly Asp Gly Thr Ala Val Thr Val Asn Ala
            100                 105                 110
```

<210> SEQ ID NO 83
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 83

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Asn Val Asp Gly Trp Ser Leu Cys Gln Glu Leu Cys Asp
                85                  90                  95

Val Tyr Gly Gly Gly Thr Val Val Thr Val Asn Thr
            100                 105
```

<210> SEQ ID NO 84
<211> LENGTH: 122
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 84

```
Ala Arg Val Asp Gln Thr Pro Arg Ser Val Thr Lys Glu Thr Gly Glu
1               5                   10                  15

Ser Leu Thr Ile Asn Cys Val Leu Arg Asp Ala Ser Tyr Ala Leu Gly
            20                  25                  30

Ser Thr Cys Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Gly Gly Thr
65                  70                  75                  80

Tyr Arg Cys Gly Val Ser Leu Arg Gly Lys Thr Met Arg Gly Glu Cys
                85                  90                  95

Asp Tyr Gln Val Ser Val Gly Leu Cys Gly Gly Gln Ala Ala Ala Cys
            100                 105                 110

Gly Asp Gly Thr Ala Val Thr Val Asn Ala
        115                 120
```

<210> SEQ ID NO 85
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 85

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Asp Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Val Val Glu Asp Ser Gly Thr
65                  70                  75                  80

Tyr Arg Cys Asn Val Met Arg Leu Glu Arg Cys Arg Gln Asn Gly Asp
                85                  90                  95

Val Tyr Gly Gly Gly Thr Ala Val Thr Val Asn Ala
            100                 105

<210> SEQ ID NO 86
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 86

Ala Arg Val Asp Gln Thr Pro Gln Thr Val Thr Lys Glu Thr Gly Glu
1               5                   10                  15

Ser Leu Thr Ile Asn Cys Val Leu Arg Asp Ser Asn Cys Ala Leu Ser
            20                  25                  30

Asn Leu Tyr Trp Tyr Arg Lys Lys Ser Gly Ser Thr Asn Glu Glu Ser
        35                  40                  45

Ile Ser Leu Gly Gly Arg Tyr Val Glu Thr Val Asn Ser Gly Ser Lys
    50                  55                  60

Ser Phe Ser Leu Lys Ile Asn Asp Leu Thr Val Glu Asp Ser Gly Thr
65                  70                  75                  80

Tyr Arg Cys Asn Val Pro Ala Leu Gln Val Cys Cys Asp Gly Thr Gln
                85                  90                  95

Leu Asp Val Tyr Gly Gly Gly Thr Ala Val Thr Val Asn Ala
            100                 105                 110

<210> SEQ ID NO 87
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 87

Ala Arg Val Asp Gln Thr Pro Gln Thr Ile Thr Lys Glu Thr Gly Ser
1               5                   10                  15

Leu Thr Ile Asn Cys Val Leu Arg Asp Ser Asn Cys Asp Leu Ser Arg
            20                  25                  30

Thr Tyr Trp Tyr Arg Lys Lys Ser Gly Ser Thr Asn Glu Glu Ser Ile
        35                  40                  45

Ser Lys Gly Gly Arg Tyr Val Glu Thr Val Asn Ser Gly Ser Lys Ser
            50                  55                  60

Phe Ser Leu Arg Ile Asn Asp Leu Val Val Glu Asp Ser Gly Thr Tyr
 65                  70                  75                  80

Arg Cys Asn Val Pro Val Gly His Cys Cys Tyr Cys Ala Gly Phe Asp
                    85                  90                  95

Val Tyr Gly Asp Gly Thr Val Val Thr Val Asn Ala
                100                 105

<210> SEQ ID NO 88
<211> LENGTH: 110
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 88

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Pro
                20                  25                  30

Ser Thr Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Lys Asp Ser Gly Thr
 65                  70                  75                  80

Tyr Arg Cys Asn Val Phe Ile Leu Gly Gln Leu Tyr Gly Tyr Asp Tyr
                85                  90                  95

Leu Asp Val Tyr Gly Gly Gly Thr Ala Val Thr Val Asn Ala
                100                 105                 110

<210> SEQ ID NO 89
<211> LENGTH: 114
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 89

Ala Arg Val Asp Gln Thr Pro Gln Thr Ile Thr Lys Glu Thr Gly Glu
 1               5                  10                  15

Ser Leu Thr Ile Asn Cys Val Leu Arg Asp Ser Asn Cys Ala Leu Ser
                20                  25                  30

Asn Leu Tyr Trp Tyr Arg Lys Lys Ser Gly Ser Thr Asn Glu Glu Ser
            35                  40                  45

Ile Ser Leu Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
 65                  70                  75                  80

Tyr Arg Cys Lys Val Ser Arg Arg Ala Gln Arg Leu Val Ser Asp Asp
                85                  90                  95

```
Gln Ser Ala Trp Met Asp Val Tyr Gly Gly Gly Thr Val Val Thr Val
                100                 105                 110

Asn Ala

<210> SEQ ID NO 90
<211> LENGTH: 115
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 90

Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Ser
                20                  25                  30

Asn Leu Tyr Trp Tyr Arg Lys Lys Ser Gly Ser Thr Asn Glu Glu Ser
            35                  40                  45

Ile Ser Lys Gly Gly Arg Tyr Val Glu Thr Val Asn Ser Gly Ser Lys
        50                  55                  60

Ser Phe Ser Leu Arg Ile Asn Asp Leu Thr Val Lys Asp Ser Gly Thr
65                  70                  75                  80

Tyr Arg Cys Lys Val Gly Ala Glu Arg Tyr Lys Ser Ser Trp Gln Cys
                85                  90                  95

Met Gly Arg Ser Ala Ser Asp Val Tyr Gly Gly Gly Thr Val Val Thr
                100                 105                 110

Val Asn Ala
        115

<210> SEQ ID NO 91
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 91

Ala Arg Val Asp Gln Thr Pro Arg Ser Val Thr Lys Glu Thr Gly Glu
1               5                   10                  15

Ser Leu Thr Ile Asn Cys Val Leu Arg Asp Ser Asn Cys Asp Leu Ser
                20                  25                  30

Arg Thr Tyr Trp Tyr Arg Lys Lys Ser Gly Ser Thr Asn Glu Glu Ser
            35                  40                  45

Ile Ser Leu Gly Gly Arg Tyr Val Glu Thr Val Asn Ser Gly Ser Lys
        50                  55                  60

Ser Phe Ser Leu Arg Ile Asn Asp Leu Thr Val Glu Asp Ser Gly Thr
65                  70                  75                  80

Tyr Arg Cys Asn Val Glu Cys Gly Thr Phe Gly Tyr Ser Gln Cys Arg
                85                  90                  95

Asp Val Tyr Gly Asp Gly Thr Ala Val Thr Val Asn Ala
                100                 105

<210> SEQ ID NO 92
<211> LENGTH: 108
<212> TYPE: PRT
```

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 92

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Asp Leu Ser
            20                  25                  30

Arg Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Val Val Glu Asp Ser Gly Thr
65                  70                  75                  80

Tyr Arg Cys Asn Val Tyr Asn Pro Ser Ser Tyr Thr Ser Val Cys Asp
                85                  90                  95

Val Tyr Gly Gly Gly Thr Ala Val Thr Val Asn Ala
            100                 105
```

<210> SEQ ID NO 93
<211> LENGTH: 113
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 93

```
Ala Arg Val Asp Gln Thr Pro Gln Thr Ile Thr Lys Glu Thr Gly Glu
1               5                   10                  15

Ser Leu Thr Ile Asn Cys Val Leu Arg Asp Ser Asn Cys Ala Leu Pro
            20                  25                  30

Ser Thr Tyr Trp Tyr Arg Lys Lys Ser Gly Ser Thr Asn Glu Glu Ser
        35                  40                  45

Ile Ser Lys Gly Gly Arg Tyr Val Glu Thr Val Asn Ser Gly Ser Lys
    50                  55                  60

Ser Phe Ser Leu Arg Ile Asn Asp Leu Thr Val Glu Asp Ser Gly Thr
65                  70                  75                  80

Tyr Arg Cys Lys Val Met Asn Lys Ser Tyr Arg Cys Gln Arg Gly Leu
                85                  90                  95

Pro Leu Pro Arg Asp Val Tyr Gly Asp Gly Thr Ala Val Thr Val Asn
            100                 105                 110

Ala
```

<210> SEQ ID NO 94
<211> LENGTH: 108
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 94

```
Ala Arg Val Asp Gln Thr Pro Gln Thr Ile Thr Lys Glu Thr Gly Glu
1               5                   10                  15
```

Ser Leu Thr Ile Asn Cys Val Leu Arg Asp Ser Asn Cys Ala Leu Ser
                20                  25                  30

Asn Leu Tyr Trp Tyr Arg Lys Lys Ser Gly Ser Thr Asn Glu Glu Ser
            35                  40                  45

Ile Ser Leu Gly Gly Arg Tyr Val Glu Thr Val Asn Ser Gly Ser Lys
 50                  55                  60

Ser Phe Ser Leu Lys Ile Asn Asp Leu Thr Val Glu Asp Ser Gly Thr
65                  70                  75                  80

Tyr Arg Cys Asn Val Gln Leu Ser Asn Tyr Tyr Val Asp Trp Tyr Asp
                85                  90                  95

Val Tyr Gly Gly Gly Thr Val Val Thr Val Asn Ala
            100                 105

<210> SEQ ID NO 95
<211> LENGTH: 109
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 95

Ala Arg Val Asp Gln Thr Pro Gln Thr Ile Thr Lys Glu Thr Gly Glu
1               5                   10                  15

Ser Leu Thr Ile Asn Cys Val Leu Arg Ala Asp Ser Asn Cys Glu Leu
                20                  25                  30

Ser Ser Thr Tyr Trp Tyr Arg Lys Lys Ser Gly Ser Thr Asn Glu Ala
            35                  40                  45

Arg Ile Ser Lys Gly Gly Arg Tyr Val Glu Thr Val Asn Ser Gly Ser
 50                  55                  60

Lys Ser Phe Ser Leu Arg Ile Asn Asp Leu Thr Val Glu Asp Ser Gly
65                  70                  75                  80

Thr Tyr Arg Cys Asn Val Phe Ala Gln Arg His Cys Gly Tyr Tyr Arg
                85                  90                  95

Asp Val Tyr Gly Asp Gly Thr Ala Val Thr Val Asn Ala
            100                 105

<210> SEQ ID NO 96
<211> LENGTH: 32
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: SITE
<222> LOCATION: (1)..(4)
<223> OTHER INFORMATION: /note="This region may encompass 0-4 residues"
<220> FEATURE:
<221> NAME/KEY: SITE
<222> LOCATION: (5)..(8)
<223> OTHER INFORMATION: /note="This region may encompass 0-4 residues"
<220> FEATURE:
<221> NAME/KEY: SITE
<222> LOCATION: (9)..(12)
<223> OTHER INFORMATION: /note="This region may encompass 0-4 residues"
<220> FEATURE:
<221> NAME/KEY: SITE
<222> LOCATION: (13)..(16)
<223> OTHER INFORMATION: /note="This region may encompass 0-4 residues"
<220> FEATURE:
<221> NAME/KEY: SITE
<222> LOCATION: (17)..(20)

```
<223> OTHER INFORMATION: /note="This region may encompass 0-4 residues"
<220> FEATURE:
<221> NAME/KEY: SITE
<222> LOCATION: (21)..(24)
<223> OTHER INFORMATION: /note="This region may encompass 0-4 residues"
<220> FEATURE:
<221> NAME/KEY: SITE
<222> LOCATION: (25)..(28)
<223> OTHER INFORMATION: /note="This region may encompass 0-4 residues"
<220> FEATURE:
<221> NAME/KEY: SITE
<222> LOCATION: (29)..(32)
<223> OTHER INFORMATION: /note="This region may encompass 0-4 residues"
<220> FEATURE:
<221> NAME/KEY: SITE
<222> LOCATION: (1)..(32)
<223> OTHER INFORMATION: /note="This sequence may encompass 0-4 'Glyx
      Serx' repeating units, wherein x = 0-4"

<400> SEQUENCE: 96

Gly Gly Gly Gly Ser Ser Ser Ser Gly Gly Gly Gly Ser Ser Ser Ser
1               5                   10                  15

Gly Gly Gly Gly Ser Ser Ser Ser Gly Gly Gly Gly Ser Ser Ser Ser
            20                  25                  30

<210> SEQ ID NO 97
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 97

Leu Arg Leu Leu Ser Ser Ile Leu Arg Gly Cys Asn Tyr Arg Lys His
1               5                   10                  15

Asp Val

<210> SEQ ID NO 98
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 98

Leu Phe Asn Leu Ser Ser Ile Leu Arg Gly Cys Asn Tyr Arg Lys His
1               5                   10                  15

Asp Val

<210> SEQ ID NO 99
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 99

Val Arg Phe Leu Ser Ser Ile Leu Arg Gly Cys Asn Tyr Arg Lys His
1               5                   10                  15

Asp Val
```

```
<210> SEQ ID NO 100
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 100

Lys Leu Trp Leu Ser Ser Ile Leu Arg Gly Cys Asn Tyr Arg Lys His
1               5                   10                  15

Asp Val

<210> SEQ ID NO 101
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 101

Ile Ala Gln Trp Trp Ser Ile Leu Arg Gly Cys Asn Tyr Arg Lys His
1               5                   10                  15

Asp Val

<210> SEQ ID NO 102
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 102

Ile Ala Gln Leu Ser Ser Ile Leu Lys Ala Cys Lys Tyr Arg Lys His
1               5                   10                  15

Asp Val

<210> SEQ ID NO 103
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 103

Trp Asn Met Leu Ser Ser Ile Leu Arg Gly Cys Asn Tyr Arg Lys His
1               5                   10                  15

Asp Val

<210> SEQ ID NO 104
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 104

Ile Ala Gln Leu Ala Ile Glu Leu Arg Gly Cys Asn Tyr Arg Lys His
1               5                   10                  15

Asp Val

<210> SEQ ID NO 105
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 105

Ile Ala Gln Leu Ser Ser Ile Tyr Pro Gly Cys Asn Tyr Arg Lys His
1               5                   10                  15

Asp Val

<210> SEQ ID NO 106
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 106

Ile Ala Gln Leu Ala Leu Ala Leu Arg Gly Cys Asn Tyr Arg Lys His
1               5                   10                  15

Asp Val

<210> SEQ ID NO 107
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 107

Ile Ala Gln Leu Ser Ser Ile Leu Gly Tyr Cys Tyr Tyr Arg Lys His
1               5                   10                  15

Asp Val

<210> SEQ ID NO 108
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 108

Met Trp Asn Leu Ser Ser Ile Leu Arg Gly Cys Asn Tyr Arg Lys His
1               5                   10                  15

Asp Val

<210> SEQ ID NO 109
<211> LENGTH: 18
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 109

Ile Ala Lys Leu Phe Ser Ile Leu Cys Gly Cys Asn Tyr Arg Lys His
1               5                   10                  15

Asp Val

<210> SEQ ID NO 110
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 110

Ile Ala Tyr Arg Lys Ser Ile Val Arg Gly Cys Asn Tyr Arg Lys His
1               5                   10                  15

Asp Val

<210> SEQ ID NO 111
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 111

Ile Ala Gln Leu Ser Ser Lys Tyr Val Gly Cys Asn Tyr Arg Lys His
1               5                   10                  15

Asp Val

<210> SEQ ID NO 112
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 112

Gln Ser Gln Leu Ser Ile Val Leu Arg Gly Cys Asn Tyr Arg Lys His
1               5                   10                  15

Asp Val

<210> SEQ ID NO 113
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 113

Ile Ala Gln Leu Ser Ser Ile Leu Arg Gly Cys Leu Asp Lys Lys His
1               5                   10                  15

Asp Val

<210> SEQ ID NO 114
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 114

Ile Ala His Leu Ser Ser Phe Arg Asp Gly Cys Asn Tyr Arg Lys His
1               5                   10                  15

Asp Val

<210> SEQ ID NO 115
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 115

Ile Ala Gln Gln Lys Ser Ile Leu Arg Gly Cys Asn Tyr His Lys His
1               5                   10                  15

Asp Val

<210> SEQ ID NO 116
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 116

Ile Ala Gln Leu Pro Lys Gln Leu Arg Gly Cys Asn Tyr Arg Lys His
1               5                   10                  15

Asp Val

<210> SEQ ID NO 117
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 117

Ile Ala Gln Leu Ser Ser Ile Leu Arg Gly Cys Asn Tyr Phe Phe Pro
1               5                   10                  15

Asp Val

<210> SEQ ID NO 118
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 118

Ile Ala Gln Leu Ser Ser Met Glu Leu Gly Cys Asn Tyr Arg Lys His
1               5                   10                  15

Asp Val

<210> SEQ ID NO 119
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 119

Ile Ala Ser Ala Phe Ser Ile Leu Arg Gly Cys Asn Tyr Arg Lys His
1               5                   10                  15

Asp Val

<210> SEQ ID NO 120
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 120

Gln Gly Met Leu Ser Ser Ile Leu Arg Gly Cys Asn Tyr Arg Lys His
1               5                   10                  15

Asp Val

<210> SEQ ID NO 121
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 121

Ala Phe Ile Leu Ser Ser Ile Leu Arg Gly Cys Asn Tyr Arg Lys His
1               5                   10                  15

Asp Val

<210> SEQ ID NO 122
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 122

Ile Ala Gln Leu Ser Ser Ile Leu Leu Thr Cys Glu Tyr Arg Lys His
1               5                   10                  15

Asp Val

<210> SEQ ID NO 123
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 123

Ser Met Leu Leu Ser Ser Ile Leu Arg Gly Cys Asn Tyr Arg Lys His
1               5                   10                  15

Asp Val

<210> SEQ ID NO 124
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 124

Ile Ala Gln Leu Ile Ser Ile Leu Arg Gly Cys Asn Lys Asn Lys His
1               5                   10                  15

Asp Val

<210> SEQ ID NO 125
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 125

Ile Ala Gln Leu Ser Ser Ile Trp Lys Gly Cys Lys Tyr Arg Lys His
1               5                   10                  15

Asp Val

<210> SEQ ID NO 126
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 126

Arg Asp Ala Leu Ser Ser Ile Leu Arg Gly Cys Asn Tyr Arg Lys His
1               5                   10                  15

Asp Val

<210> SEQ ID NO 127
<211> LENGTH: 18

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 127

Ile Ala Gln Leu Ser Ser Ile Leu Arg Gly Cys Asn Tyr Ile Ala Tyr
1               5                   10                  15

Asp Val

<210> SEQ ID NO 128
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 128

Ile Ala Glu Leu Phe Ser Ile Leu Arg Gly Cys Asn Tyr Arg Lys His
1               5                   10                  15

Asp Val

<210> SEQ ID NO 129
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 129

Ile Ala Gln Leu Ser Ser Ile Leu Arg Gly Cys Asn Tyr Trp Arg Trp
1               5                   10                  15

Asp Val

<210> SEQ ID NO 130
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 130

Ile Ala Gln Leu Ser Ser Gln Arg Trp Gly Cys Asn Tyr Arg Lys His
1               5                   10                  15

Asp Val

<210> SEQ ID NO 131
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 131

Ile Ala Gln Leu Val Leu Asn Leu Arg Gly Cys Asn Tyr Arg Lys His
1               5                   10                  15

Asp Val

<210> SEQ ID NO 132
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 132

Ile Ala Gln Leu Ser Ser Ile Leu Asp Asp Cys Glu Tyr Arg Lys His
1               5                   10                  15

Asp Val

<210> SEQ ID NO 133
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 133

Ile Ala Gln Leu Tyr Val Gly Leu Arg Gly Cys Asn Tyr Arg Lys His
1               5                   10                  15

Asp Val

<210> SEQ ID NO 134
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 134

Ile Ala Pro Gln Lys Ser Ile Leu Arg Gly Cys Asn Tyr His Lys Ile
1               5                   10                  15

Asp Val

<210> SEQ ID NO 135
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 135

Ile Ala Gln Leu Phe Ile Asp Leu Arg Gly Cys Asn Tyr Arg Lys His
1               5                   10                  15

Asp Val

<210> SEQ ID NO 136
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 136

Ile Ala Gln Leu Ser Ser Ile Leu Lys Pro Cys Trp Tyr Arg Lys His
1               5                   10                  15

Asp Val

<210> SEQ ID NO 137
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 137

Ile Ala Gln Leu Ser Ser Ile Leu Arg Gly Cys Asn Tyr Leu Ser Met
1               5                   10                  15

Asp Val

<210> SEQ ID NO 138
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 138

Ile Ala Gln Leu Ser Ser Ile Leu Arg Gly Cys Asn Tyr Asn Met Glu
1               5                   10                  15

Asp Val

<210> SEQ ID NO 139
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 139

Ile Ala Gln Leu Ser Ser Tyr Val Val Gly Cys Asn Tyr Arg Lys His
1               5                   10                  15

Asp Val

<210> SEQ ID NO 140
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 140

Gln Thr Thr Leu Ser Ser Ile Leu Arg Gly Cys Asn Tyr Arg Lys His
1               5                   10                  15

Asp Val

<210> SEQ ID NO 141
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 141

Ile Ala Gln Leu Ser Ser Ile Leu Arg Gly Cys Asn Tyr Met Met Tyr
1               5                   10                  15

Asp Val

<210> SEQ ID NO 142
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 142

Ile Ala Glu Met Gly Ser Ile Leu Arg Gly Cys Asn Tyr Arg Lys His
1               5                   10                  15

Asp Val

<210> SEQ ID NO 143
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 143

Ile Ala Asn Leu Ser Ser Ile Leu Arg Gly Cys Asn Tyr Arg Lys His
1               5                   10                  15

Asp Val

<210> SEQ ID NO 144
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 144

Ile Ala Gln Leu Ser Ser Asp His Pro Gly Cys Asn Tyr Arg Lys His
1               5                   10                  15

Asp Val

<210> SEQ ID NO 145
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 145

Ile Ala Gln Leu Ser Ser Ile Leu Arg Gly Cys Asp Arg Trp Lys His
1               5                   10                  15

Asp Val

<210> SEQ ID NO 146
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 146

Ile Ala Gln Leu Ser Ser Ile Leu Arg Gly Cys Asn Tyr Ala Trp Leu
1               5                   10                  15

Asp Val

<210> SEQ ID NO 147
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 147

Ile Ala Ser Ala Val Ser Ile Leu Arg Gly Cys Asn Tyr Arg Lys His
1               5                   10                  15

Asp Val

<210> SEQ ID NO 148
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 148

Ile Ala Gln Leu Ser Ser Ile Leu Phe Trp Cys Ala Tyr Arg Lys His
1               5                   10                  15

Asp Val

<210> SEQ ID NO 149
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 149

Ile Ala Gln Leu Ser Ser Ile Leu Arg Gly Cys Thr Phe Asp Lys His
1               5                   10                  15

Asp Val

<210> SEQ ID NO 150
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 150

Ile Ala Gln Leu Gly Asn Leu Leu Arg Gly Cys Asn Tyr Arg Lys His
1               5                   10                  15

Asp Val

<210> SEQ ID NO 151
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 151

Ile Ala Gln Leu Ser Ser Ala Gly Met Gly Cys Asn Tyr Arg Lys His
1               5                   10                  15

Asp Val

<210> SEQ ID NO 152
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 152

Ile Ala Gln Leu Ser Ser His Asp His Gly Cys Asn Tyr Arg Lys His
1               5                   10                  15

Asp Val

<210> SEQ ID NO 153
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 153

Ile Ala Gln Leu Ser Ser Ile Leu Leu Thr Cys Leu Tyr Arg Lys His
1               5                   10                  15

Asp Val

<210> SEQ ID NO 154
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 154

Ile Ala Gln Leu Ser Ser Ile Leu Gln Arg Cys Asn Tyr Arg Lys His
1               5                   10                  15

Asp Val

<210> SEQ ID NO 155
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 155

Ile Ala Gln Leu Ser Ser Ile Leu Arg Gly Cys Asn Tyr Ala Ala Gly
1               5                   10                  15

Asp Val

<210> SEQ ID NO 156
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 156

Tyr Arg Tyr Leu Ser Ser Ile Leu Arg Gly Cys Asn Tyr Arg Lys His
1               5                   10                  15

Asp Val

<210> SEQ ID NO 157
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 157

Ile Ala Gln Leu Ala Phe Trp Leu Arg Gly Cys Asn Tyr Arg Lys His
1               5                   10                  15

Asp Val

<210> SEQ ID NO 158
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 158

Ile Ala Gln Leu Ser Ser Ile His Asp Gly Cys Asn Tyr Arg Lys His
1               5                   10                  15

Asp Val

<210> SEQ ID NO 159
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 159

Ile Ala Gln Leu Ser Ser Ile Leu Arg Gly Cys Asn Tyr Leu Ala His
1               5                   10                  15

Asp Val

<210> SEQ ID NO 160
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 160

Ile Ala Gln Leu Ser Ser Ile Leu Arg Gly Cys Val Glu Pro Lys His
1               5                   10                  15

Asp Val

<210> SEQ ID NO 161
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 161

Ile Ala Gln Leu Ser Ser Ile Leu Ser Ser Cys His Tyr Arg Lys His
1               5                   10                  15

Asp Val

<210> SEQ ID NO 162
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 162

Ile Ala Gln Leu Ser Ser Ala Pro Ala Gly Cys Asn Tyr Arg Lys His
1               5                   10                  15

Asp Val

<210> SEQ ID NO 163
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 163

Ile Ala Gln Leu Ser Ser Ile Leu Arg Gly Cys Asn Tyr Gln Thr Ser
1               5                   10                  15

Asp Val

<210> SEQ ID NO 164
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 164

Ile Ala Gln Leu Ser Ser Ile Leu Arg Gly Cys Thr Pro His Lys His
1               5                   10                  15

Asp Val

<210> SEQ ID NO 165
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 165

Ile Ala Gln Leu Ser Ser Ile Leu Arg Gly Cys Ser Gly Val Lys His
1               5                   10                  15

Asp Val

<210> SEQ ID NO 166
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 166

Ile Ala Gln Leu Ser Ser Ile Leu Lys Gly Cys Asn Tyr Arg Lys His
1               5                   10                  15

Asp Val

<210> SEQ ID NO 167
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 167

Ile Ala Gln Leu Ser Ser Leu Gln Asp Gly Cys Ile Tyr Arg Lys His
1               5                   10                  15

Asp Val

<210> SEQ ID NO 168
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 168

Ile Ala Gln Leu Thr Glu Met Leu Arg Gly Cys Asn Tyr Arg Lys His
1               5                   10                  15

Asp Val

<210> SEQ ID NO 169
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 169

Gln Glu Glu Leu Ser Ser Ile Leu Arg Gly Cys Asn Tyr Arg Lys His
1               5                   10                  15

Asp Val

<210> SEQ ID NO 170
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 170

Ile Ala Gln Leu Ser Ser Ile Leu Arg Gly Cys His Leu Trp Lys His
1               5                   10                  15

Asp Val

<210> SEQ ID NO 171
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 171

Ile Ala Gln Leu Ser Ser Val Val Ile Gly Cys Asn Tyr Ser Lys His
1               5                   10                  15

Asp Val

<210> SEQ ID NO 172
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 172

Met Asn Gln Leu Asp His Phe Leu Arg Gly Cys Asn Tyr Arg Lys His
1               5                   10                  15

Asp Val

<210> SEQ ID NO 173
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 173

Ile Ala Gln Leu Pro His Asp Leu Arg Gly Cys Asn Tyr Arg Lys His
1               5                   10                  15

Asp Val

<210> SEQ ID NO 174
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 174

Ile Ala Gln Leu Ser Ser Ala Pro Asp Gly Cys Asn Tyr Arg Lys His
1               5                   10                  15

Asp Val

<210> SEQ ID NO 175
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 175

Ile Ala Gln Leu Ser Ser Ile Leu Arg Gly Cys Val Tyr Pro Lys His
1               5                   10                  15

Asp Val

<210> SEQ ID NO 176
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 176

Ile Ala Gln Leu Ser Ser Ile Arg Ala Gly Cys Asn Tyr Arg Lys His
1               5                   10                  15

Asp Val

<210> SEQ ID NO 177
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 177

Ile Ala Trp Gln Ser Ser Ile Leu Arg Gly Cys Asn Tyr Arg Lys His
1               5                   10                  15

Asp Val

<210> SEQ ID NO 178
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 178

Ile Ala Gln Leu Arg Lys Lys Leu Arg Gly Cys Asn Tyr Arg Lys His
1               5                   10                  15

Asp Val

<210> SEQ ID NO 179
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 179

Ile Ala Gln Leu Ser Ser Ile Leu Val Asn Cys Phe Tyr Arg Lys His
1               5                   10                  15

Asp Val

<210> SEQ ID NO 180
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 180

Ile Ala Gln Phe Ser Ser Ile Leu Cys Ser Cys Arg Tyr Arg Lys His
1               5                   10                  15

Asp Val

<210> SEQ ID NO 181
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 181

Ile Ala Gln Leu Ser Ser Ile Leu Phe Gly Cys Ala Tyr Arg Lys His
1               5                   10                  15

Asp Val

<210> SEQ ID NO 182
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 182

Ile Ala Gln Leu Ser Ser Ile Leu Phe Gly Cys Asp Tyr Arg Lys His
1               5                   10                  15

Asp Val

<210> SEQ ID NO 183
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 183

Ile Ala Gln Leu Ser Ser Ile Leu Arg Gly Cys Asn Tyr Leu Tyr Ile
1               5                   10                  15

Asp Val

<210> SEQ ID NO 184
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 184

Ile Ala Gln Leu Ser Ser Arg Lys Gly Gly Cys Asn Tyr Arg Lys His
1               5                   10                  15

Asp Val

<210> SEQ ID NO 185
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 185

Ile Ala Gln Leu Thr Gln Trp Leu Arg Gly Cys Asn Tyr Arg Lys His
1               5                   10                  15

Asp Val

<210> SEQ ID NO 186
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 186

Ile Ala Gln Gln Ser Ser Ile Leu Arg Gly Cys Asn Tyr Arg Lys His
1               5                   10                  15

Asp Val

<210> SEQ ID NO 187
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 187

Ile Ala Asp Val Gly Ser Ile Leu Arg Gly Cys Asn Tyr Arg Lys His
1               5                   10                  15

Asp Val

<210> SEQ ID NO 188
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 188

Ile Ala Gln Leu Ser Ser Ile Leu Leu Lys Cys Glu Tyr Arg Lys His
1               5                   10                  15

Asp Val

<210> SEQ ID NO 189
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 189

Ile Ala Gln Leu Ser Ser Met Tyr Lys Gly Cys Asn Tyr Arg Lys His
1               5                   10                  15

Asp Val

<210> SEQ ID NO 190
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 190

Ile Ala Gln Leu Ser Ser Ile Leu Arg Gly Cys Asn Tyr Asn Ile Asp
1               5                   10                  15

Asp Val

<210> SEQ ID NO 191
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 191

Leu Glu Lys Leu Ser Ser Ile Leu Arg Gly Cys Asn Tyr Arg Lys His
1               5                   10                  15

Asp Val

<210> SEQ ID NO 192
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 192

Leu Phe Asp Leu Ser Ser Ile Leu Arg Gly Cys Asn Tyr Arg Lys His
1               5                   10                  15

Asp Val

<210> SEQ ID NO 193
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 193

Pro His Met Leu Ser Ser Ile Leu Arg Gly Cys Asn Tyr Arg Lys His
1               5                   10                  15

Asp Val

<210> SEQ ID NO 194
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 194

Ile Ala Gln Leu His Thr His Leu Arg Gly Cys Asn Tyr Arg Lys His
1               5                   10                  15

Asp Val

<210> SEQ ID NO 195
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 195

Ile Ala Gln Leu Ser Ser Ile Leu Arg Gly Cys Ala Gly Val Lys His
1               5                   10                  15

Asp Val

<210> SEQ ID NO 196
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 196

Ile Ala Gln Leu Ser Ser Ile Leu Arg Gly Cys Lys Gln Phe Glu Tyr
1               5                   10                  15

Asp Val

<210> SEQ ID NO 197
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 197

Ile Ala Gln Leu Ser Ser Arg Glu Leu Gly Cys Asn Tyr Arg Lys His
1               5                   10                  15

Asp Val

<210> SEQ ID NO 198
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 198

Val Ala Leu Gln Glu Ser Ile Leu Arg Gly Cys Asn Tyr Arg Lys His
1               5                   10                  15

Asp Val

<210> SEQ ID NO 199
<211> LENGTH: 18
```

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 199

Val Ala Gln Leu Ser Ser His Tyr Asp Gly Cys Asn Tyr Arg Lys His
1               5                   10                  15

Asp Val

<210> SEQ ID NO 200
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 200

Ile Ala Gln Leu Ser Ser Ile Leu Phe Gly Cys Asn Tyr Phe Lys Asn
1               5                   10                  15

Asp Val

<210> SEQ ID NO 201
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 201

Ile Ala Gln Leu Ser Ser Ile Leu Arg Gly Cys Asn Tyr Lys Asn Val
1               5                   10                  15

Asp Val

<210> SEQ ID NO 202
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 202

Ile Ala Gln Leu Ser Ser Ile Leu Arg Gly Cys Asn Tyr Thr Leu Tyr
1               5                   10                  15

Asp Val

<210> SEQ ID NO 203
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 203

Ile Ala Gln Leu Lys Trp Gly Leu Arg Gly Cys Asn Tyr Arg Lys His
1               5                   10                  15

Asp Val

<210> SEQ ID NO 204
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 204

Ile Ala Gln Leu Ser Ser Ile Leu Arg Gly Cys Asn Tyr Asp Val Asn
1               5                   10                  15

Asp Val

<210> SEQ ID NO 205
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 205

Ile Ala Gln Leu Ser Ser Val Tyr Lys Gly Cys Asn Tyr Arg Lys His
1               5                   10                  15

Asp Val

<210> SEQ ID NO 206
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 206

Ile Ala Gln Leu Ser Ser Tyr Arg Pro Gly Cys Asn Tyr Arg Lys His
1               5                   10                  15

Asp Val

<210> SEQ ID NO 207
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 207

Ile Ala Gln Pro Ser Ser Ile Leu Arg Gly Cys Asn Tyr Gly Lys Leu
1               5                   10                  15

Asp Val

<210> SEQ ID NO 208
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 208

Ile Ala Leu His Arg Ser Ile Leu Arg Gly Cys Asn Tyr Arg Lys His
1               5                   10                  15

Asp Val

<210> SEQ ID NO 209
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 209

Ile Ala Gln Leu Asn His Tyr Leu Arg Gly Cys Asn Tyr Arg Lys His
1               5                   10                  15

Asp Val

<210> SEQ ID NO 210
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 210

Ile Ala Gln Leu Ser Ser Ile Leu Ala Leu Cys Met Tyr Arg Lys His
1               5                   10                  15

Asp Val

<210> SEQ ID NO 211
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 211

Ile Ala Gln Leu Ser Ser Arg Ala Met Gly Cys Asn Tyr Arg Lys His
1               5                   10                  15

Asp Val

<210> SEQ ID NO 212
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 212

Ile Ala Gln Leu Ser Ser Val Phe Ile Gly Cys Asn Tyr Arg Lys His
1               5                   10                  15

Asp Val

<210> SEQ ID NO 213
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 213

Ile Ala Thr Leu Gly Ser Ile Leu Arg Gly Cys Asn Tyr Arg Lys His
1               5                   10                  15

Asp Val

<210> SEQ ID NO 214
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 214

Ile Ala Gln Leu Ser Ser Ile Leu Arg Gly Cys Asn Tyr Arg Ala Ser
1               5                   10                  15

Asp Val

<210> SEQ ID NO 215
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 215

Ile Ala Gln Leu Ser Ser Ile Met Arg Gly Cys Asn Tyr Ile Met Arg
1               5                   10                  15

Asp Val

<210> SEQ ID NO 216
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 216

Ile Ala Gln Leu Ser Ser Val Lys Asp Gly Cys Asn Tyr Arg Lys His
1               5                   10                  15

Asp Val

<210> SEQ ID NO 217
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 217

Ile Ala Gln Leu Ser Ser Tyr Glu Thr Gly Cys Asn Tyr Arg Lys His
1               5                   10                  15

Asp Val

<210> SEQ ID NO 218
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 218

Ile Ala Gln Gln Asp Gln Asp Leu Arg Gly Cys Asn Tyr Arg Lys His
1               5                   10                  15

Asp Val

<210> SEQ ID NO 219
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 219

Ile Ala Lys Pro Asn Ser Ile Leu Arg Gly Cys Asn Tyr Arg Lys His
1               5                   10                  15

Asp Val

<210> SEQ ID NO 220
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 220

Ile Ala Gln Leu Ile Lys Asn Leu Arg Gly Cys Asn Tyr Arg Lys His
1               5                   10                  15

Asp Val

<210> SEQ ID NO 221
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 221

Ile Ala Gln Leu Ser Ser Ile Leu Arg Gly Cys Asn Gln Pro Lys His
1               5                   10                  15

Asp Val

<210> SEQ ID NO 222
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 222

Ile Ala Gln Leu Ser Ser Ile Leu Arg Gly Cys Asn Tyr Ala His Leu
1               5                   10                  15

Asp Val

<210> SEQ ID NO 223
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 223

Ile Ala Gln Leu Ser Ser Ile Leu Arg Gly Cys Asn Tyr Leu Asp Leu
1               5                   10                  15

Asp Val

<210> SEQ ID NO 224
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 224

Ile Ala Gln Leu Ser Ser Ile Leu Arg Gly Cys Asn Tyr Met His Pro
1               5                   10                  15

Asp Val

<210> SEQ ID NO 225
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 225

Asp Leu Thr Leu Ser Ser Ile Leu Arg Gly Cys Asn Tyr Arg Lys His
1               5                   10                  15

Asp Val

<210> SEQ ID NO 226
<211> LENGTH: 18

<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 226

Ile Ala Gln Leu Phe Pro Pro Leu Arg Gly Cys Asn Tyr Arg Lys His
1               5                   10                  15

Asp Val

<210> SEQ ID NO 227
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 227

Ile Ala Gln Leu Ser Ser Ala Gly Ile Gly Cys Asn Tyr Arg Lys His
1               5                   10                  15

Asp Val

<210> SEQ ID NO 228
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 228

Ile Ala Gln Leu Ser Ser Ile Leu Arg Gly Cys Asn Tyr Phe Gly Lys
1               5                   10                  15

Asp Val

<210> SEQ ID NO 229
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 229

Ile Ala Gln Leu Ser Ser Leu Ser Phe Gly Cys Asn Tyr Arg Lys His
1               5                   10                  15

Asp Val

<210> SEQ ID NO 230
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

-continued

<400> SEQUENCE: 230

Asp Ala His Leu Ser Ser Ile Leu Arg Gly Cys Asn Tyr Arg Lys His
1               5                   10                  15

Asp Val

<210> SEQ ID NO 231
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 231

Ile Ala Ile Thr Leu Ser Ile Leu Arg Gly Cys Asn Tyr Arg Lys His
1               5                   10                  15

Asp Val

<210> SEQ ID NO 232
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 232

Ile Ala Lys Ala Ser Ser Ile Leu Arg Gly Cys Asn Tyr Arg Lys His
1               5                   10                  15

Asp Val

<210> SEQ ID NO 233
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 233

Ile Ala Gln Leu His Ala Asn Leu Arg Gly Cys Asn Tyr Arg Lys His
1               5                   10                  15

Asp Val

<210> SEQ ID NO 234
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 234

Ile Ala Gln Leu His Cys Met Leu Arg Gly Cys Asn Tyr Arg Lys His
1               5                   10                  15

Asp Val

<210> SEQ ID NO 235
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 235

Ile Ala Gln Leu Ser Ser Gly His Arg Gly Cys Asn Tyr Arg Lys His
1               5                   10                  15

Asp Val

<210> SEQ ID NO 236
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 236

Ile Ala Gln Leu Ser Ser Ile Leu Gln Pro Cys Tyr Tyr Arg Lys His
1               5                   10                  15

Asp Val

<210> SEQ ID NO 237
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 237

Ile Ala Gln Leu Ser Ser Ile Leu Arg Gly Cys Glu Ala Arg Lys His
1               5                   10                  15

Asp Val

<210> SEQ ID NO 238
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 238

Ile Ala Gln Leu Ser Ser Ile Leu Arg Gly Cys Glu Gly Asp Lys His
1               5                   10                  15

Asp Val

<210> SEQ ID NO 239
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

<400> SEQUENCE: 239

Ile Ala Gln Leu Ser Ser Ile Leu Arg Gly Cys Asn Tyr Glu His His
1               5                   10                  15

Asp Val

<210> SEQ ID NO 240
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 240

Ile Ala Gln Leu Ser Ser Ile Leu Arg Gly Cys Asn Tyr His Pro His
1               5                   10                  15

Asp Val

<210> SEQ ID NO 241
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 241

Ile Ala Gln Leu Ser Ser Ile Leu Arg Gly Cys Asn Tyr Asn Gln Gln
1               5                   10                  15

Asp Val

<210> SEQ ID NO 242
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 242

Ile Ala Gln Leu Ser Ser Leu Glu Arg Gly Cys Asn Tyr Phe Gln Phe
1               5                   10                  15

Asp Val

<210> SEQ ID NO 243
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 243

Met Asp Gln Leu Ser Asn Met Leu Arg Gly Cys Asn Tyr Arg Lys His
1               5                   10                  15

Asp Val

<210> SEQ ID NO 244
<211> LENGTH: 18

```
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 244

Ile Ala Gln Leu Ala Phe Gly Leu Arg Gly Cys Asn Tyr Arg Lys His
1               5                   10                  15

Asp Val

<210> SEQ ID NO 245
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 245

Ile Ala Gln Leu Ser Ser Ile Leu Arg Gly Cys Gly Gly Ser Lys His
1               5                   10                  15

Asp Val

<210> SEQ ID NO 246
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 246

Ile Ala Gln Leu Ser Ser Ile Leu Arg Gly Cys Asn Tyr Lys Ile Ala
1               5                   10                  15

Asp Val

<210> SEQ ID NO 247
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 247

Ile Ala Gln Leu Ser Ser Gln Ser Val Gly Cys Asn Tyr Arg Lys His
1               5                   10                  15

Asp Val

<210> SEQ ID NO 248
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
```

```
<400> SEQUENCE: 248

Ile Ala Gln Leu Asn Val Ile Leu Arg Gly Cys Asn Tyr Arg Lys His
1               5                   10                  15

Asp Val

<210> SEQ ID NO 249
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 249

Ile Ala Gln Leu Ser Ser Asp Gly Gln Gly Cys Asn Tyr Arg Lys His
1               5                   10                  15

Asp Val

<210> SEQ ID NO 250
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 250

Ile Ala Gln Leu Ser Ser Ile Leu Arg Gly Cys Phe Pro Gln Lys His
1               5                   10                  15

Asp Val

<210> SEQ ID NO 251
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 251

Ile Ala Gln Leu Ser Ser Ile Leu Arg Gly Cys Ile Ala Gly Lys His
1               5                   10                  15

Asp Val

<210> SEQ ID NO 252
<211> LENGTH: 18
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 252

Ile Ala Gln Leu Ser Ser Asn Arg Asn Gly Cys Asn Tyr Arg Lys His
1               5                   10                  15

Asp Val
```